US 9,883,968 B2

(12) United States Patent
Doud et al.

(10) Patent No.: US 9,883,968 B2
(45) Date of Patent: Feb. 6, 2018

(54) FLUID EXCHANGE APPARATUS AND METHODS

(75) Inventors: Darren Doud, Menlo Park, CA (US); Randolph E. Campbell, Menlo Park, CA (US); Signe Erickson, Menlo Park, CA (US); K. Angela MacFarlane, Menlo Park, CA (US); Mike Barrett, Menlo Park, CA (US); Christina Skieller, Menlo Park, CA (US); David Batten, Menlo Park, CA (US); Greg Stine, Menlo Park, CA (US); Eugene de Juan, Jr., Menlo Park, CA (US); Douglas Sutton, Menlo Park, CA (US); Kathleen Cogan Farinas, Menlo Park, CA (US)

(73) Assignee: ForSight Vision4, Inc., Menlo Park, CA (US)

( * ) Notice: Subject to any disclaimer, the term of this patent is extended or adjusted under 35 U.S.C. 154(b) by 0 days.

(21) Appl. No.: 13/615,229

(22) Filed: Sep. 13, 2012

(65) Prior Publication Data
US 2013/0165860 A1 Jun. 27, 2013

Related U.S. Application Data

(60) Provisional application No. 61/535,900, filed on Sep. 16, 2011, provisional application No. 61/595,604, filed on Feb. 6, 2012.

(51) Int. Cl.
*A61F 9/00* (2006.01)
*A61M 25/00* (2006.01)
(Continued)

(52) U.S. Cl.
CPC ......... *A61F 9/0008* (2013.01); *A61M 25/007* (2013.01); *A61M 39/0247* (2013.01);
(Continued)

(58) Field of Classification Search
CPC .. A61M 2025/0031; A61M 2025/0034; A61M 2025/0039; A61M 2210/0612;
(Continued)

(56) References Cited

U.S. PATENT DOCUMENTS 1,747,814 A * 2/1930 Bradley .................. F16K 31/32
137/122
2,564,977 A 8/1951 Hu
(Continued)

FOREIGN PATENT DOCUMENTS

EP 0033042 8/1984
EP 0228185 7/1990
(Continued)

OTHER PUBLICATIONS

U.S. Appl. No. 13/814,461, filed Aug. 14, 2013, 2013/0324918.
(Continued)

*Primary Examiner* — Theodore Stigell
*Assistant Examiner* — Benjamin Koo
(74) *Attorney, Agent, or Firm* — Mintz Levin Cohn Ferris Glovsky and Popeo, P.C.

(57) ABSTRACT

An injector apparatus comprises an elongate structure having one or more openings positionable near a penetrable barrier of an implantable device so as to receive fluid of the implantable device. The apparatus comprises a needle and a sheath extending over at least a portion of the needle. The elongate structure may comprise a distal tip to penetrate tissue and the penetrable barrier, and a distal opening near the tip to release therapeutic fluid into the implantable chamber. In many embodiments the distal tip, the distal opening, and the plurality of openings are separated from a stop that engages a tissue of the patient and limit penetration depth such that the distal opening and the plurality of
(Continued)

openings are located along an axis of the implantable device to increase an efficiency of the exchange.

20 Claims, 58 Drawing Sheets

(51) Int. Cl.
*A61M 39/02* (2006.01)
*A61M 5/14* (2006.01)
*A61M 5/32* (2006.01)
*A61M 5/46* (2006.01)
*A61M 39/00* (2006.01)
*A61M 5/142* (2006.01)

(52) U.S. Cl.
CPC ............ *A61F 9/0017* (2013.01); *A61M 5/141* (2013.01); *A61M 5/14276* (2013.01); *A61M 5/3202* (2013.01); *A61M 5/3291* (2013.01); *A61M 5/46* (2013.01); *A61M 2025/0031* (2013.01); *A61M 2025/0039* (2013.01); *A61M 2039/009* (2013.01); *A61M 2039/0081* (2013.01); *A61M 2039/027* (2013.01); *A61M 2039/0276* (2013.01); *A61M 2039/0294* (2013.01); *A61M 2205/6045* (2013.01); *A61M 2205/6054* (2013.01); *A61M 2209/045* (2013.01); *A61M 2210/0612* (2013.01)

(58) Field of Classification Search
CPC .......... A61M 2039/0276; A61M 1/005; A61M 2039/2473; A61M 2039/248; A61M 25/007; F16K 31/32; A61F 9/0008
USPC ..................................... 604/43–44, 117, 6.14
See application file for complete search history.

(56) References Cited

U.S. PATENT DOCUMENTS

| | | | |
|---|---|---|---|
| 2,585,815 A | 2/1952 | McLintock | |
| 3,232,117 A | 2/1966 | Gilmont | |
| 3,416,530 A | 12/1968 | Ness | |
| 3,612,089 A * | 10/1971 | Beguiristain | 137/115.02 |
| 3,618,604 A | 11/1971 | Ness | |
| 3,641,237 A | 2/1972 | Gould et al. | |
| 3,734,095 A | 5/1973 | Santomieri | |
| 3,828,777 A | 8/1974 | Ness | |
| 3,831,583 A | 8/1974 | Edmunds, Jr. et al. | |
| 3,845,201 A | 10/1974 | Haddad | |
| 3,902,495 A | 9/1975 | Weiss et al. | |
| 3,914,402 A | 10/1975 | Shell | |
| 3,916,899 A | 11/1975 | Theeuwes et al. | |
| 3,926,188 A | 12/1975 | Baker et al. | |
| 3,949,748 A | 4/1976 | Malmin | |
| 3,949,750 A | 4/1976 | Freeman | |
| 3,961,628 A | 6/1976 | Arnold | |
| 3,977,404 A | 8/1976 | Theeuwes | |
| 3,995,635 A | 12/1976 | Higuchi et al. | |
| 4,008,719 A | 2/1977 | Theeuwes et al. | |
| 4,014,333 A | 3/1977 | McIntyre | |
| 4,014,334 A | 3/1977 | Theeuwes et al. | |
| 4,014,335 A | 3/1977 | Arnold | |
| 4,034,756 A | 7/1977 | Higuchi et al. | |
| 4,034,758 A | 7/1977 | Theeuwes | |
| 4,077,407 A | 3/1978 | Theeuwes et al. | |
| 4,111,201 A | 9/1978 | Theeuwes | |
| 4,111,203 A | 9/1978 | Theeuwes | |
| 4,135,514 A | 1/1979 | Zaffaroni et al. | |
| 4,160,452 A | 7/1979 | Theeuwes | |
| 4,164,559 A | 8/1979 | Miyata et al. | |
| 4,179,497 A | 12/1979 | Cohen et al. | |
| 4,186,184 A | 1/1980 | Zaffaroni | |
| 4,200,098 A | 4/1980 | Ayer et al. | |
| 4,220,152 A | 9/1980 | Dresback | |
| 4,220,153 A | 9/1980 | Dresback | |
| 4,256,108 A | 3/1981 | Theeuwes | |
| 4,298,000 A | 11/1981 | Thill et al. | |
| 4,300,557 A | 11/1981 | Refojo et al. | |
| 4,309,776 A | 1/1982 | Berguer | |
| 4,326,525 A | 4/1982 | Swanson et al. | |
| 4,327,725 A | 5/1982 | Cortese et al. | |
| 4,343,787 A | 8/1982 | Katz | |
| 4,439,196 A | 3/1984 | Higuchi | |
| 4,439,198 A | 3/1984 | Brightman, II et al. | |
| 4,475,916 A | 10/1984 | Himmelstein | |
| 4,484,922 A | 11/1984 | Rosenwald | |
| 4,519,801 A | 5/1985 | Edgren | |
| 4,609,374 A | 9/1986 | Ayer | |
| 4,627,850 A | 12/1986 | Deters et al. | |
| 4,634,418 A | 1/1987 | Binder | |
| 4,634,427 A | 1/1987 | Hannula et al. | |
| 4,673,405 A | 6/1987 | Guittard et al. | |
| 4,693,886 A | 9/1987 | Ayer | |
| 4,712,550 A | 12/1987 | Sinnett | |
| 4,730,013 A | 3/1988 | Bondi et al. | |
| 4,737,150 A | 4/1988 | Baeumle et al. | |
| 4,774,091 A | 9/1988 | Yamahira et al. | |
| 4,777,049 A | 10/1988 | Magruder et al. | |
| 4,781,675 A | 11/1988 | White | |
| 4,851,228 A | 7/1989 | Zentner et al. | |
| 4,853,229 A | 8/1989 | Theeuwes | |
| 4,863,457 A | 9/1989 | Lee | |
| 4,865,846 A | 9/1989 | Kaufman | |
| 4,883,459 A | 11/1989 | Calderon | |
| 4,959,217 A | 9/1990 | Sanders et al. | |
| 4,979,938 A | 12/1990 | Stephen et al. | |
| 5,049,142 A | 9/1991 | Herrick et al. | |
| 5,053,030 A | 10/1991 | Herrick et al. | |
| 5,084,021 A | 1/1992 | Baldwin | |
| 5,098,443 A | 3/1992 | Parel et al. | |
| 5,128,145 A | 7/1992 | Edgren et al. | |
| 5,141,748 A | 8/1992 | Rizzo | |
| 5,147,647 A | 9/1992 | Darougar | |
| 5,164,188 A | 11/1992 | Wong | |
| 5,171,270 A | 12/1992 | Herrick | |
| 5,174,999 A | 12/1992 | Magruder et al. | |
| 5,238,687 A | 8/1993 | Magruder et al. | |
| 5,273,530 A | 12/1993 | del Cerro et al. | |
| 5,277,912 A | 1/1994 | Lowe et al. | |
| 5,282,829 A | 2/1994 | Hermes | |
| 5,300,114 A | 4/1994 | Gwon et al. | |
| 5,322,504 A | 6/1994 | Doherty et al. | |
| 5,322,691 A | 6/1994 | Darougar et al. | |
| 5,324,518 A | 6/1994 | Orth et al. | |
| 5,334,189 A | 8/1994 | Wade | |
| 5,336,175 A | 8/1994 | Mames | |
| 5,364,343 A | 11/1994 | Apolet et al. | |
| 5,378,475 A | 1/1995 | Smith et al. | |
| 5,413,572 A | 5/1995 | Wong et al. | |
| 5,443,505 A | 8/1995 | Wong et al. | |
| 5,466,233 A | 11/1995 | Weiner et al. | |
| 5,476,448 A | 12/1995 | Urich | |
| 5,476,511 A | 12/1995 | Gwon et al. | |
| 5,554,132 A | 9/1996 | Straits et al. | |
| 5,562,915 A | 10/1996 | Lowe et al. | |
| 5,576,480 A | 11/1996 | Hopkins et al. | |
| 5,578,042 A | 11/1996 | Cumming | |
| 5,674,193 A * | 10/1997 | Hayes | 604/28 |
| 5,681,572 A | 10/1997 | Seare, Jr. | |
| 5,725,493 A | 3/1998 | Avery et al. | |
| 5,755,684 A * | 5/1998 | Chen | 604/35 |
| 5,766,242 A | 6/1998 | Wong et al. | |
| 5,770,076 A | 6/1998 | Chu et al. | |
| 5,773,019 A | 6/1998 | Ashton et al. | |
| 5,797,898 A | 8/1998 | Santini, Jr. et al. | |
| 5,807,581 A | 9/1998 | Rosenblatt et al. | |
| 5,817,075 A | 10/1998 | Giungo | |
| 5,824,072 A | 10/1998 | Wong | |
| 5,830,173 A | 11/1998 | Avery et al. | |
| 5,830,492 A | 11/1998 | Usala | |
| 5,830,546 A | 11/1998 | Ehret et al. | |
| 5,836,935 A | 11/1998 | Ashton et al. | |
| 5,868,697 A | 2/1999 | Richter et al. | |

(56) References Cited

U.S. PATENT DOCUMENTS

| | | | |
|---|---|---|---|
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,468,264 B1 | 10/2002 | Gillis et al. |
| 6,472,162 B1 | 10/2002 | Coelho et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,695,821 B1 | 2/2004 | Sjaarda |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,869,412 B2 | 3/2005 | Ross |
| 6,932,983 B1 | 8/2005 | Straub et al. |
| 6,976,982 B2 | 12/2005 | Santini et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 * | 11/2006 | Diermann et al. ............. 600/573 |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,699,820 B1 | 4/2010 | French |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,905,963 B2 | 12/2014 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0188244 A1 | 12/2002 | Smith |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0047011 A1 | 3/2003 | Diermann et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 * | 2/2004 | Plicchi et al. ................ 604/264 |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0209359 A1 | 10/2004 | Yayon et al. |
| 2004/0230183 A1 * | 11/2004 | Breegi ................. A61F 9/0017 604/891.1 |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | de Juan, Jr. et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0255144 A1 | 11/2005 | Schultz et al. |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | DeJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0083155 A1 | 4/2007 | Muller |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |

(56) References Cited

U.S. PATENT DOCUMENTS

| | | |
|---|---|---|
| 2007/0141111 A1 | 6/2007 | Suokas et al. |
| 2007/0191863 A1 | 8/2007 | de Juan, Jr. et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford, III et al. |
| 2007/0235331 A1 | 10/2007 | Simpson et al. |
| 2007/0243230 A1 | 10/2007 | de Juan, Jr. et al. |
| 2007/0260201 A1 | 11/2007 | Prausnitz et al. |
| 2007/0265599 A1 | 11/2007 | Castillejos |
| 2007/0269487 A1 | 11/2007 | de Juan, Jr. et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0108954 A1* | 5/2008 | Mathias ............ A61M 1/0209 604/248 |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0012485 A1* | 1/2009 | Michaels et al. ............ 604/320 |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0061071 A1 | 3/2009 | McMorrow et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan, Jr. et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | de Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Saabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2009/0326489 A1 | 12/2009 | Kensy et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0191176 A1 | 7/2010 | Ho et al. |
| 2010/0197512 A1 | 8/2010 | Trinkle et al. |
| 2010/0211041 A1 | 8/2010 | Omori et al. |
| 2010/0216702 A1 | 8/2010 | Szkudlinski et al. |
| 2010/0221309 A1 | 9/2010 | Myers et al. |
| 2010/0227904 A1 | 9/2010 | Kabra et al. |
| 2010/0255061 A1 | 10/2010 | De Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |

(56) References Cited

U.S. PATENT DOCUMENTS

| | | | |
|---|---|---|---|
| 2011/0117083 A1 | 5/2011 | Bais et al. | |
| 2011/0125178 A1 | 5/2011 | Drews et al. | |
| 2011/0159073 A1 | 6/2011 | De Juan et al. | |
| 2011/0190723 A1 | 8/2011 | Fangrow | |
| 2011/0206646 A1 | 8/2011 | Alfonso et al. | |
| 2011/0281901 A1 | 11/2011 | Gupta | |
| 2012/0029445 A1 | 2/2012 | De Juan, Jr. et al. | |
| 2012/0029470 A1 | 2/2012 | De Juan, Jr. et al. | |
| 2013/0245544 A1* | 9/2013 | de Juan, Jr. ............ A61F 9/0017 604/44 |
| 2013/0324942 A1 | 12/2013 | de Juan, Jr. et al. | |

FOREIGN PATENT DOCUMENTS

| | | |
|---|---|---|
| EP | 0498471 | 8/1992 |
| EP | 0500143 | 8/1992 |
| EP | 0295248 | 3/1993 |
| EP | 0671165 | 9/1995 |
| EP | 0944658 | 6/2003 |
| EP | 1671624 | 6/2006 |
| EP | 1385452 | 9/2006 |
| EP | 1409065 | 1/2007 |
| EP | 1337284 | 12/2007 |
| EP | 1911481 | 4/2008 |
| EP | 1521572 | 3/2009 |
| JP | 01-149716 | 6/1989 |
| JP | 01-197429 | 8/1989 |
| JP | 08509636 A | 10/1996 |
| JP | 2001-518880 A | 10/2001 |
| JP | 2004-516889 A | 6/2004 |
| WO | WO 88/04573 | 6/1988 |
| WO | WO 90/07545 | 7/1990 |
| WO | WO-9424969 | 11/1994 |
| WO | WO 95/28984 | 11/1995 |
| WO | WO 97/29850 | 8/1997 |
| WO | WO 98/25982 | 6/1998 |
| WO | WO-9843611 A1 | 10/1998 |
| WO | WO 99/11244 | 3/1999 |
| WO | WO 00/48660 | 8/2000 |
| WO | WO 01/26714 | 4/2001 |
| WO | WO 01/50943 | 7/2001 |
| WO | WO 01/68016 | 9/2001 |
| WO | WO-02053128 A2 | 7/2002 |
| WO | WO 02/100318 | 12/2002 |
| WO | WO-03028765 | 4/2003 |
| WO | WO 03/077972 | 9/2003 |
| WO | WO 03/082188 | 10/2003 |
| WO | WO 2004/000267 | 12/2003 |
| WO | WO 2004/112653 | 12/2004 |
| WO | WO 2005/016401 | 2/2005 |
| WO | WO 2005/027906 | 3/2005 |
| WO | WO 2005/028006 | 3/2005 |
| WO | WO-2005025413 A2 | 3/2005 |
| WO | WO 2005025413 A2 | 3/2005 |
| WO | WO 2005/091922 | 10/2005 |
| WO | WO 2005/107705 | 11/2005 |
| WO | WO 2005/110362 | 11/2005 |
| WO | WO 2005/110436 | 11/2005 |
| WO | WO 2005/110473 | 11/2005 |
| WO | WO 2005/117780 | 12/2005 |
| WO | WO 2006/014484 | 2/2006 |
| WO | WO 2006/015385 | 2/2006 |
| WO | WO 2006/023530 | 3/2006 |
| WO | WO 2006/031358 | 3/2006 |
| WO | WO 2006/031388 | 3/2006 |
| WO | WO 2006/044614 | 4/2006 |
| WO | WO 2006/050221 | 5/2006 |
| WO | WO 2006/068838 | 6/2006 |
| WO | WO 2006/071554 | 7/2006 |
| WO | WO 2006/082588 | 8/2006 |
| WO | WO 2006/108054 | 10/2006 |
| WO | WO 2006/127962 | 11/2006 |
| WO | WO 2006/138609 | 12/2006 |
| WO | WO 2007/012974 | 2/2007 |
| WO | WO 2007/035473 | 3/2007 |
| WO | WO 2007/035621 | 3/2007 |
| WO | WO 2007/038453 | 4/2007 |
| WO | WO 2007/044534 | 4/2007 |
| WO | WO 2007/047744 | 4/2007 |
| WO | WO 2007/066339 | 6/2007 |
| WO | WO 2007/084582 | 7/2007 |
| WO | WO 2007/084765 | 7/2007 |
| WO | WO 2007/101204 | 9/2007 |
| WO | WO 2007/115259 | 10/2007 |
| WO | WO 2007/117394 | 10/2007 |
| WO | WO 2007/131050 | 11/2007 |
| WO | WO 2007/133761 | 11/2007 |
| WO | WO 2007/133762 | 11/2007 |
| WO | WO 2008/003043 | 1/2008 |
| WO | WO 2008/005240 | 1/2008 |
| WO | WO 2008/011125 | 1/2008 |
| WO | WO 2008/019265 | 2/2008 |
| WO | WO 2008/033924 | 3/2008 |
| WO | WO 2008/040062 | 4/2008 |
| WO | WO 2008/045272 | 4/2008 |
| WO | WO 2008/052145 | 5/2008 |
| WO | WO 2008/060359 | 5/2008 |
| WO | WO 2008/061043 | 5/2008 |
| WO | WO 2008/076544 | 6/2008 |
| WO | WO 2008/094989 | 8/2008 |
| WO | WO 2008/115290 | 9/2008 |
| WO | WO 2008/116165 | 9/2008 |
| WO | WO 2008/144340 | 11/2008 |
| WO | WO 2008/144919 | 12/2008 |
| WO | WO 2009/012075 | 1/2009 |
| WO | WO 2009/023615 | 2/2009 |
| WO | WO 2009/046164 | 4/2009 |
| WO | WO 2009/055620 | 4/2009 |
| WO | WO 2009/055671 | 4/2009 |
| WO | WO 2009/055729 | 4/2009 |
| WO | WO 2009/055824 | 4/2009 |
| WO | WO 2009/061607 | 5/2009 |
| WO | WO 2009/073192 | 6/2009 |
| WO | WO 2009/086112 | 7/2009 |
| WO | WO 2009/089409 | 7/2009 |
| WO | WO 2009/094466 | 7/2009 |
| WO | WO 2009/112878 | 9/2009 |
| WO | WO 2009/117112 | 9/2009 |
| WO | WO 2009/124096 | 10/2009 |
| WO | WO 2009/128932 | 10/2009 |
| WO | WO 2009/134929 | 11/2009 |
| WO | WO 2009/137777 | 11/2009 |
| WO | WO-2009137780 A2 | 11/2009 |
| WO | WO 2010/008424 | 1/2010 |
| WO | WO 2010/021993 | 2/2010 |
| WO | WO 2010/047753 | 4/2010 |
| WO | WO 2010/062628 | 6/2010 |
| WO | WO 2010/066714 | 6/2010 |
| WO | WO 2010/075565 | 7/2010 |
| WO | WO 2010/078063 | 7/2010 |
| WO | WO 2010/088548 | 8/2010 |
| WO | WO 2010/093945 | 8/2010 |
| WO | WO 2010/095940 | 8/2010 |
| WO | WO 2010/125416 | 11/2010 |
| WO | WO 2010/126908 | 11/2010 |
| WO | WO 2010/135369 | 11/2010 |
| WO | WO 2010/141729 | 12/2010 |
| WO | WO 2010/147661 | 12/2010 |
| WO | WO 2011/008896 | 1/2011 |
| WO | WO 2011/008897 | 1/2011 |
| WO | WO 2011/028850 | 3/2011 |
| WO | WO 2011/034627 | 3/2011 |
| WO | WO 2011/079232 | 6/2011 |
| WO | WO 2012/019136 | 2/2012 |
| WO | WO-2012019047 | 2/2012 |
| WO | WO-2013003620 | 1/2013 |
| WO | WO-2013022801 | 2/2013 |

OTHER PUBLICATIONS

U.S. Appl. No. 13/814,464, filed Aug. 14, 2013, 2013/0324942.
U.S. Appl. No. 13/814,466, filed Jun. 28, 2013, 2013/0274691.

(56) References Cited

OTHER PUBLICATIONS

U.S. Appl. No. 13/814,470, filed Jun. 19, 2013, 2013/0274692.
U.S. Appl. No. 13/831,695, filed Mar. 15, 2013, 2013/0204209.
U.S. Appl. No. 13/849,445, filed Mar. 22, 2013, 2013/0218081.
U.S. Appl. No. 13/884,343, filed Oct. 14, 2013, 2014/0033800.
U.S. Appl. No. 13/889,328, filed May 7, 2013, 2013/0245544.
U.S. Appl. No. 13/889,339, filed May 7, 2013, 2013/0245573.
U.S. Appl. No. 13/942,610, filed Jul. 15, 2013, 2013/0304031.
U.S. Appl. No. 13/988,298, filed Oct. 14, 2013, 2014/0031769.
PCT/US2012/055216, Sep. 13, 2012, WO2013/040247.
PCT/US2013/022770, Jan. 23, 2013, WO2013/116061.
International Search Report and Written Opinion of PCT Application No. PCT/US2010/022631, dated May 18, 2010, 11 pages total.
Andrews, "Effect of nonsteroidal anti-inflammatory drugs on LFA-1 and ICAM-1 expression in gastric mucosa," Am J Physiol. Apr. 1994;266(4 Pt 1):G657-664.
Arvo, Agenda for the *Summer Eye Research Conference*, (Jul. 2009).
Avery et al., "Intravitreal bevacizumab (Avastin) in the treatment of proliferative diabetic retinopathy," Ophthalmology. Oct. 2006, 113(10):1695-1705.e6.
Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences, Apr. 1973; 62(4):617-621.
Breslin, C.W., et al., "Chapter 7. Slow Release Artificial Tears", *Symposium on Ocular Therapy* pp. 77-83, 1977.
Castro et al., "Effect of COX inhibitors on VEGF-induced retinal vascular leakage and experimental corneal and choroidal neovascularization," Exp Eye Res. Aug. 2004;79(2):275-285.
Chirila et al., "The Vitreous Humor" in *Handbook of Biomaterial Properties*, eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010.
Deissler et al., "VEGF-induced effects on proliferation, migration and tight junctions are restored by ranibizumab (Lucentis) in microvascular retinal endothelial cells,"Br J Ophthalmol 2008; 92:839-843.
Del Amo, et al., Current & future ophthalmic drug delivery systems . . . , *Drug Discovery Today*, vol. 13, Nos. 3/4, Feb. 2008.
Donoso et al., "The role of inflammation in the pathogenesis of age-related macular degeneration," Surv Ophthalmol. Mar.-Apr. 2006;51(2):137-52.
Duvvuri et al., Drug Delivery to the Retina: Challenges and Opportunities, *Expert Opinion on Biological Therapy*, 2003, vol. 3(1): 45-56.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudana et al., Recent Perspectives in Ocular Drug Delivery, *Pharmaceutical Research*, 2008.
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Haller, An Overview of Sustained-release Drug Implants, Retinal Physician, Jan. 2008.
Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038 ;discussion 2039.
Janoria et al., Novel Approaches to Retinal Drug Delivery, *Expert Opinion Drug Delivery*, 2007.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Li, et al., An electrochemical intraocular drug delivery device, *Science Direct, Sensors and Actuators*, www.sciencedirect.com,Jul. 4, 2007.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency ; retrieved from the Internet<http://www.ema.europa.eu/docs/en_GB/document_library/EPAR_-_Assessment_Report_-_Variation/human/000715/WC500101009.pdf> 2010/2011.
MAbPac SCX-10 Column for Monoclonal Antibody Variant Analysis, http://www.dionex.com/en-us/webdocs/87008-DS-MAbPac-SCX-10-Column-20Aug2010-LPN2567-03.pdf.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., *Thermophysical Properties of Trehalose and Its Concentrated Aqueous Solutions*, Pharmaceutical Research, vol. 14, No. 5, 1997, pp. 578-590.
Molokhia et al, "Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", *Investigative Ophthalmology & Visual Science* 32-6 (1991) pp. 1785-1790.
Mott Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Nutan, MTH, et al., *General Principles of Suspensions, in Pharmaceutical Suspensions Fron Formulation Development to Manufacturing*, editors AK Kulshreshtha, et al., Spinger, 2010.
Okabe et al., "Intraocular tissue distribution of betamethasone after intrascleral administration using a non-biodegradable sustained

(56) References Cited

OTHER PUBLICATIONS drug delivery device," Investigative Ophthalmology and Visual Science. 2003;44:2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm.

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).

Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.

Smith et al., "Spectrophotometric determination of $pK_a$ values for fluorescein using activity coefficient corrections," WaterSA 2002; 28(4):395-402.

Smith, T.J., et al., "Intravitreal Sustained-Release Ganciclovir", *Arch. Ophthamol* 110 (1992) pp. 255-258.

Soheilian et al., "Pilot Study of Intravitreal Injection of Diclofenac for Treatment of Macular Edema of Various Etiologies," Retina, Mar. 2010; 30(3): 509-515.

Stay et al. Computer Simulation of Convective and Diffusive Transport of Controlled-Release Drugs in the vitreous Humor, *Pharm Res* 2003,20(1), pp. 96-102.

Theodossiadis et al., "Intravitreal administration of the anti-tumor necrosis factor agent infliximab for neovascular age-related macular degeneration," Am J Ophthalmol. May 2009;147(5):825-830.

Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.

Williams et al., "Treating Diabetic Macular Edema With Ocular NSAIDs," Retinal Physician, Nov. 2007; retrieved from the Internet: http://www.retinalphysician.com/article.aspx?article=101096>, 5 pages total.

Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.

Yao et al. (Prevention of Laser Photocoagulation Induced Choroidal Neovascularization Lesions by Intravitreal Doses of Ranibizumab in Cynomolgus Monkeys, ARVO 2009 abstract D906).

Carbonaro, et al. "Nano-pore silicon membrane characterization by diffusion and electrical resistance." *Journal of Membrane Science*. 241 (2004):249-255.

Jornitz et al. "Filter Integrity Testing in Liquid Applications, Revisited; Part 1." *Pharmaceutical Technology*. Oct. 2001. pp: 34-50.

Millipore. "Filter Integrity Test Methods." *Millipore Corporation*. 1999.

\* cited by examiner

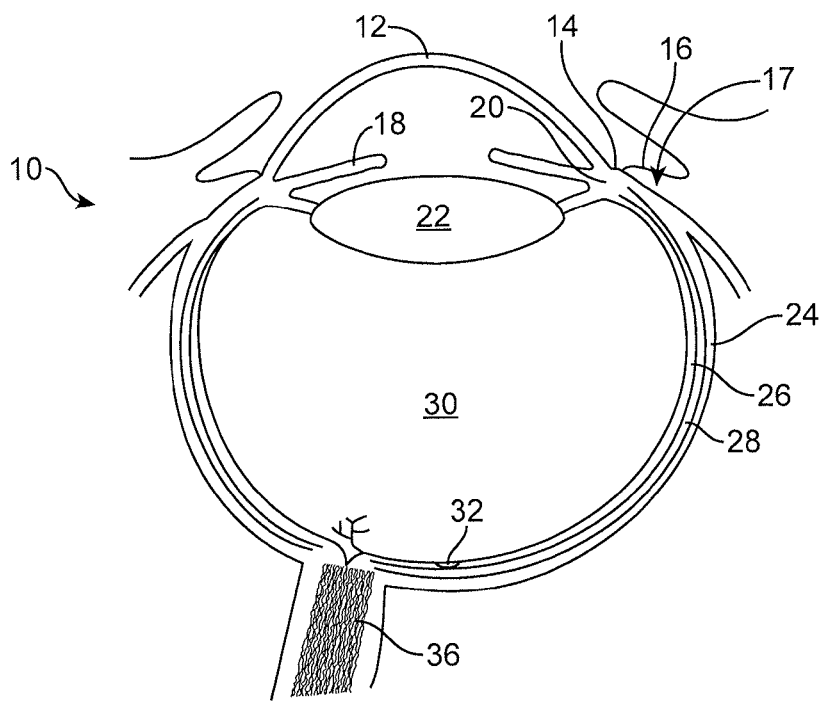
FIG. 1
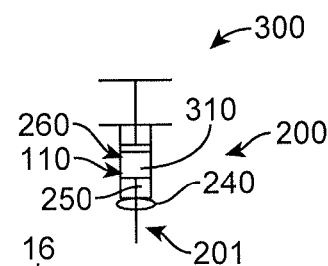
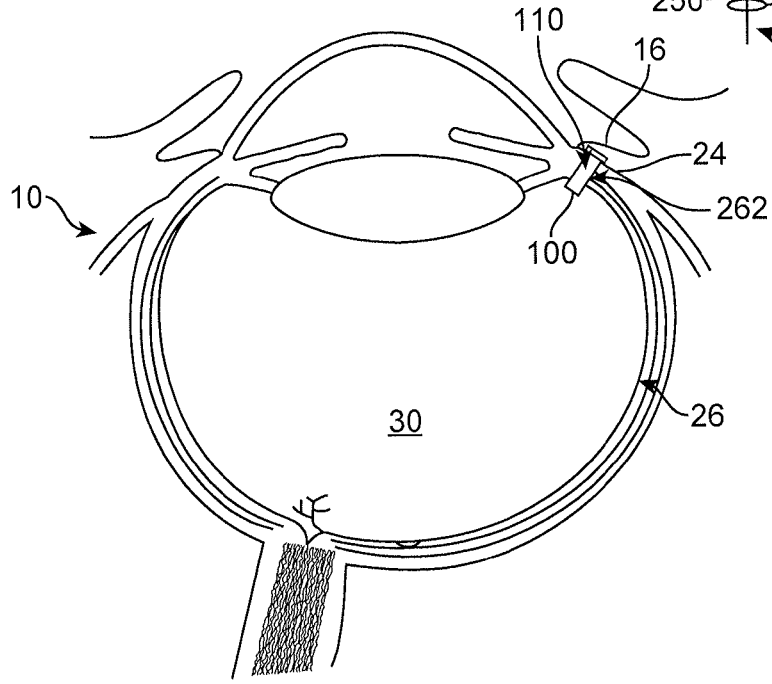
FIG. 2

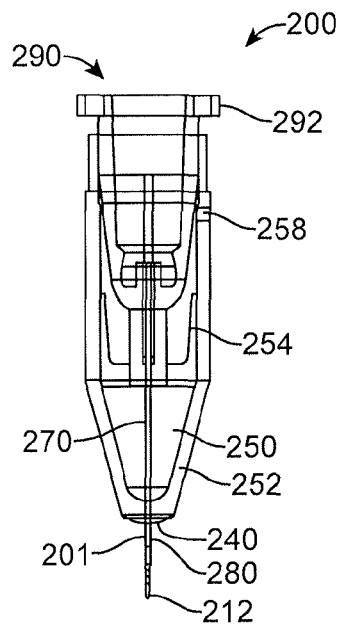
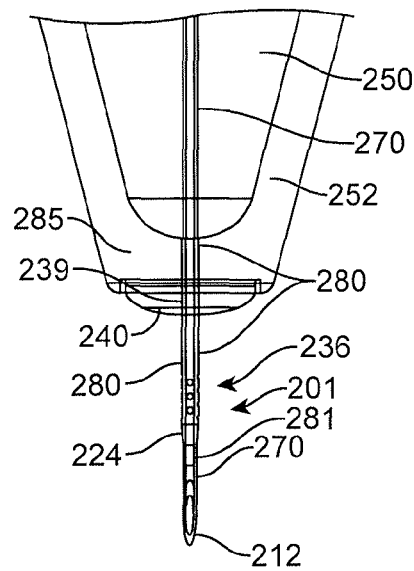
FIG. 7A  FIG. 7B
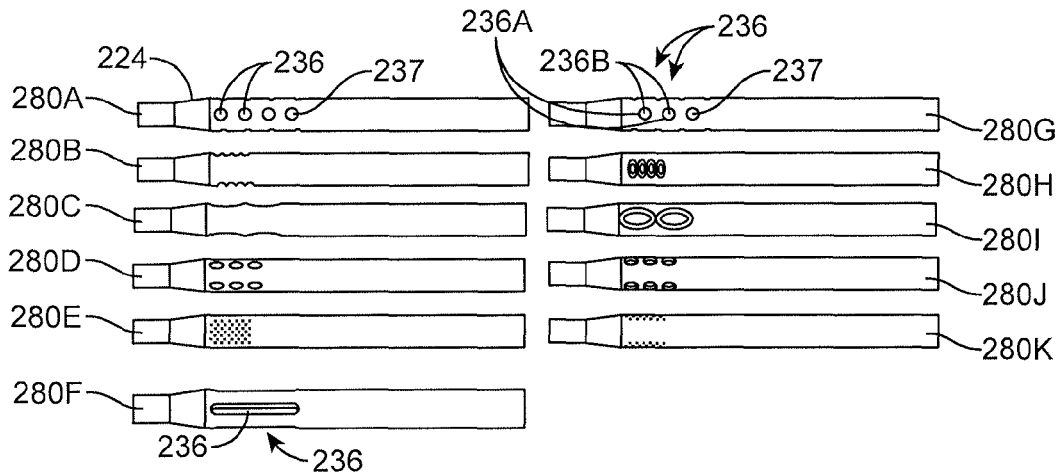
FIG. 7C
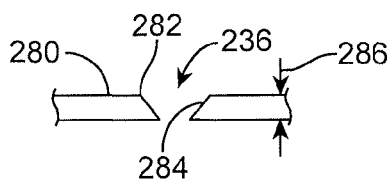
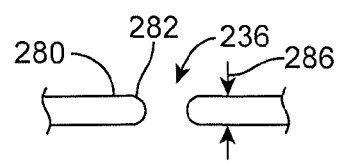
FIG. 7D  FIG. 7E

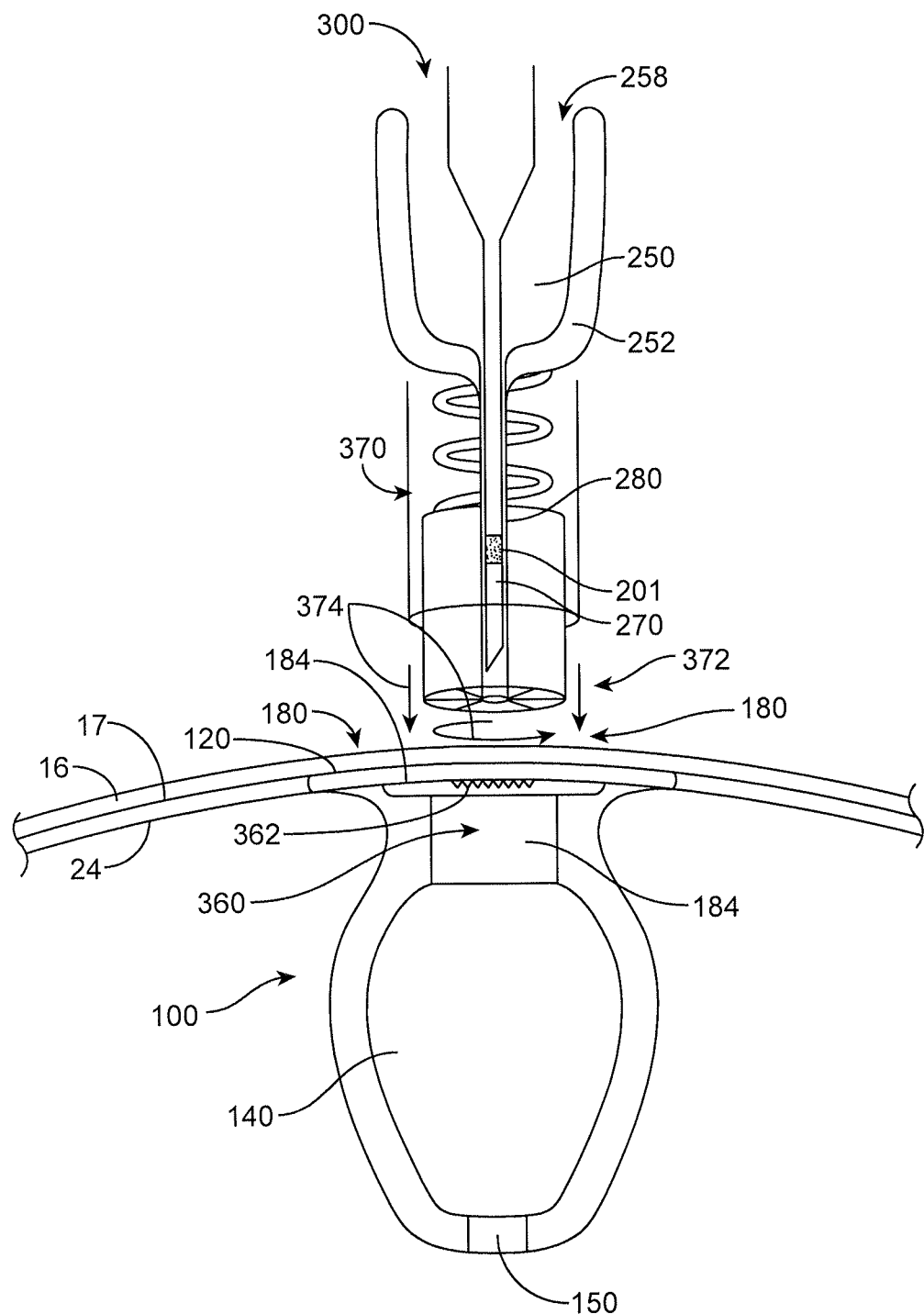
FIG. 8C1

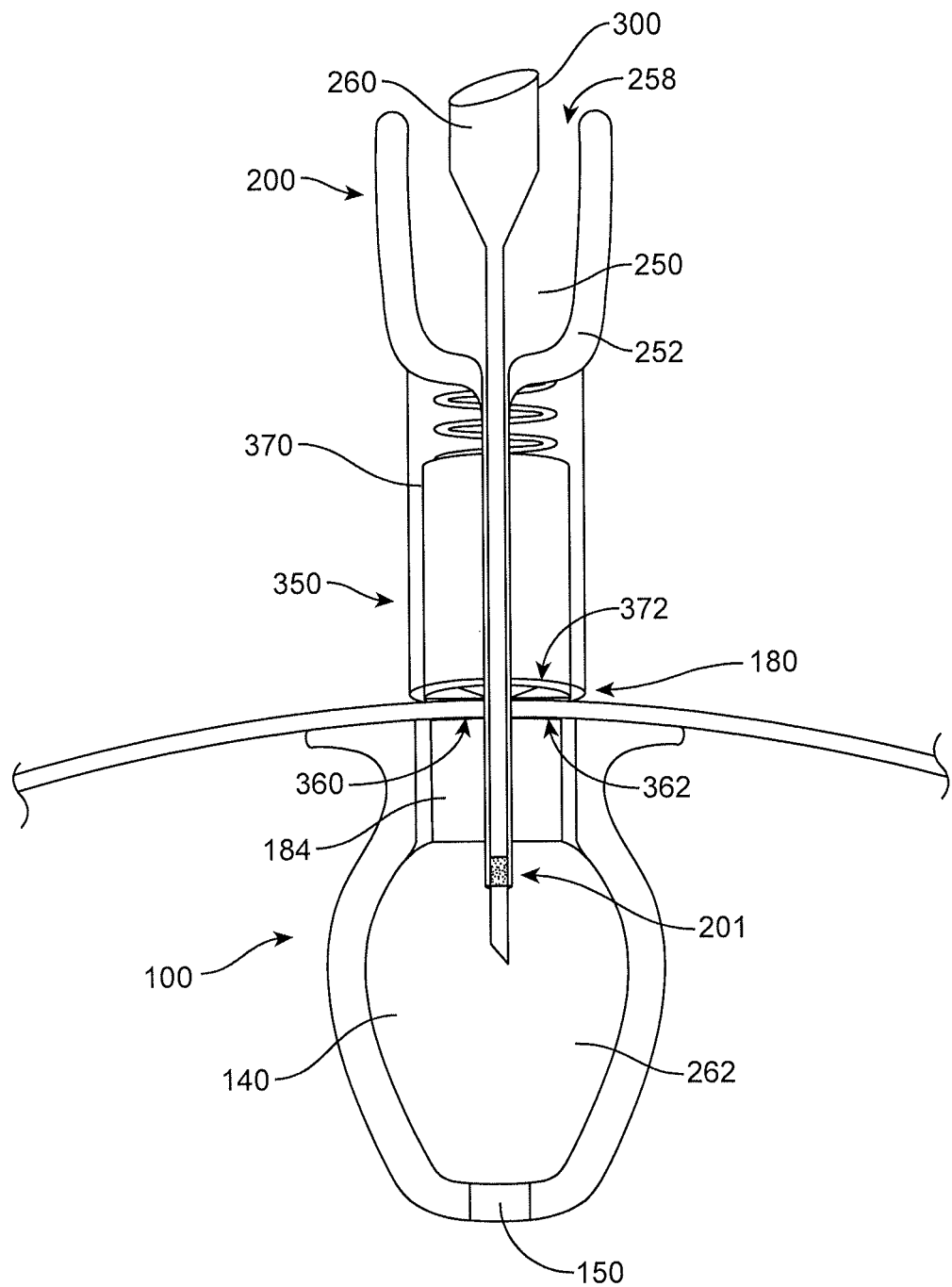
FIG. 8C2

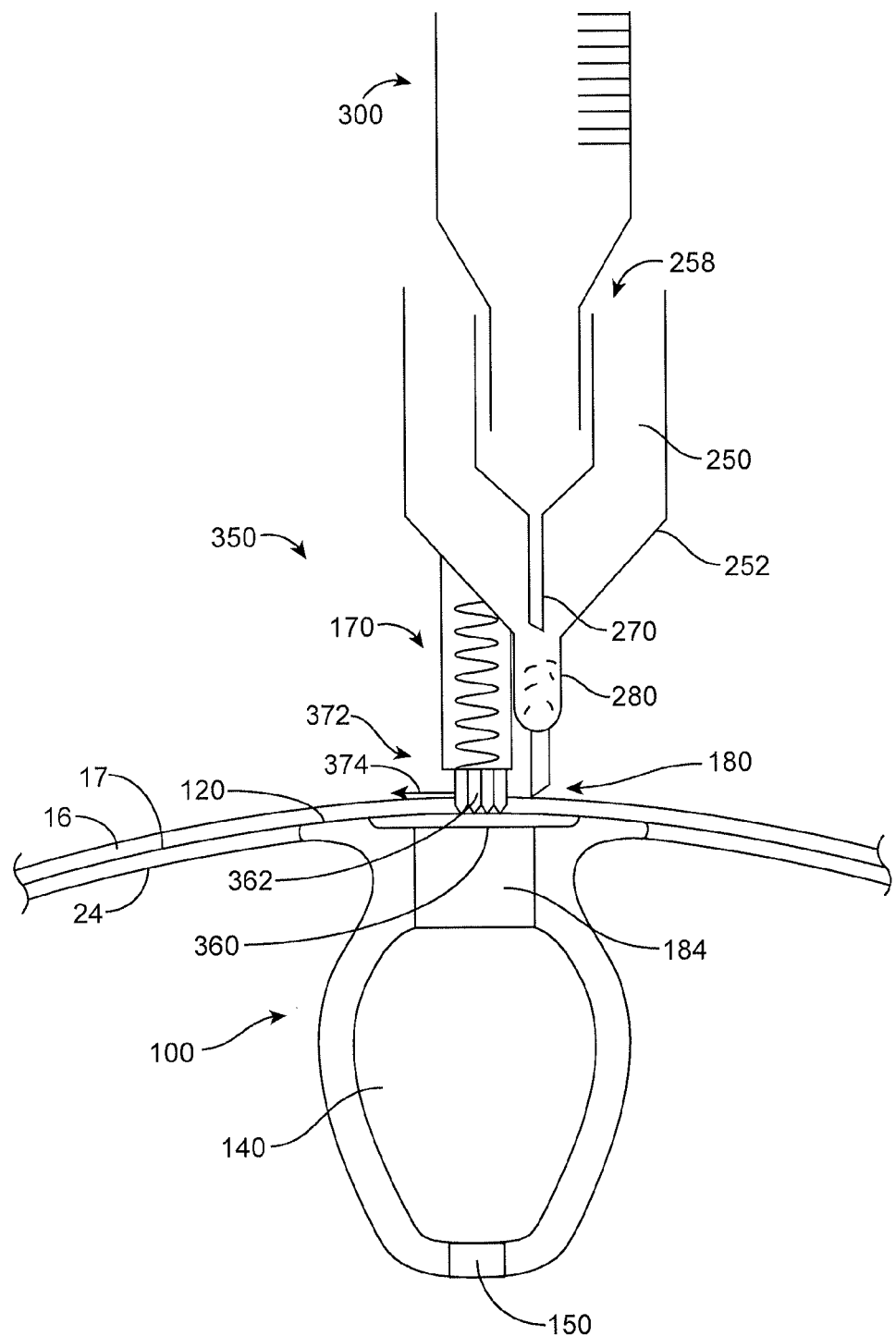
FIG. 8D1

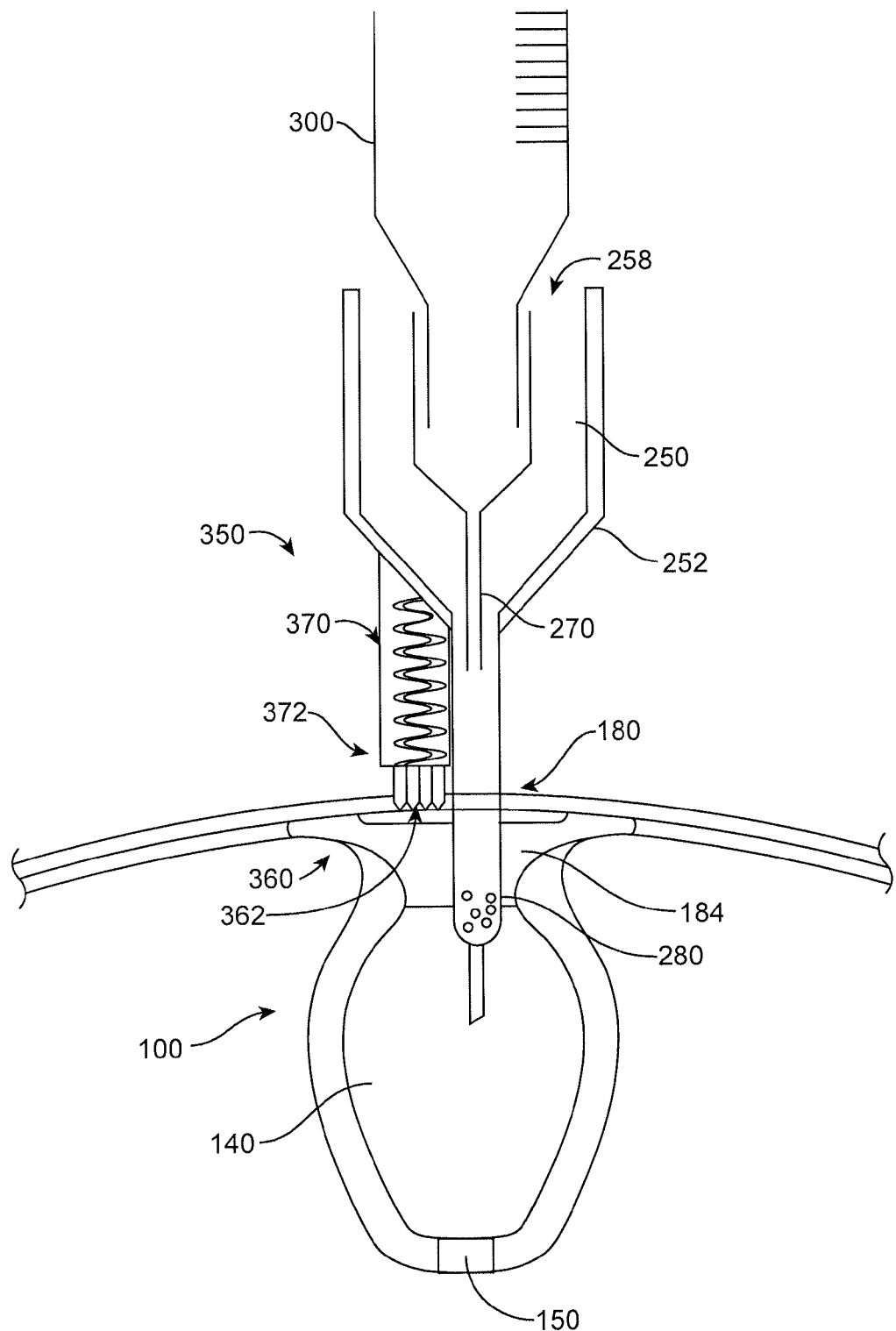
FIG. 8D2

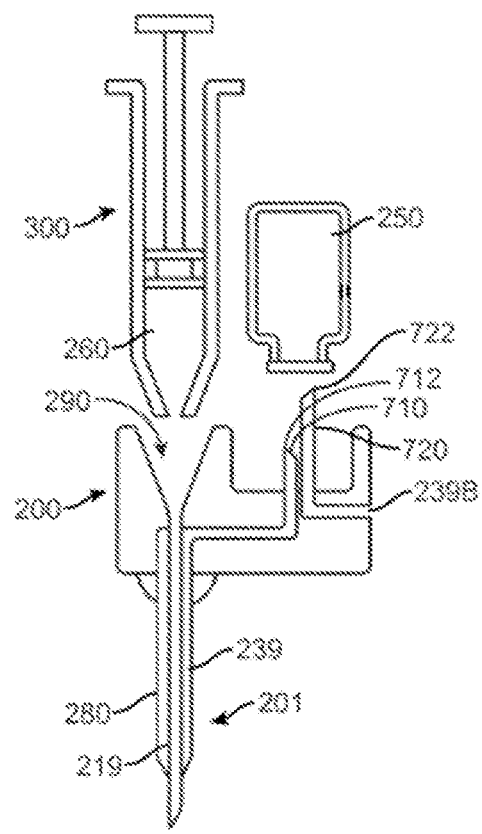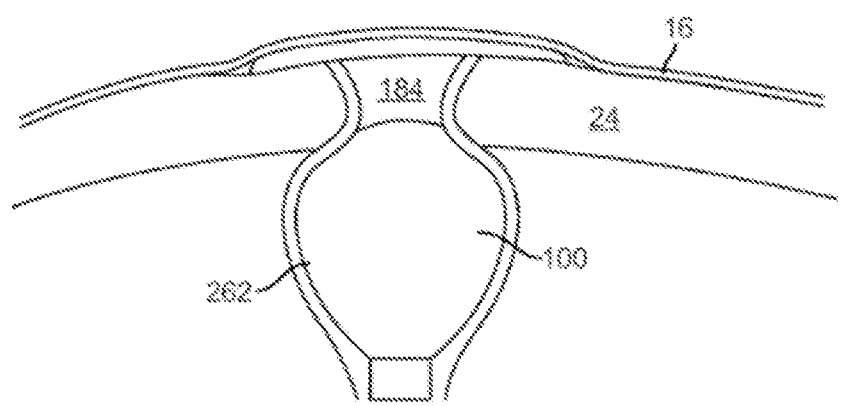
FIG. 17

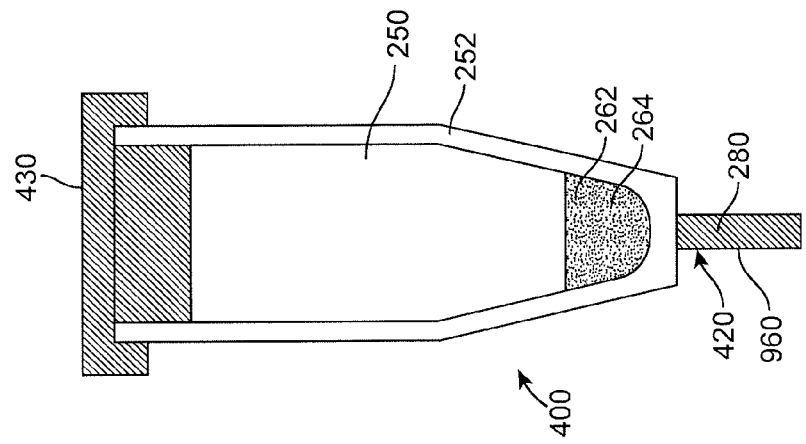
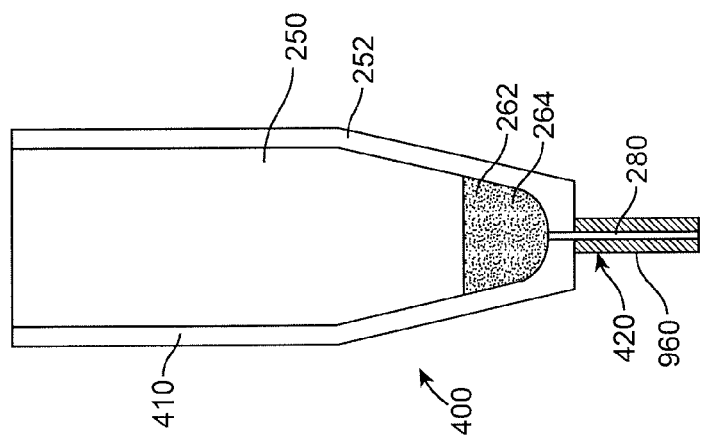
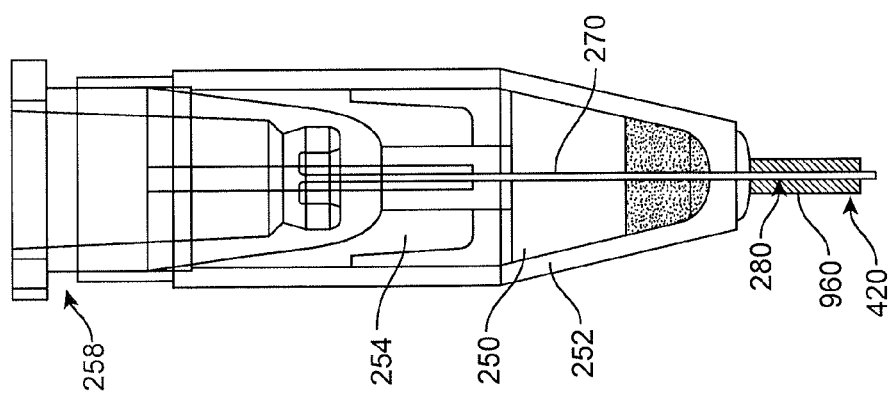
FIG. 25C
FIG. 25B
FIG. 25A

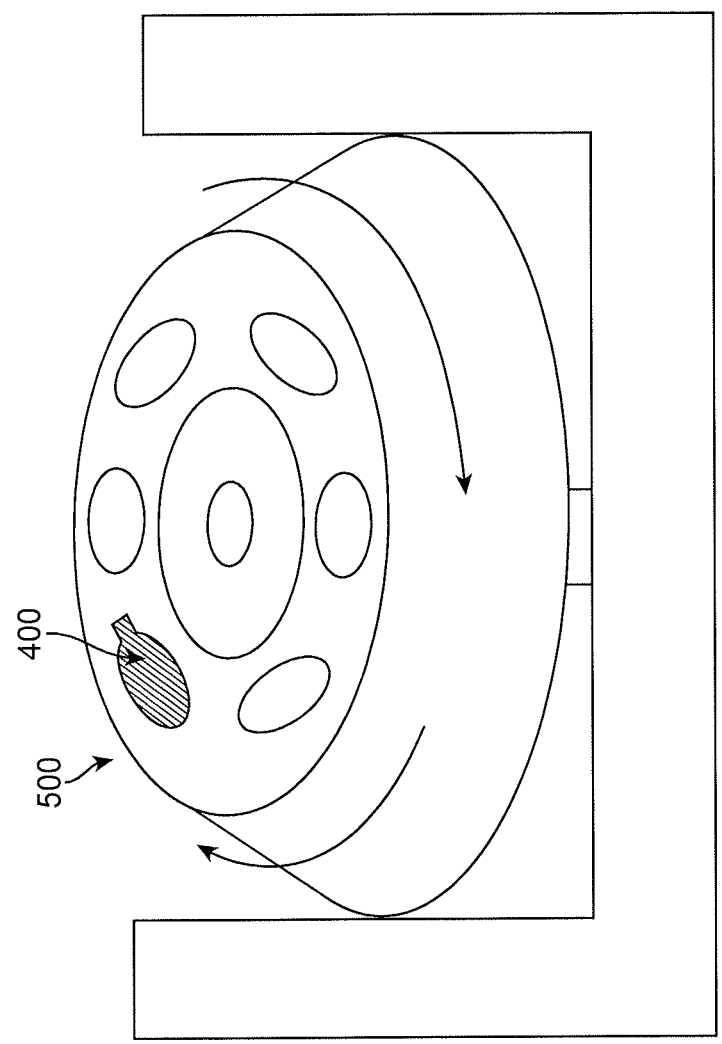

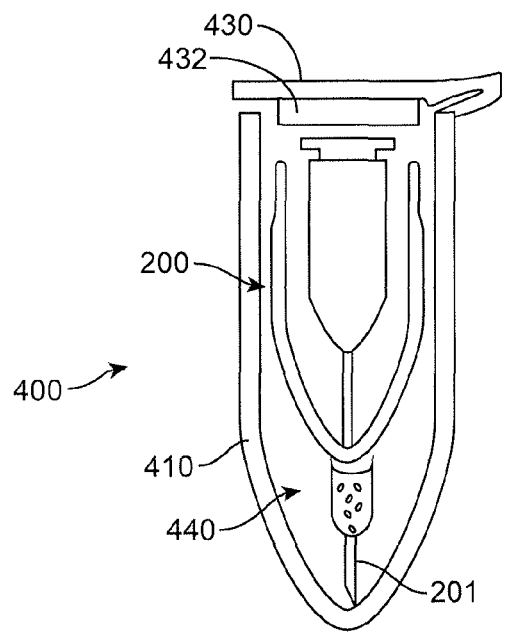
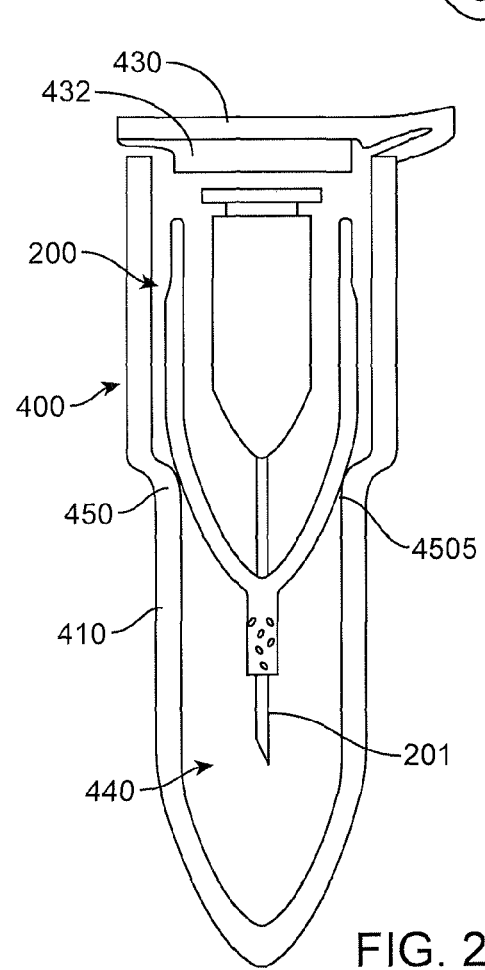
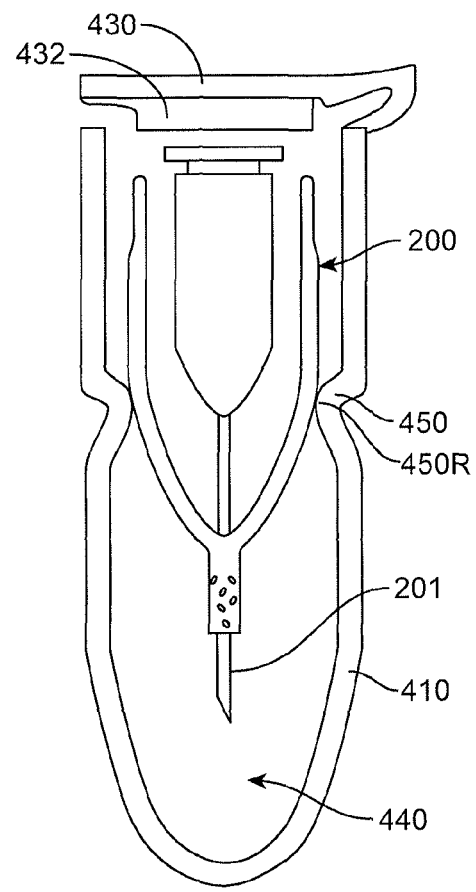
FIG. 26F
FIG. 26G
FIG. 26H

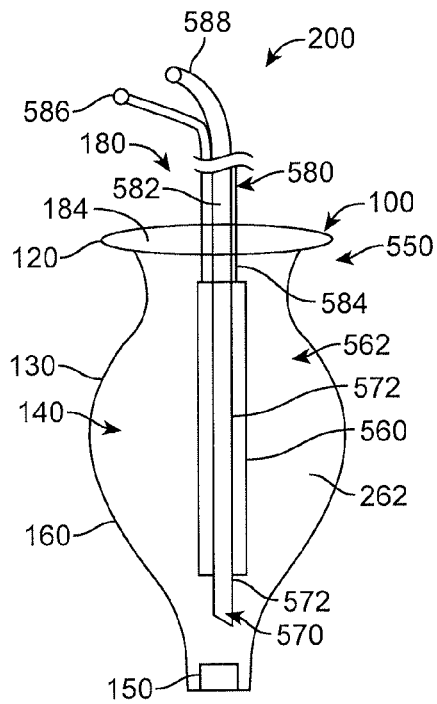
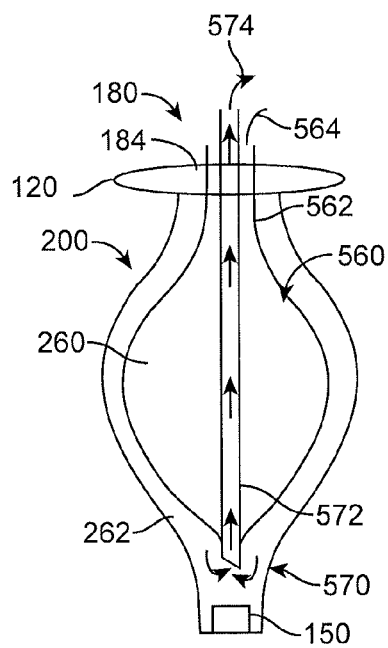
FIG. 28A
FIG. 28B
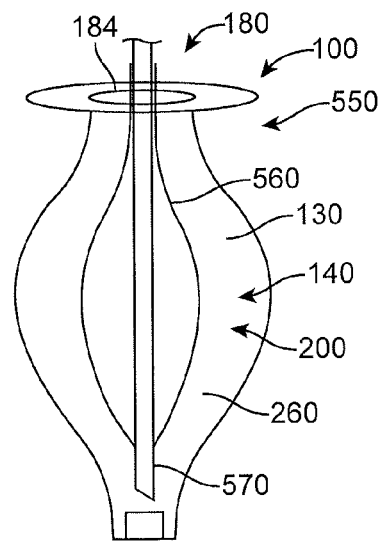
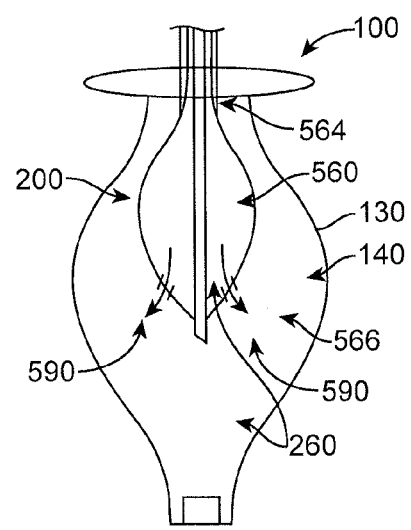
FIG. 28C
FIG. 28D

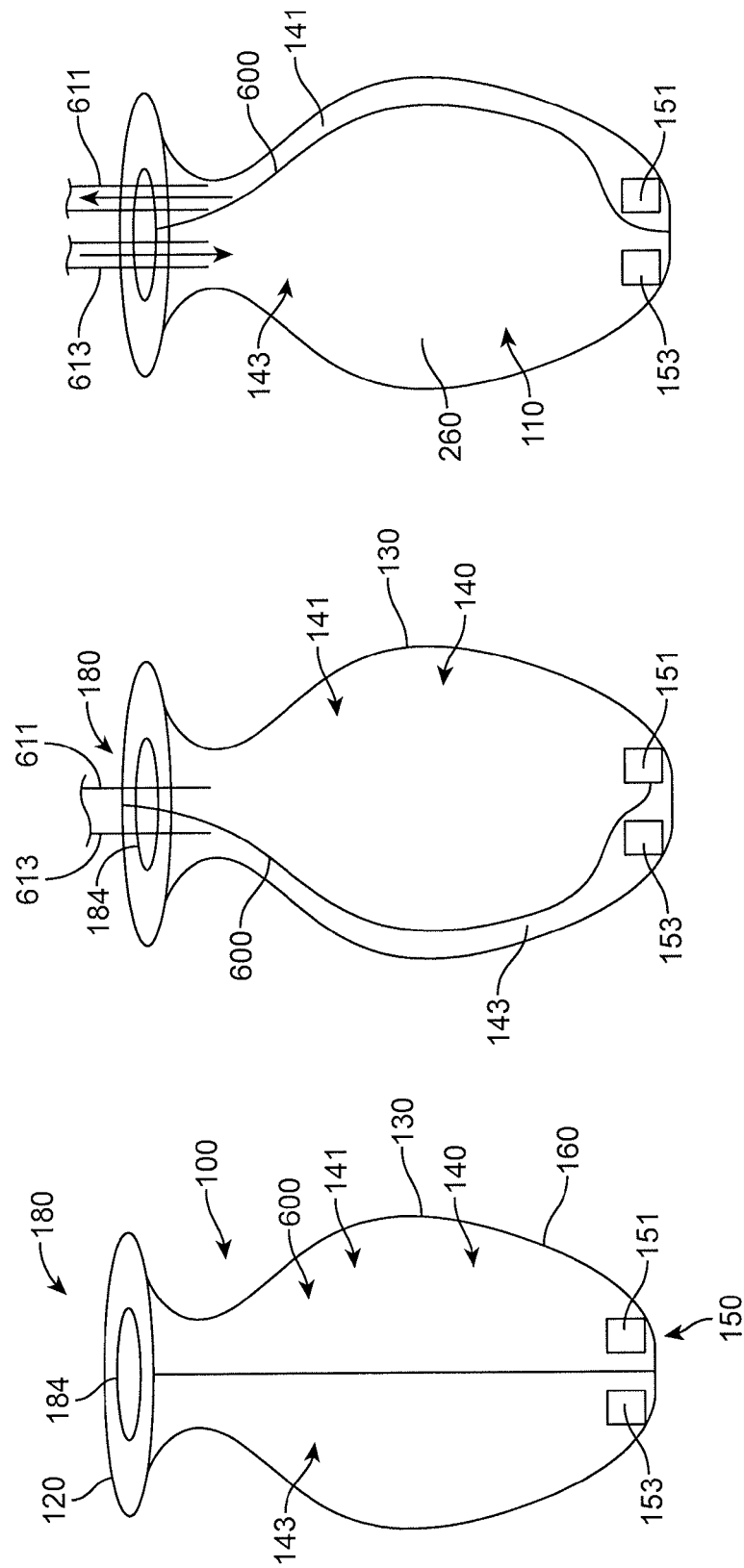

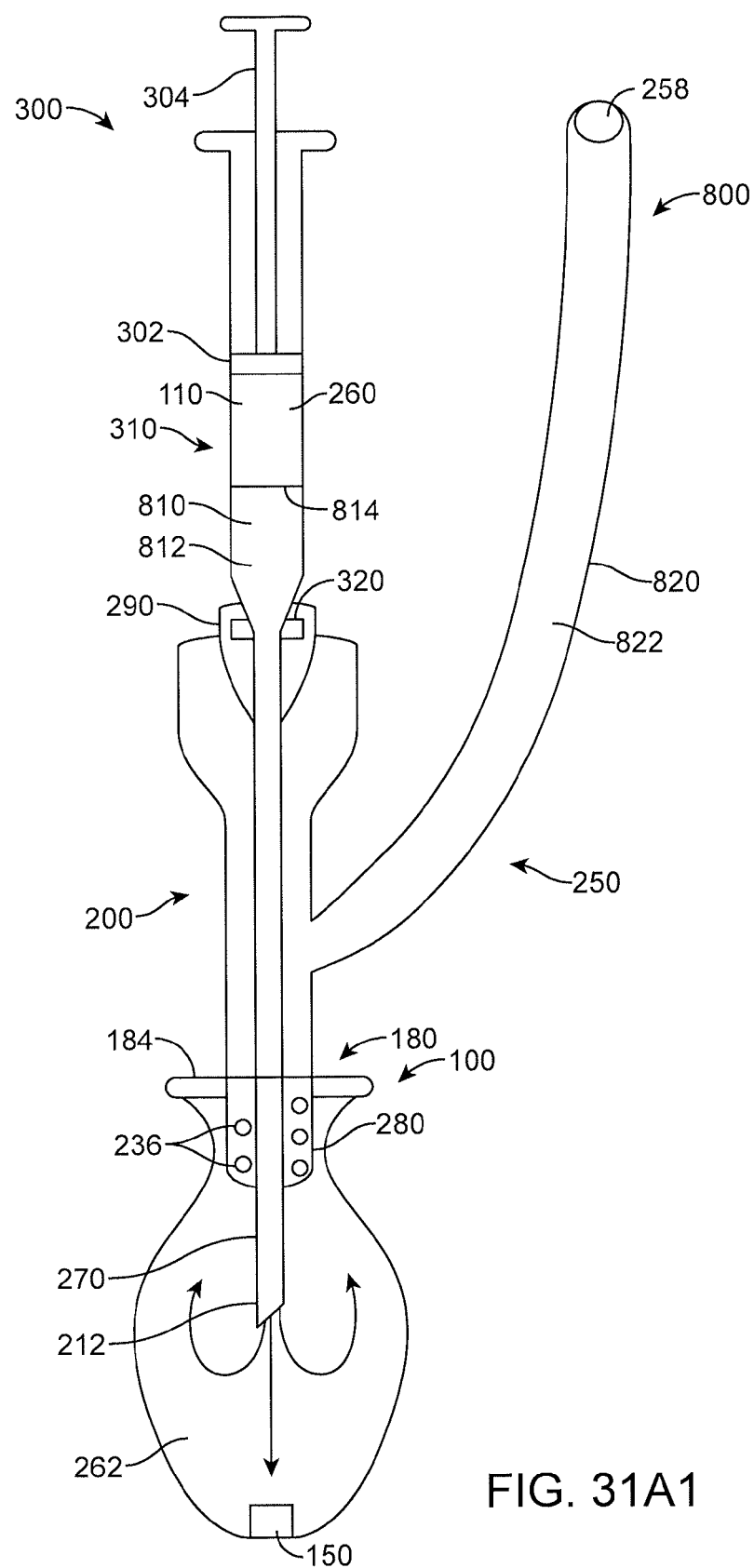
FIG. 31A1

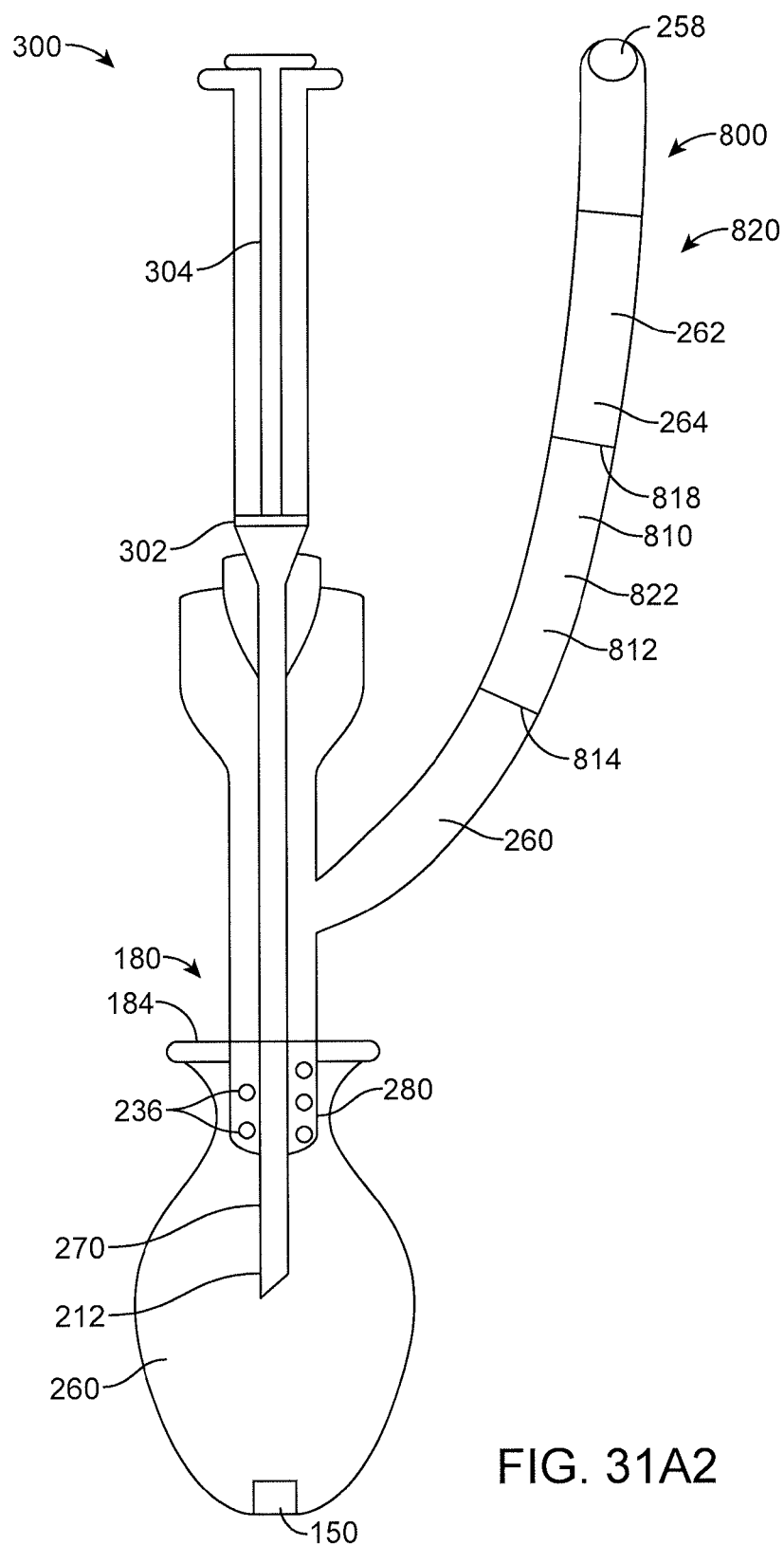
FIG. 31A2

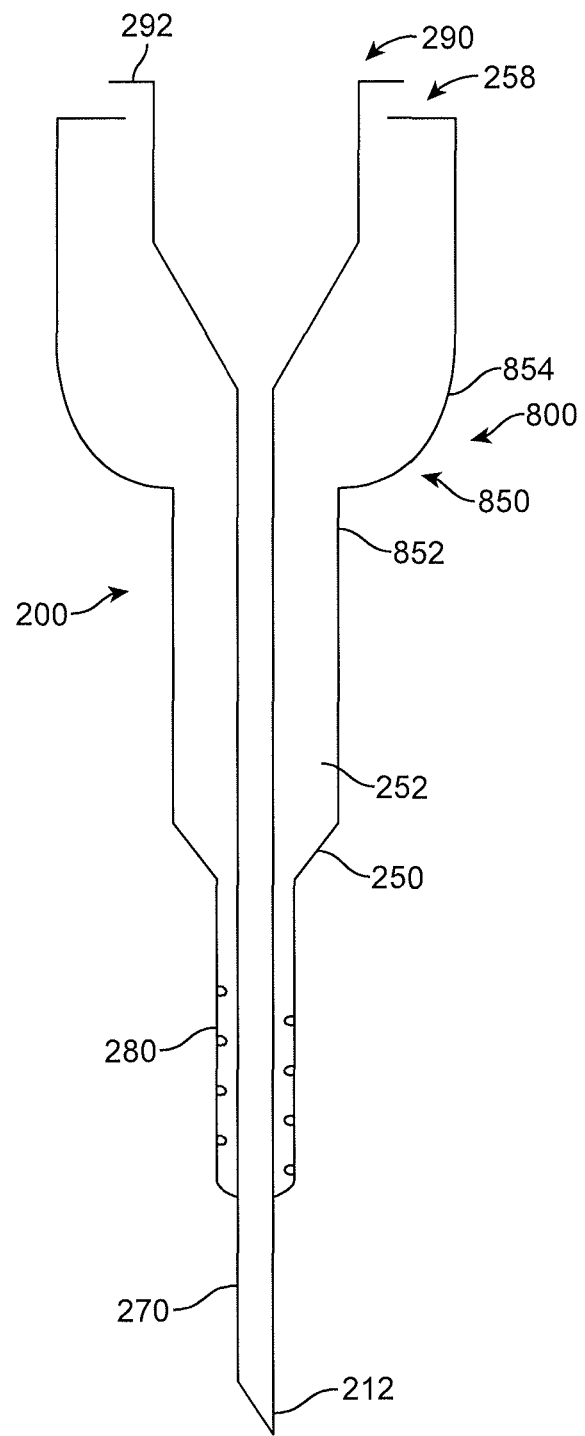
FIG. 31B1

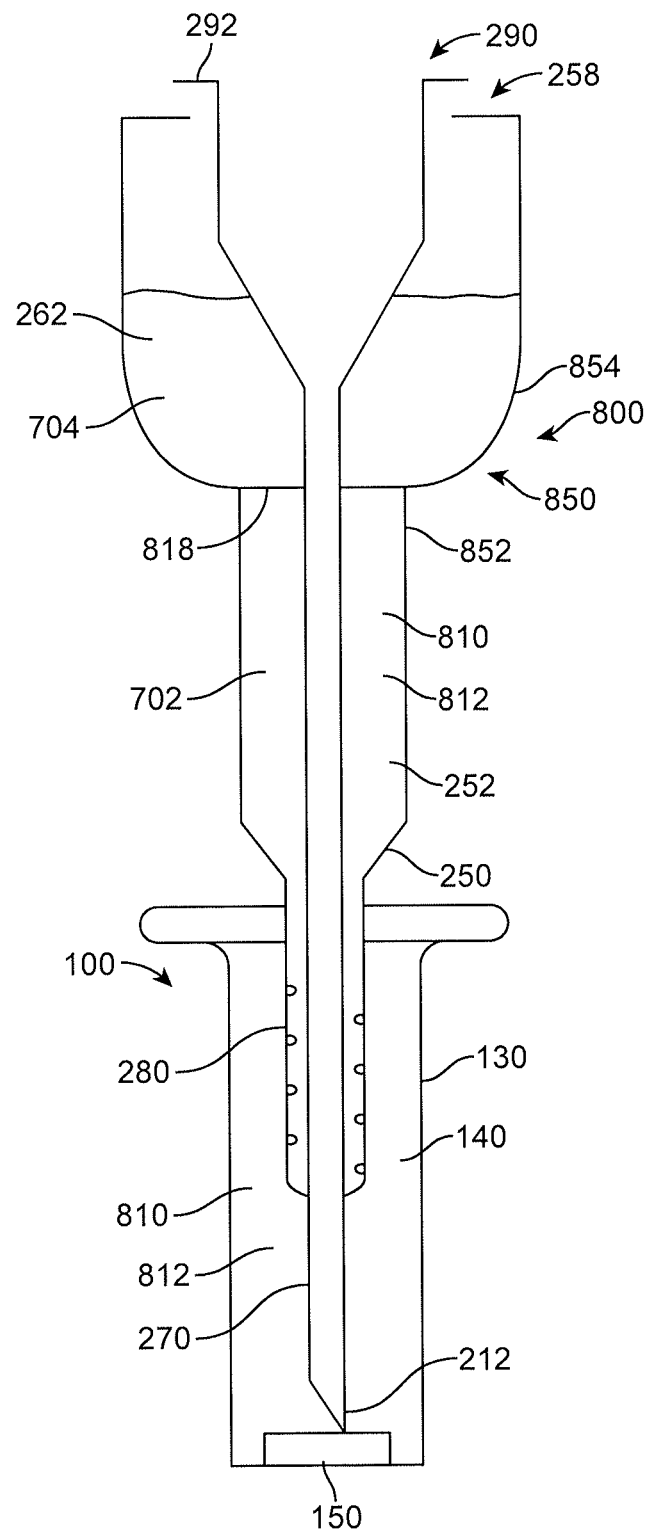
FIG. 31B2

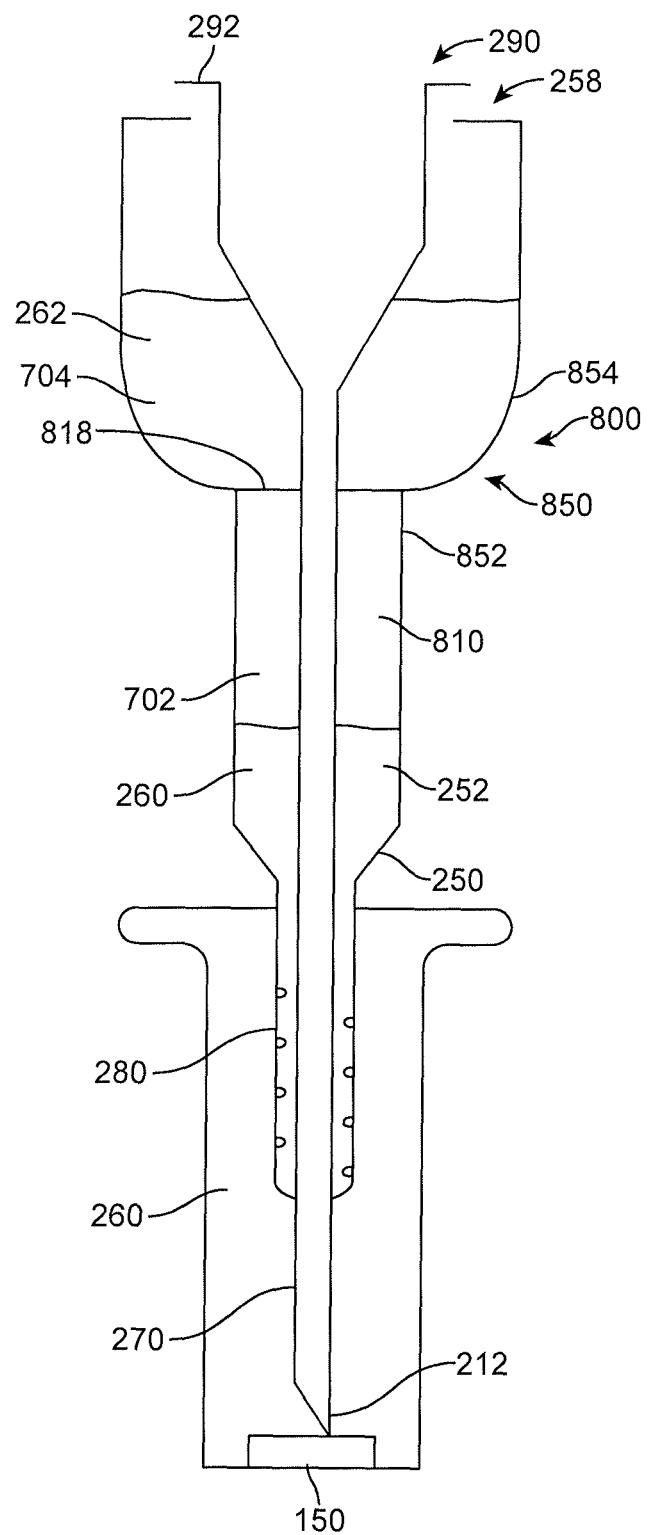
FIG. 31B3

FLUID EXCHANGE APPARATUS AND METHODS

CROSS-REFERENCE TO RELATED APPLICATIONS

This application claims priority of the following U.S. Provisional patent applications: (1) U.S. Provisional Application Ser. No. 61/535,900, titled, "Fluid Exchange Apparatus and Methods," filed on Sep. 16, 2011; and (2) U.S. Provisional Application Ser. No. 61/595,604, titled, "Fluid Exchange Apparatus and Methods," filed on Feb. 6, 2012. The disclosures of the Provisional patent applications are hereby incorporated by reference in their entirety.

BACKGROUND

The present disclosure is generally directed to methods and apparatus to exchange a fluid of an implantable device.

Implantable devices can be used to provide a therapeutic agent to one or more portions of a body of a patient. The implantable device may have a chamber for storing the therapeutic agent, and the agent can be released into the patient to provide a therapeutic benefit. After an amount of time, the amount of fluid release can be less than ideal, and the fluid of the implantable device may be replaced, refilled, or exchanged to provide additional amounts of therapeutic agent to extend the therapy.

Work in relation to embodiments of the present disclosure indicates that the prior methods and apparatus to place a fluid in a device implanted in the body can be less than ideal in at least some instances. For example, the amount of therapeutic fluid placed in an implanted therapeutic device with injection can be less than ideal in at least some instances. The therapeutic fluid placed in the implantable device may mix with a fluid already present in the implantable device, such that the amount of therapeutic fluid placed in the implantable devices can be less than ideal in at least some instances. Also, mixing of the implantable device fluid with the therapeutic fluid during exchange can provide a less than ideal sample of the fluid from the implantable device in at least some instances. At least some of the prior injections may at least partially damage the implantable device, for example with repeated injection of a needle through a septum. Further, as the implantable device may be small, the amount of pressure within a chamber of the implantable device may substantially exceed atmospheric pressure in order to provide a clinically acceptable amount of time to place the therapeutic fluid in the implanted device. In at least some instances the seal between the injector apparatus and implantable therapeutic device may be absent or inadequate and the exchanged fluids may leak from one or more of the injector apparatus or the implantable device in at least some instances.

Refilling devices implanted in the eye may present additional challenges in at least some instances. At least some of the prior devices implanted in the eye can be small to decrease interference with vision, and the refill port of such devices can be small and the eye can move rapidly in at least some instances. Alignment of the injection apparatus with the refill port of the implanted device can be more difficult than would be ideal in at least some instances.

Work in relation to embodiments suggests that at least some prior injector apparatus may be reused among patients, for example needles, and it may be helpful to limit reuse of the injector apparatus.

At least some of the prior methods and apparatus to diagnose a patient have been less than ideal in at least some respects. In at least some instances, the eye disease may have progressed more than would be ideal. Although tissue can be removed from the patient with a biopsy or vitreous humor removed with a vitreal tap, such procedures can be more invasive than would be ideal. It would be helpful to provide methods and apparatus to obtain a sample from a patient that is less invasive than prior methods and apparatus.

SUMMARY

In light of the above, it would be desirable to provide improved treatments for the eye and improved methods and apparatus to place therapeutic fluids in a device implanted in the eye. These treatments and methods and apparatus would decrease at least some of the deficiencies of the prior art, and would provide improved replacement and sampling of a fluid of a device implanted within the body, improved ease of alignment, improved exchange efficiency, little or no leakage resulting from pressure of the injection, and a clinically acceptable exchange time.

Embodiments disclosed herein provide improved methods and apparatus to treat a patient having a device implanted in the body. The apparatus may comprise an exchange apparatus having an elongate structure capable of extending into the implantable device when implanted, and the elongate structure may comprise an opening to place a therapeutic fluid in the implanted device and one or more openings to receive an implantable device fluid from the implantable device. The implantable device may comprise a lock, and the exchange apparatus may comprise a key, so as to limit access to appropriate apparatus and formulations appropriate for the implantable device. The implantable device fluid may comprise air, or a liquid such as saline or a fluid comprising a component of the patient. The elongate structure of the exchange apparatus may comprise a needle and a sheath, in which the sheath extends over a proximal portion of the needle so that the needle and the sheath can be advanced through a penetrable barrier and into a reservoir of the implantable device. The sheath extending over at least a portion of the needle can maintain integrity of the penetrable barrier, and can provide an outflow path having a low resistance to flow so that the fluid within the implantable device can be displaced with decreased pressure. The outflow path can extend from the one or more openings to a receiver container configured to receive the fluid of the implantable device. The implantable device may comprise a porous structure to release therapeutic agent for an extended time. The porous structure may comprise a resistance to fluid flow greater than the resistance to flow of the outflow path from the one or more openings to the receiver container, so that the fluid of the implantable device can be displaced to the receiver container and flow through the porous structure inhibited. The exchange apparatus may comprise a receiver container to receive a sample of the implantable device fluid when the therapeutic fluid is placed in the implantable device. In many embodiments, the exchange apparatus is configured to separate at least a portion of the implantable device fluid from the therapeutic fluid. The separation of at least a portion of the implantable device fluid from the therapeutic fluid can provide a sample of the implantable device fluid useful for analysis and may increase the amount of therapeutic fluid placed in the implantable device.

The one or more openings may comprise a plurality of openings to receive the implantable device fluid. In many embodiments, an injector apparatus comprises an elongate structure having a plurality of openings positionable near a penetrable barrier of the implantable device so as to receive fluid of the implantable device and increase exchange efficiency and decrease refill pressure. The elongate structure may comprise a distal tip to penetrate tissue and the penetrable barrier, and a distal opening near the tip to release therapeutic fluid into the implantable chamber. In many embodiments the distal tip, the distal opening, and the plurality of openings are separated from a stop that engages a tissue of the patient and limits penetration depth such that the distal opening and the plurality of openings are located along an axis of the implantable device so as to increase efficiency of the exchange. A tapered portion of the elongate structure can extend between the distal opening and the plurality of openings so as to stretch a penetrable barrier when the elongate structure is advanced. The plurality of openings can be located away from the tapered portion along a proximal portion so as to maintain integrity of the penetrable barrier and so that leakage can be inhibited. The penetrable barrier can be used repeatedly with pressure for subsequent fluid exchange which can extend the lifetime of the device implanted in the eye. The proximal portion of the elongate structure may comprise an extension without openings extending from the stop to the plurality of openings so as to inhibit leakage through the penetrable barrier and place the plurality of openings away from a proximal side of the penetrable barrier. The extension without openings may extend from the stop to the plurality of openings a distance corresponding substantially to a thickness of the penetrable barrier, such that at least one of the plurality of openings is placed near an inner surface of the penetrable barrier so as to receive fluid near the surface of the penetrable barrier and increase an efficiency of the exchange. The plurality of openings can be distributed along an axis of the elongate structure and may be distributed circumferentially around the elongate structure so as to receive fluid from a plurality of axial and circumferential locations of the reservoir chamber of the implantable device.

The fluid initially within the implantable device may comprise a density less than a therapeutic fluid, and the distal tip and plurality of openings can be configured to at least partially separate the fluid injected through the distal tip from the fluid received through the plurality of openings. The distal opening may be placed below the plurality of openings so as to increase separation and the efficiency of the exchange. The distal opening can be placed below the plurality of openings with a distance from the stop shorter than a length of the implantable device. The distance from the distal opening to the stop may correspond to a length of the reservoir chamber of the implantable device so as to position the distal tip having the opening near a distally located porous structure of the implantable device. In many embodiments the distance from the distal opening to the stop can be no more than about half the distance of the reservoir chamber of the implant so as to facilitate alignment and provide high exchange efficiency with the distal opening placed below the proximal plurality of openings.

In many embodiments, the exchange apparatus comprises one or more structures to separate at least a portion of the implantable device fluid from the therapeutic fluid. The one or more structures may comprise a valve, fluid separator, a separator fluid or combinations thereof. The separator fluid may comprise a fluid miscible with the therapeutic fluid and the implantable device fluid, or a fluid immiscible with the therapeutic fluid and the implantable device fluid such as an immiscible fluid comprising one or more of an oil, a hydrophobic liquid, a gas, or air. The separator fluid can be contained in the fluid separator to inhibit mixing of the implantable device fluid with the therapeutic fluid. The valve may be coupled to a first receiver container and a second receiver container such that a first portion of the implantable device fluid can be placed in the first container without substantial amounts of therapeutic fluid. A second portion of the implantable device fluid mixed with the placed therapeutic fluid can be placed in the second receiver container to inhibit mixing of the therapeutic fluid with the sample contained in the first container. The fluid separator may comprise a structure configured to contain the separator fluid between the implantable device fluid and the therapeutic fluid to inhibit mixing.

While the elongate structure can be configured in many ways, in many embodiments the elongate structure comprises a needle extending from the proximal stop to the distal tip and a sheath placed over the needle to provide the plurality of openings and the tapered intermediate portion. The sheath may comprise a distal portion to engage the needle and an increased cross sectional size to provide the taper. In many embodiments the sheath located over the needle provides one or more channels coupled to the plurality of opening to receive the fluid from the implantable device. The one or more channels may extend proximally from the plurality of openings to a container to receive the fluid from the implantable device.

The exchange apparatus can be coupled to an injector in many ways and may comprise an injector, such as a syringe. In many embodiments the exchange apparatus comprises a connector to couple to a syringe. The connector may comprise a known standard connector, such as a Luer connector, or may comprise a custom connector, such as a keyed connector, to inhibit inappropriate access to the implantable device. The connector may comprise a lock and key mechanism. The connector of the implantable device may comprise a lock and the connector of the syringe may comprise a key to access the exchange apparatus. Alternatively, the injector can be integrated with the exchange apparatus, and the injector may comprise an amount of therapeutic agent to inject into the implantable device.

In many embodiments, the receiver container comprises one or more channels that vent to atmospheric pressure such that a gas within the receiver container can be displaced with fluid comprising liquid from the implantable device. The receiver container may comprise a porous structure that readily allows passage of the gas from the receiver container with a low resistance to flow and substantially inhibits passage of the liquid from the implantable device chamber with a substantially greater resistance to flow. The receiver container may comprise a volume to inhibit re-use of the exchange apparatus, such that the injector apparatus can be a single-use device. The volume of the receiver container may be no more than about twice a volume of the reservoir chamber of the implantable device, for example.

The container of the exchange apparatus can be configured to receive a sample from the implantable device container, and to provide access to the fluid stored in the receiver container. The fluid from the receiver container can be removed from the receiver container for analysis to determine the health of the eye of the patient. The receiver container may comprise a penetrable barrier to access the fluid sample within the receiver container with a needle. The receiver container may be separated from the exchange apparatus to provide the sample from the container. Alternatively or in combination, the receiver container may be pressurized to displace the sample fluid from the reservoir container.

In many embodiments, a sample container can be coupled to the receiver container so as to receive the implantable device fluid from the receiver container. The exchange apparatus may comprise an elongate structure having one or more openings to receive the implantable device fluid, and the implantable device fluid can be displaced from the receiver container so as to pass through the one or more openings and into the sample container. The implantable device fluid can be displaced from the receiver container in many ways. A pressure source or a vacuum source such as a syringe can be coupled to the one or more openings to urge the implantable device fluid from the receiver container to the sample container. The implantable device fluid can be urged, for example drawn, into the sample container with aspiration from the vacuum source comprising the syringe. Alternatively or in combination, the implantable device fluid can be urged, for example pushed, with pressurization of the receiver container, for example from a pressure source comprising a syringe. A channel may extend from the receiver container to an opening that vents to atmospheric pressure during exchange, and the opening can be coupled to the syringe with pressurization subsequent to exchange, such that the channel and receiver container can be pressurized so as to urge fluid from the receiver container through the one or more openings. The receiver container and sample container may be placed in a centrifuge to urge implantable device fluid through the one or more openings onto an inner surface of the sample container. The sample container may comprise a penetrable barrier such as a septum, and the elongate structure may be advanced to place the one or more openings within a chamber of the sample container such that the implantable device fluid can be displaced from the receiver container.

Additional aspects of the present disclosure are recited in the claims below, and can provide additional summary in accordance with embodiments. It is contemplated that the embodiments as described herein and recited in the claims may be combined in many ways, and any one or more of the elements recited in the claims can be combined together in accordance with embodiments of the present disclosure and teachings as described herein.

BRIEF DESCRIPTION OF THE DRAWINGS

FIG. 1 shows an eye suitable for incorporation of the therapeutic device;

FIG. 2 shows a therapeutic device implanted under the conjunctiva and extending through the sclera to release a therapeutic agent into vitreous humor of the eye so as to treat the retina of the eye;

FIG. 3A shows an embodiment of a therapeutic device comprising a container having a penetrable barrier disposed on a first end, a porous structure disposed on a second end to release therapeutic agent for an extended time;

FIG. 3B shows an embodiment of a porous structure comprising a plurality of channels extending substantially straight through a disk;

FIG. 7A shows an embodiment of an exchange apparatus comprising a locking connector to couple to a syringe;

FIG. 7B shows an embodiment of an elongate structure and receiver container of the exchange apparatus of FIG. 7A;

FIG. 7C shows embodiments of sheaths suitable for combination with the exchange apparatus of FIGS. 7A and 7B;

FIG. 7D shows an embodiment of a sheath opening having a beveled channel surface to inhibit degradation of the penetrable barrier;

FIG. 7E shows an embodiment of a sheath opening having a rounded channel surface and edge to inhibit degradation of the penetrable barrier;

FIG. 8B1 shows an embodiment of a deflectable elongate structure in an unloaded configuration prior to insertion in the lock of FIG. 8B;

FIG. 8B2 shows an embodiment of a deflected elongate structure in an unloaded configuration prior to insertion in the lock of FIG. 8B;

FIG. 8C1 shows an embodiment of an implantable therapeutic device comprising a lock and an exchange apparatus comprising a rotatable key to the lock;

FIG. 8C2 shows an embodiment of an implantable therapeutic device of FIG. 8C1 in a locked configuration in which the elongate structure extends through the open lock to access the reservoir chamber of the implantable device;

FIG. 8D1 shows an embodiment of an implantable therapeutic device comprising a lock and an exchange apparatus comprising a slidable key to the lock;

FIG. 8D2 shows an embodiment of an implantable therapeutic device of FIG. 8D1 in a locked configuration in which the elongate structure extends through the open lock to access the reservoir chamber of the implantable device;

FIG. 17 shows an embodiment of an exchange apparatus coupled to a removable receiver container;

FIG. 25A shows an embodiment of an exchange apparatus comprising a removable receiver container comprising a removable sheath placed over a needle;

FIG. 25B shows an embodiment of the removable container of FIG. 25A with a plug placed over the sheath and the needle removed;

FIG. 25C shows an embodiment of the removable container of FIGS. 25A and 25B with a plug placed over the sheath and a cap over the removable receiver container;

FIGS. 26A, 26B, 26C, 26D and 26E show an embodiment of a centrifuge used to remove the fluid sample from the receiver container of the exchange apparatus;

FIG. 26F shows an embodiment comprising an exchange apparatus placed in a sample container comprising a centrifuge tube;

FIG. 26G shows an embodiment comprising an exchange apparatus placed in a sample container comprising a centrifuge tube, in which the centrifuge tube comprises a support comprising a narrow shoulder portion of the tube to hold the exchange apparatus;

FIG. 26H shows an embodiment comprising an exchange apparatus placed in a sample container comprising a centrifuge tube, in which the centrifuge tube comprises a support comprising restricted portion to hold the exchange apparatus;

FIG. 28A shows an embodiment of an exchange apparatus comprising a balloon supported on an elongate tubular member capable of introduction into an implantable therapeutic device to exchange the implantable device fluid with a therapeutic fluid;

FIG. 28B shows an embodiment of the balloon as in FIG. 28A inflated within the therapeutic device to displace the implantable device fluid;

FIG. 28C shows an embodiment of the balloon deflated within the therapeutic device to provide space for the therapeutic fluid;

FIG. 28D shows an embodiment of the balloon punctured within the therapeutic device to release the therapeutic fluid from the balloon to the reservoir chamber of the therapeutic device;

FIG. 29A shows an embodiment of a deflectable fluid separator placed within an implantable therapeutic device;

FIG. 29B shows an embodiment of the deflectable fluid separator as in FIG. 29A displaced to a second side of the reservoir chamber to remove fluid from the second side of the reservoir chamber;

FIG. 29C shows an embodiment of the deflectable fluid separator as in FIG. 29B displaced to a first side of the reservoir chamber with the therapeutic fluid placed in the second side;

FIG. 31A1 shows an embodiment of an exchange apparatus having a fluid separator comprising an internal channel sized to support the implantable device fluid with a pocket of air;

FIG. 31A2 shows an embodiment of the exchange apparatus of FIG. 31A1 having the implantable device fluid supported with a pocket of air to separate the implantable device fluid from the therapeutic fluid;

FIG. 31B1 shows an embodiment of an exchange apparatus having a fluid separator comprising an internal channel having a first portion sized to support the implantable device fluid with a pocket of air and a second portion sized to pass air through the implantable device fluid;

FIG. 31B2 shows an embodiment of the exchange apparatus of FIG. 31B1 having the first portion supporting the implantable device fluid contained in the second portion with the pocket of air within the first portion;

FIG. 31B3 shows an embodiment of the exchange apparatus of FIGS. 31B1 and 31B2 having the first portion supporting the implantable device fluid with the pocket of air and therapeutic fluid;

DETAILED DESCRIPTION

Figure 3:
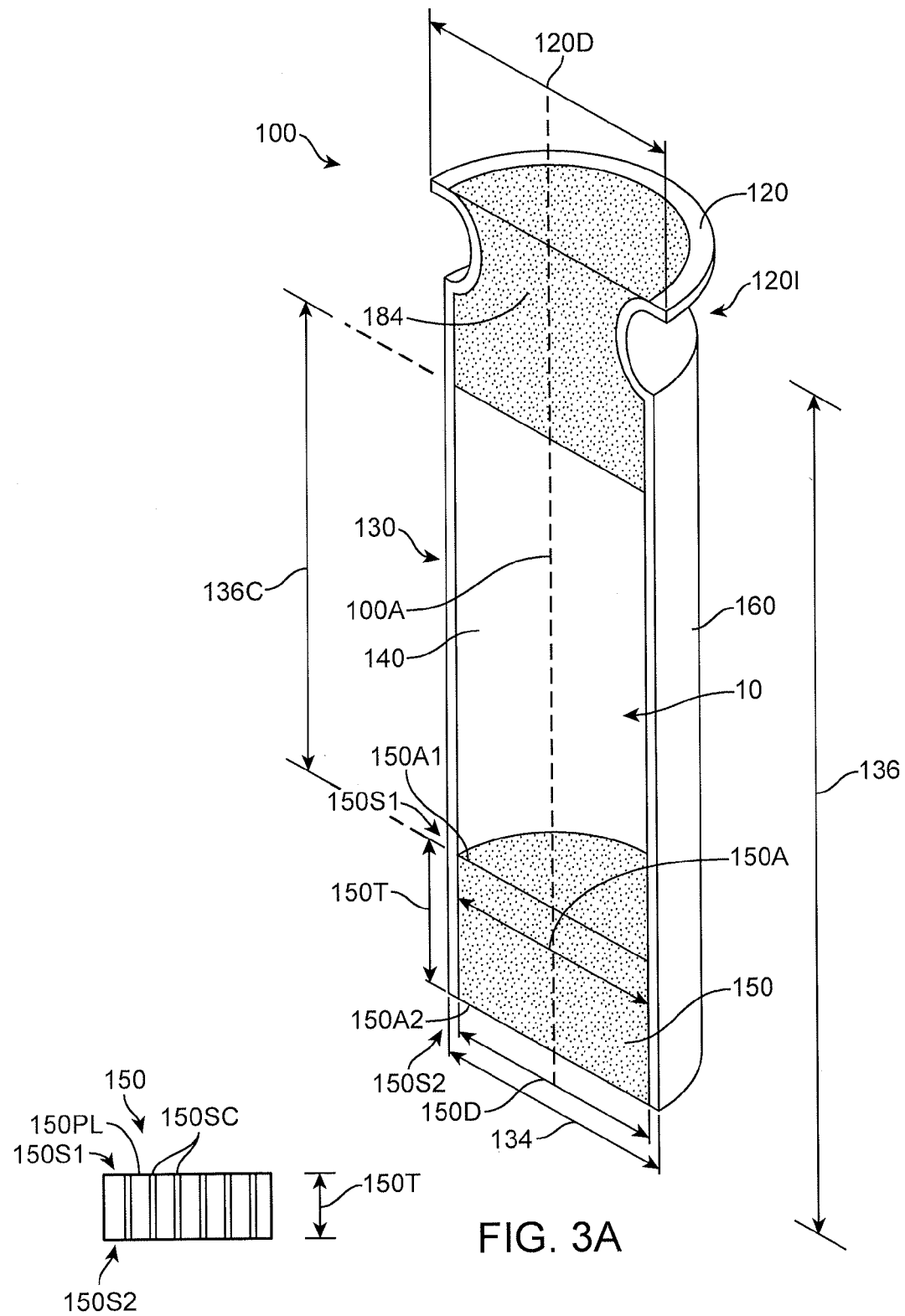

Embodiments of the present disclosure as described herein can be combined in many ways to treat one or more diseases of a patient such as a disease of the eye. The embodiments as described herein are well suited to treat patients with a therapeutic agent for an extended time, such as may be provided with a device that can be at least partially implanted into the eye. Although specific reference is made to ophthalmic treatment of the eye, the methods and apparatus to place a therapeutic fluid in implantable device can be used with many implantable devices and treatments of one or more of many diseases, such as systemic medication to treat systemic disease, orthopedic treatment to treat orthopedic disorders, or dental treatment, for example. The exchange apparatus and methods as described herein are well suited for use with many drug delivery devices, such as refillable diffusion based devices, and can be exceptionally well suited for diffusion devices having a porous drug release structure configured for extended release in which the porous structure inhibits flow of fluid during exchange.

The exchange apparatus and methods as described herein are well suited for diagnoses and treatment of the eye, for example with diagnosis and treatment of the eye based on the implantable device fluid received with the exchange apparatus with the fluid is injected. The implantable device can be combined with one or more known methods of analysis of biomarkers, for example commercially available beads and arrays to detect and measure biomarkers. The methods and apparatus as described herein are well suited for combination with analysis of samples as described in U.S. Pat. App. Ser. No. 61/538,736, entitled "Diagnostic Methods and Apparatus", Filed: Sep. 23, 2011, the full disclosure of which is incorporated herein by reference. Examples of injector apparatus, therapeutic devices, valves and mechanisms to provide the bolus injection are described in U.S. patent application Ser. No. 12/696,678, filed on Jan. 29, 2010, entitled "Posterior Segment Drug Delivery", Publication No. 2010/0255061; and U.S. PCT Pat. App. No. PCT/US2011/046812, filed Aug. 5, 2011, entitled "Injector Apparatus and Method for Drug Delivery", the entire disclosures of which are incorporated herein by reference. PCT Patent Application No. PCT/US2012/049654, filed Aug. 3, 2012 entitled "Small Molecule Delivery with Implantable Therapeutic Device" is also incorporated herein by reference in its entirety.

As used herein like numerals and/or letters denote like elements in the drawings and text as will be apparent to a person of ordinary skill in the art.

FIG. 1 shows an eye 10 suitable for incorporation of the therapeutic device. The eye has a cornea 12 and a lens 22 configured to form an image on the retina 26. The cornea extends to a limbus 14 of the eye, and the limbus connects to a sclera 24 of the eye. A conjunctiva 16 of the eye is disposed over the sclera 24. A Tenon's capsule 17 extends between the conjunctiva 16 and the sclera 24. The lens can accommodate to focus on an object seen by the patient. The eye has an iris 18 that may expand and contract in response to light.

The eye also comprises a choroid 28 disposed between the sclera 24 and the retina 26. The retina comprises the macula 32. The eye comprises a pars plana, which comprises an example of a region of the eye suitable for placement and retention, for example anchoring, of the therapeutic device as described herein. The pars plana region may comprise sclera 24 and conjunctiva 16 disposed between the retina 26 and cornea 12. The therapeutic device can be positioned so as to extend from the pars plana region into the vitreous humor 30 to release the therapeutic agent. The therapeutic agent can be released into the vitreous humor 30, such that the therapeutic agent arrives at the retina 26 and choroid 28 for therapeutic effect on the macula 32. The vitreous humor of the eye 30 comprises a liquid disposed between the lens 22 and the retina 26. The vitreous humor 30 may comprise convection currents to deliver the therapeutic agent to the macula 32.

FIG. 2 shows a therapeutic device 100 implanted under the conjunctiva 16 and extending through the sclera 24. FIG. 3A shows an exemplary embodiment of the therapeutic device 100. The device 100 is configured to release a therapeutic agent 110 into vitreous humor 30 of the eye 10 so as to treat the retina of the eye. The therapeutic device 100 may comprise a retention structure 120 such as a smooth protrusion configured for placement along the sclera 24 and under the conjunctiva 16, such that the conjunctiva 16 can cover and protect the therapeutic device 100. When the therapeutic agent 110 is inserted into the device 100, the conjunctiva 16 may be lifted away, incised, or punctured with a needle to access the therapeutic device 100. The eye 10 may comprise an insertion of the tendon of the superior rectus muscle to couple the sclera of the eye to the superior rectus muscle. The device 100 may be positioned in many locations of the pars plana region, for example away from tendon and one or more of posterior to the tendon, anterior to the tendon, under the tendon, or with nasal or temporal placement of the therapeutic device.

While the implant can be positioned in the eye in many ways, work in relation to embodiments suggests that placement in the pars plana region 25 can release therapeutic agent into the vitreous 30 to treat the retina 26, for example therapeutic agent comprising an active ingredient composed of large molecules.

Therapeutic agents 110 suitable for use with device 100 include many therapeutic agents, for example as listed in Table 1A, herein below. The therapeutic agent 110 of device 100 may comprise one or more of an active ingredient of the therapeutic agent, such as a formulation of the therapeutic agent, a commercially available formulation of the therapeutic agent, a physician prepared formulation of therapeutic agent, a pharmacist prepared formulation of the therapeutic agent, or a commercially available formulation of therapeutic agent having an excipient. The therapeutic agent may be referred to with generic name or a trade name, for example as shown in Table 1A.

The therapeutic device 100 can be implanted in the eye to treat the eye for as long as is helpful and beneficial to the patient. For example the device can be implanted for at least about 5 years, such as permanently for the life of the patient. Alternatively or in combination, the device can be removed when no longer helpful or beneficial for treatment of the patient.

The therapeutic agent 110 can be placed in the therapeutic device 100 in many ways. In many embodiments, a therapeutic fluid 260 (FIG. 2) comprising therapeutic agent 110 is exchanged with an implantable device fluid 262 contained within therapeutic device 100, as shown in FIG. 2. An exchange apparatus 200 can be configured to place the therapeutic fluid 260 and to receive the implantable device fluid displaced from the implantable device when the therapeutic fluid is placed.

With reference to FIG. 2, an exemplary embodiment of the exchange apparatus 200 comprises an elongate structure 201 that can be placed substantially within the implantable device. The elongate structure 201 comprises an opening to place the therapeutic fluid in the reservoir chamber of the implantable device and one or more openings to receive the implantable device fluid from the reservoir chamber. The exchange apparatus 200 may comprise the therapeutic fluid 260 and the receiver container 250 to receive fluid 262 of the implantable device. The therapeutic device 100 may comprise a reservoir chamber to store an amount of the therapeutic agent 110. The reservoir chamber may comprise a fluid 262 of the implantable device 100. The fluid 262 of the implantable device can be displaced when the therapeutic fluid 260 is injected, for example, and a receiver container 250 can be provided to receive the implantable fluid 262 from the implantable device. The reservoir chamber of the implantable device may comprise a substantially rigid walls and a substantially fixed volume, for example.

The exchange apparatus 200 can be configured in many ways, and may be coupled to a syringe 300 with one or more of many connectors, such as a Luer connector, a Luer-Lok™ connector, for example. Alternatively or in combination, the exchange apparatus may comprise syringe 300, for example. The exchange apparatus 200 may comprise an elongate structure 201 to for insertion into the reservoir chamber of the implantable device, and a stop 240 to limit a depth of insertion of the elongate structure 201 into the reservoir chamber of the implantable device. The exchange apparatus 200 may comprise a receiver container 250 to receive the implantable device fluid from the reservoir chamber of the implantable device, and the elongate structure may comprise a plurality of openings coupled to the receiver container so as to receive the fluid of the implantable device through the plurality of openings when the fluid is injected. Alternatively, the therapeutic fluid may be drawn into the reservoir chamber of the implantable device with aspiration of the implantable device fluid into chamber 310 of the syringe, such that the therapeutic fluid placed in chamber 250 can be drawn into the reservoir chamber of the implantable device, for example.

FIG. 3A shows a therapeutic device 100 comprising a container 130 having a penetrable barrier 184 disposed on a first end, a porous structure 150 disposed on a second end to release therapeutic agent for an extended period, and a retention structure 120 comprising an extension protruding outward from the container to couple to the sclera and the conjunctiva. The container 130 may comprise an axis 100A. The inner surfaces of the container 130 may define a reservoir chamber having a volume sized to provide therapeutic amounts of the therapeutic agent for the extended time. The extending protrusion of the retention structure may comprise a diameter 120D. The retention structure may comprise an indentation 120I sized to receive the sclera.

The container may comprise a tubular barrier 160 that defines at least a portion of the reservoir, and the container may comprise a width, for example a diameter 134. The diameter 134 can be sized within a range, for example within a range from about 0.5 to about 4 mm, for example within a range from about 1 to 3 mm and can be about 2 mm, for example. The container may comprise a length 136 sized so as to extend from the conjunctive to the vitreous along axis 100A to release the therapeutic agent into the vitreous. The length 136 can be sized within a range, for example within a range from about 2 to about 14 mm, for example within a range from about 4 to 10 mm and can be about 7 mm, for example. The volume of the reservoir may be substantially determined by an inner cross sectional area of the tubular structure and distance from the porous structure to the penetrable barrier. The retention structure may comprise an annular extension having a retention structure diameter greater than a diameter of the container. The retention structure may comprise an indentation configured to receive the sclera when the extension extends between the sclera and the conjunctive. The penetrable barrier may comprise a septum disposed on a proximal end of the container, in which the septum comprises a barrier that can be penetrated with a sharp object such as a needle for injection of the therapeutic agent. The porous structure may comprise a cross sectional area 150A sized to release the therapeutic agent for the extended period.

The porous structure 150 may comprise a control release mechanism. The porous structure 150 can be configured in many ways to provide controlled sustained release, for example with a release rate index, or a size and number of openings, for example. The porous structure 150 may comprise a first side 150S1 coupled to the reservoir and a second side 150S2 to couple to the vitreous. The first side may comprise a first area 150A1 and the second side may comprise a second area 150A2. The porous structure may comprise a thickness 105T. The porous structure many comprise a diameter 150D.

The porous structure 150 may comprise one or more of a release control element, a release control mechanism, permeable membrane, a semipermeable membrane, a material having at least one hole disposed therein, channels formed in a rigid material, straight channels, nano-channels, nano-channels etched in a rigid material, laser drilled holes, laser etched nano-channels, a capillary channel, a plurality of capillary channels, one or more tortuous channels, sintered material, sintered rigid material, sintered glass, sintered ceramic, sintered metal, tortuous micro-channels, sintered nano-particles, an open cell foam or a hydrogel such as an open cell hydrogel. Additional examples of porous structures are described in U.S. patent application Ser. No. 12/696,678, filed on Jan. 29, 2010, entitled "Posterior Segment Drug Delivery", Publication No. 2010/0255061; and U.S. PCT Pat. App. No. PCT/US2011/046812, filed Aug. 5, 2011, entitled "Injector Apparatus and Method for Drug Delivery", the entire disclosures of which have been previously incorporated herein by reference.

The volume of the reservoir chamber may comprise from about 5 µL to about 2000 µL of therapeutic agent, or for example from about 10 µL to about 200 µL of therapeutic agent. The reservoir may comprise an axial length 136C extending between the penetrable barrier 184 and the porous structure 150.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. For example, reservoir may comprise a suspension of a corticosteroid such as triamcinolone acetonide to treat inflammation of the retina. The reservoir may comprise a buffer and a suspension of a therapeutic agent comprising solubility within a range from about 1 µg/mL to about 100 µg/mL, such as from about 1 µg/mL to about 40 µg/mL. For example, the therapeutic agent may comprise a suspension of triamcinolone acetonide having a solubility of approximately 19 µg/mL in the buffer at 37° C. when implanted.

The release rate index may comprise many values, and the release rate index with the suspension may be somewhat higher than for a solution in many embodiments, for example. The release rate index may be no more than about 5, and can be no more than about 2.0, for example no more than about 1.5, and in many embodiments may be no more than about 1.2, so as to release the therapeutic agent with therapeutic amounts for the extended time. The release rate index can be at about 0.01, for example.

The therapeutic device, including for example, the retention structure and the porous structure, may be sized to pass through a lumen of a catheter.

The porous structure may comprise a needle stop that limits penetration of the needle. The porous structure may comprise a plurality of channels configured for the extended release of the therapeutic agent. The porous structure may comprise a rigid sintered material having characteristics suitable for the sustained release of the material.

FIG. 3B shows a porous structure comprising a plurality of substantially straight channels 150SC extending substantially straight through a disk. The channels 150SC can extend from a first side 150S1 to a second side 150S2 a distance comprising thickness 150T of the porous structure. Each of the channels comprises a cross-sectional dimension across, for example a diameter, and a corresponding area across the cross section. The combined cross-sectional area of the plurality of channels, the thickness 150T, the diffusion coefficient of the therapeutic agent, the concentration of therapeutic agent within the reservoir chamber and the volume of the reservoir chamber determine substantially the release rate profile of the therapeutic agent. The size and number of the plurality of channels 150SC and thickness of the porous structure can be configured so as to provide the release rate profile.

The porous structure 150 may comprise the control release mechanism having one or more straight channels 150SC through which material (e.g., fluid that contains therapeutic agent) can pass. There can be at least 3, for example at least 6 and even more typically at least 10 channels. There may be fewer than 1000 channels, for example no more than 200 and in many embodiments no greater than 50 of the channels 150SC.

Material, particularly ophthalmic pharmaceutical composition and aqueous humor fluid, is typically allowed to freely flow and/or diffuse into and out of the reservoir chamber 140 (FIG. 3A) with the size of the openings of channels 150SC assisting in controlling the rate of flow and/or diffusion into and out of the reservoir chamber 140. The openings of the plurality of channels 150SC, particularly for a passive system, have a cross-sectional area that controls the rate at which material, particularly therapeutic agent, flows out of the reservoir and into the eye. That cross-sectional area can be at least 8 $\mu m^2$, more typically at least 15 $\mu m^2$ and even more typically at least 50 $\mu m^2$. That same cross-sectional area can also be no greater than 4000 $\mu m^2$, for example no greater than 2000 $\mu m^2$ and in many embodiments no greater than 500 $m^2$. The cross-sectional area of the opening may comprise any sectional area of the opening wherein the outer perimeter of the opening is fully defined by the material of the control release mechanism and wherein, for fluid to pass through the opening into or out of the reservoir chamber 140, it also passes through the cross-sectional area.

In the illustrated embodiments, as shown in FIG. 3B, the porous structure 150 comprising the control release mechanism can be a plate 150PL. The plurality of channels 150SC extends through the plate 150PL. The plate 150PL may have opposing substantially parallel surfaces through with the channels extend to the opening on each surface. In the embodiments shown, the channels 150SC are cylindrical shape although they may be shaped otherwise as well. The channels 150SC may have a diameter of at least about 0.2 microns, for example at least about 2 microns and in many embodiments at least about 8 microns. The diameter of the openings may be no greater than about 100 microns, for example no greater than 40 microns and in many embodiments no greater than about 25 microns. While it is understood that a generally uniform distribution of the openings over the surface of the plate 150PL is desirable, other non-uniform distribution of opening the openings are also possible. A suitable thickness for the plate will typically be at least about 0.05 mm, more typically at least about 0.08 mm and will typically no greater than 0.5 mm and more typically no greater than 0.3 mm.

The porous structure 150 comprising the control release mechanism may comprise a plate 150PL. The plate 150PL may be formed of a variety of materials such as metals or polymeric materials. In many embodiments, the plate 150PL is formed of an etchable material such as silicon, which allows the channels 150SC to be etched into the material.

The number and size of each of the openings provides a combined cross-sectional surface area for the plate 150PL. The combined cross-sectional surface area of the channels 150SC may be no more than about 100,000 $\mu m^2$, so as to provide sustained release of the therapeutic agent for an extended time. While the combined cross-sectional surface area can be within a range from about 1000 $\mu m^2$ to about 100,000 $\mu m^2$, in many embodiments the combined cross-sectional area is within a range from about 2,000 $\mu m^2$ to about 30,000 $\mu m^2$, for example about 2,000 to about 10,000 $\mu m^2$. The combined cross-sectional area can be determined based on one or more of the thickness of the plate 150PL, the diffusion coefficient of the therapeutic agent, the volume of the reservoir chamber, the concentration of the therapeutic agent placed in the reservoir chamber, or the targeted release rate profile of the therapeutic agent above a minimum inhibitory concentration for a predetermined amount of time, or combinations thereof, for example.

Figure 4:
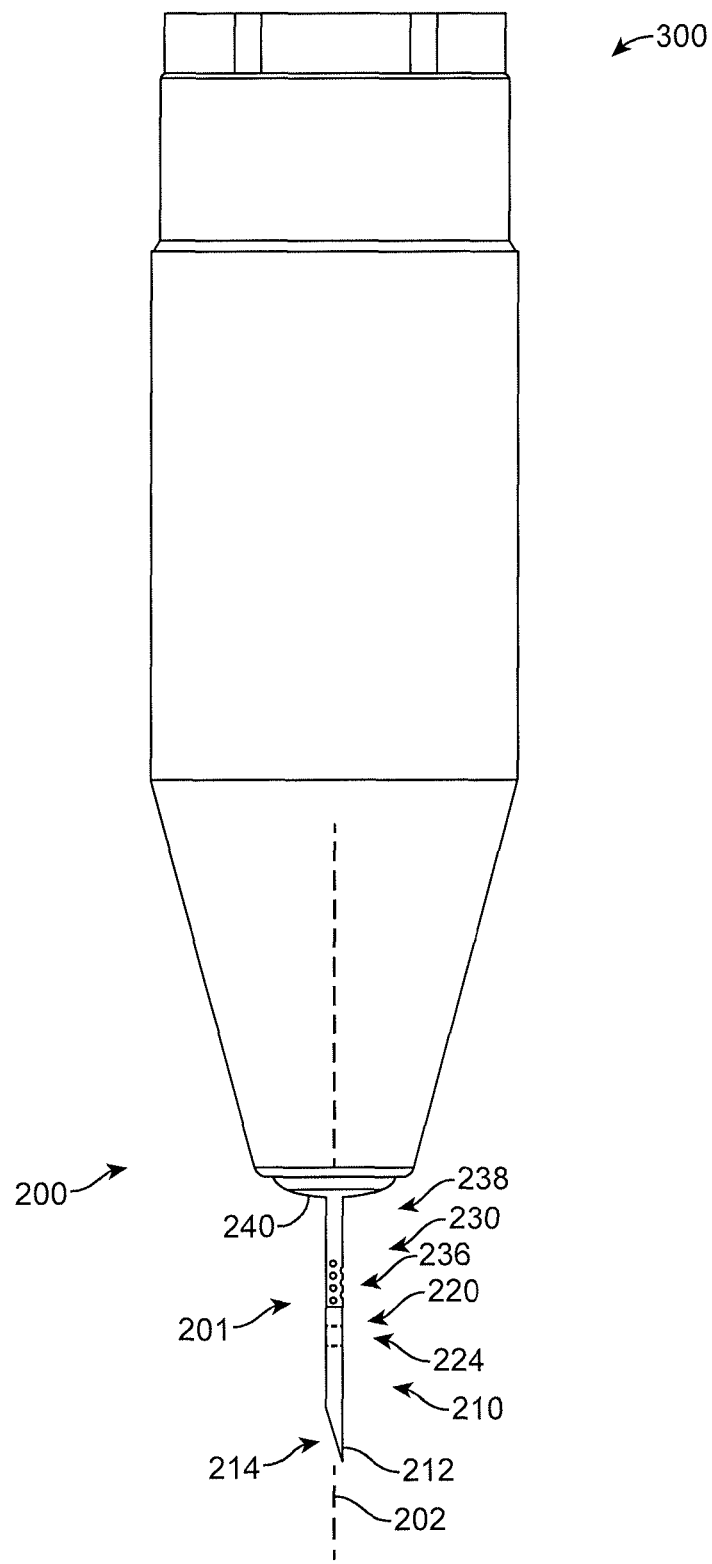
FIG. 4 shows an embodiment of an apparatus to exchange fluid of a device implanted in a an eye.

FIG. 4 shows an exemplary apparatus 200 to exchange fluid of a device implanted in an eye. The apparatus 200 may comprise or be coupled to a syringe 300 to inject a therapeutic fluid comprising a therapeutic agent in to the device implanted in the eye. The apparatus 200 comprise an elongate structure 201 comprising a distal portion 210, and intermediate portion 220 and a proximal portion 230. The elongate structure 201 extends along an axis 202 from a stop 240 to position the distal portion 210, the intermediate portion 220, and the proximal portion 230 corresponding locations of the reservoir chamber. The distal portion 210 comprises a distal tip 212 to penetrate tissue and the penetrable barrier of the implantable device and an opening 214 to inject therapeutic fluid into the implantable device. The intermediate portion 220 comprises a tapered section 224 to gradually increase a size of the channel formed in the penetrable barrier when the needle is advanced through the penetrable barrier, so as to maintain integrity of the penetrable barrier and inhibit damage to the penetrable barrier. In many embodiments, the tapered portion 224 may extend along axis 202 without holes so as to decrease pressure to the penetrable barrier that may otherwise occur near the edge of a hole. The proximal portion 230 may comprise a plurality of openings 236 to receive the fluid from the reservoir chamber of the implantable device. The proximal portion 230 may comprise an extension 238 extending from the stop 240. The extension 238 may extend from the stop 240 without holes to inhibit leakage when the fluid is exchanged and the stop 240 engages the conjunctiva.

Figure 5:
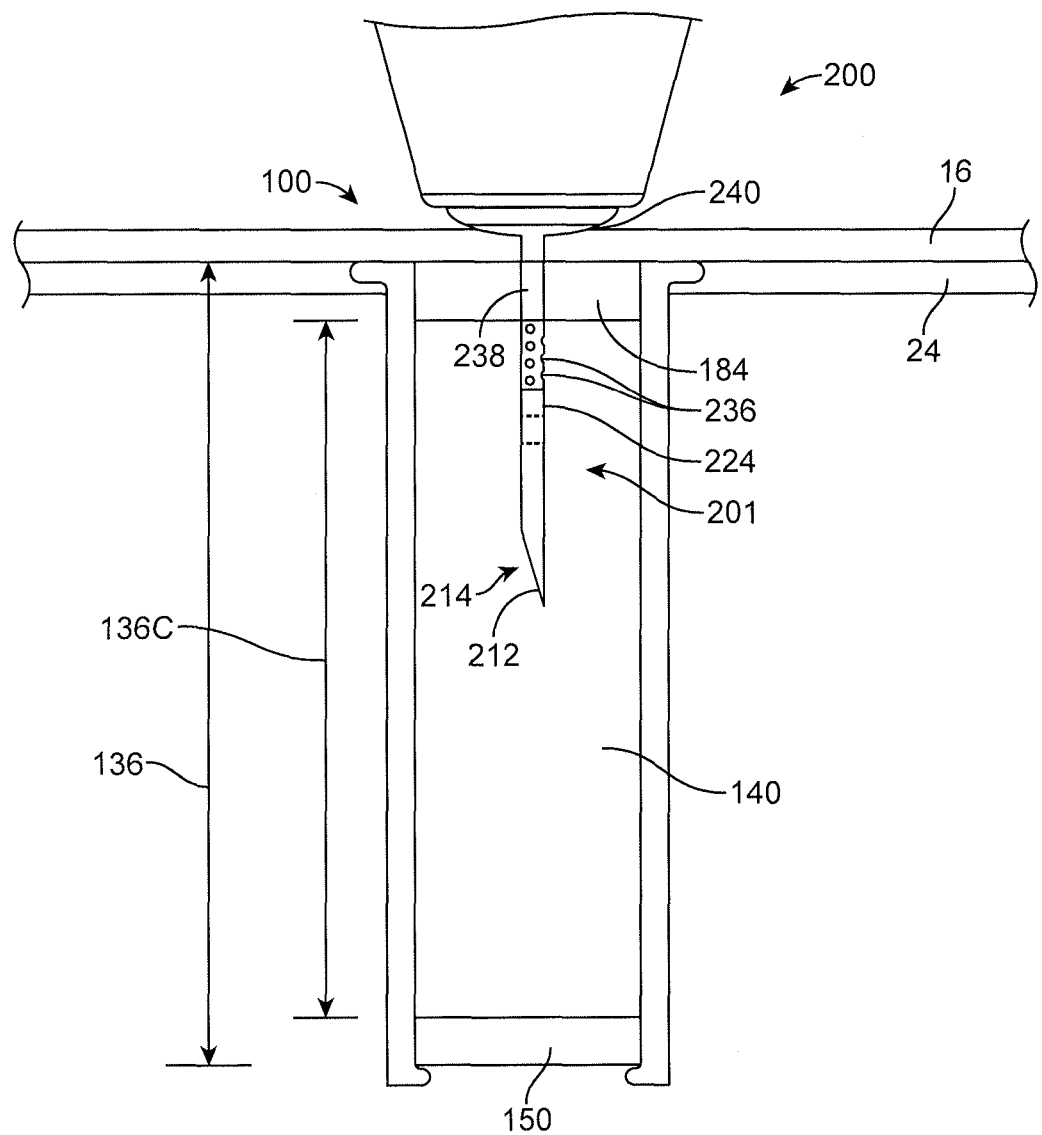
FIG. 5 shows an embodiment of an apparatus to exchange fluid coupled to an implanted device.

FIG. 5 shows the apparatus 200 coupled to an implantable device 100. The stop 240 is positioned to engage the conjunctiva 16, and the elongate structure 201 extends through the conjunctiva 16 and penetrable barrier 184 into the reservoir chamber 140 of the implantable device 100 when the apparatus 200 is coupled thereto. The elongate structure 201 can be sized so as to place distal tip 212 at a location within the reservoir chamber of the implantable device when the surface of the stop contacts the conjunctiva, for example. The distal tip 212 can be located on elongate structure 201 so as to place the distal tip 212 at a location from the penetrable barrier within implantable device 100 that is no more than a desired length, such as about % of the length 136 of the implantable device, and in some embodiments no more than about half of the distance 136C of the reservoir chamber. The plurality of openings 236 is located near the penetrable barrier 184 so as to receive fluid contacting the reservoir chamber. The extension 238 extends substantially through the penetrable barrier 184, for example at least about half way through the penetrable barrier so as to position the plurality of openings away from an external surface of the penetrable barrier and to inhibit leakage.

Figure 6:
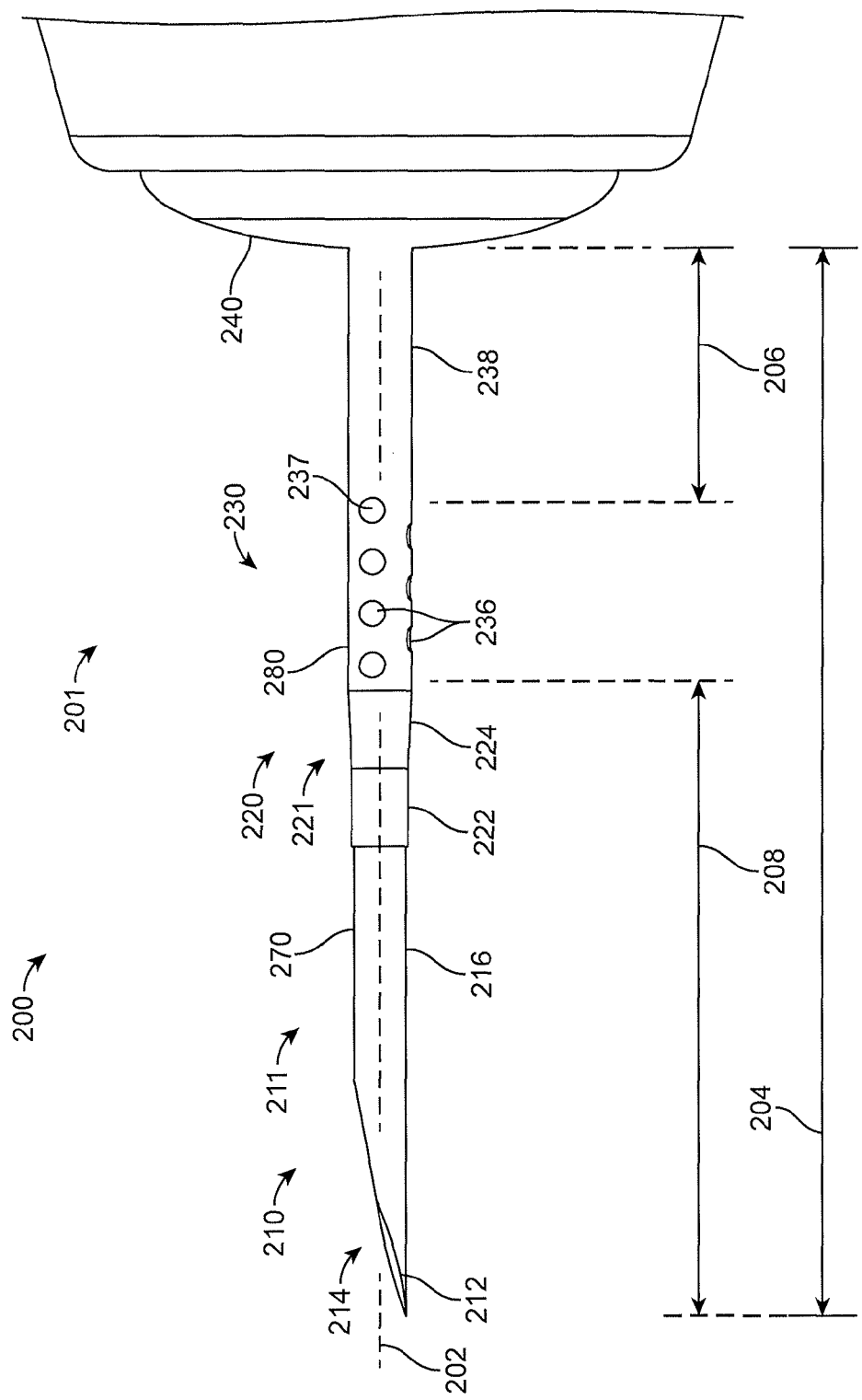
FIG. 6 shows an embodiment of an elongate structure of the apparatus to exchange fluid as in FIG. 5.

FIG. 6 shows an enlarged view of the elongate structure 201 of the apparatus 200. The elongate structure 201 extends along axis 202 between the distal tip 212 and stop 240. The distal portion 210 may comprise an extension 211 having a substantially constant cross-sectional size extending between the tip 212 to penetrate tissue and the intermediate portion 220. In many embodiments, the extension 211 comprises a portion of a needle 270 extending between the stop 240 and the tip 212 to penetrate tissue, which tip may comprise the tip of the needle to penetrate conjunctival tissue.

The tip to penetrate tissue 212 and the opening 214 can be located a distance 204 from the stop and the plurality of opens to provide efficient exchange of the fluid within the reservoir chamber of the implanted device. In many embodiments, the opening 214 is placed within the reservoir chamber at a distance from the stop 240 greater than the plurality of openings 236 to inhibit mixing of the injected therapeutic fluid with the fluid within the reservoir chamber of the implanted device. The opening 214 can be separated from the plurality of openings with a distance 208, such that the opening 214 can be located below the plurality of openings when the therapeutic fluid is injected.

The therapeutic fluid may comprise a density greater than the fluid of the implanted device and opening 214 can be placed below the plurality of openings 236 when the therapeutic fluid is injected to inhibit mixing. The axis 100A (see FIG. 3A) of the implantable device and the corresponding axis of the reservoir chamber can be oriented away from horizontal, such that porous structure 150 may be located below the penetrable barrier 184 when the therapeutic fluid is injected. The axis 202 can oriented away from horizontal such that opening 214 can be placed below the plurality of openings 236. The therapeutic fluid comprising the greater density can flow toward the distal end of the therapeutic device and the displaced fluid of the implantable device having the lesser density can be received by the plurality of openings 236 located above the opening 214.

Examples of therapeutic agents and corresponding formulations and fluids that may have a density greater than the density of the fluid within the chamber of the implanted device are listed in Table 1A. For example, one or more of the therapeutic agent or a stabilizer can increase the density of the therapeutic fluid. In many embodiments the therapeutic fluid having the greater density comprises a stabilizer, such as trehalose, and the therapeutic agent such as a protein comprising an antibody fragment. Alternatively or in combination, the therapeutic formulation may comprise an amount of therapeutic agent sufficient to provide a density greater than the fluid of the implanted device. The difference in density can be within a range from about 1% to about 10% and can depend on the density of the fluid within the reservoir chamber of the therapeutic device and density of the therapeutic fluid placed in the reservoir chamber with the exchange apparatus. The density of the therapeutic fluid may correspond to a density of the therapeutic agent and a density of the stabilizer (when present). In many embodiments, the density of the fluid of the reservoir chamber may correspond to a density of phosphate buffered saline, or plasma, or an amount of therapeutic fluid remaining in the reservoir from a prior exchange, or combinations thereof, for example.

When injected into a device implanted within the patient, the distance 204 may correspond to no more than approximately the distance of the reservoir chamber of device 140. The distance 204 may correspond substantially to the length of the reservoir chamber so as to place the distal tip near the porous structure, and the elongate structure of the exchange apparatus can be aligned with an elongate axis of the implantable device. In many embodiments, the distance 204 may correspond to no more than about half the distance of the reservoir chamber, such that the elongate structure 201 can be readily aligned with the implantable device. Work in relation to embodiments suggests than a distance providing a tolerance for angular alignment error of the axis 100A with the axis 202 can facilitate exchange and improve efficiency of the exchange. The distance 204 from stop 240 to tip 212 comprising no more than about half of the axial distance of the implantable device can facilitate alignment during injection.

The intermediate portion 220 may comprise an extension 222 extending between tapered portion 224 and the distal portion 210. The extension 222 may comprise a cross-sectional size that is smaller than the tapered portion 224. The extension 222 may comprise a smooth outer surface to penetrate tissue. The tapered portion 224 may comprise a smother outer surface to penetrate tissue and the penetrable barrier. The outer surface of the tapered portion can extend at an angle of inclination relative to the axis, and the tapered portion 224 may comprise a conic section having an angle with the axis such that the outer surface extends at the angle of inclination relative the axis. The angle of inclination of the tapered portion 224 can be no more than about 25 degrees, for example. The angle of inclination can be about 1 degree, about 2 degrees, about 5 degrees, about 10 degrees, about 15 degrees, about 20 degrees, or about 25 degrees, for example. The extension portion 216 may comprise a first cross-sectional dimension, and the portion having the plurality of openings may comprise a second cross sectional dimension greater than the first dimension, such that tapered portion having the angle of inclination extends there between to connect the extension portion 216 with the portion having the plurality of openings 236.

The proximal portion 230 may comprise the plurality of openings 236 spaced apart along the axis 202 and distributed circumferentially around the proximal portion to receive fluid from a plurality of circumferential and axial locations when the stop 240 engages the conjunctiva to place the plurality of openings within the reservoir chamber. At least one 237 of the plurality of openings can be separated from the stop 240 with a distance 206 corresponding substantially to the thickness of the penetrable barrier 184, such that the at least one 237 of the plurality of openings 236 can be placed near the inner surface of the penetrable barrier to receive fluid contacting the inner surface of the penetrable barrier. In many embodiments, the thickness of the penetrable barrier is within a range from about 0.25 to about 2 mm, for example within a range from about 0.5 to about 1.5 mm, such that the thickness of the penetrable barrier is substantially greater than a thickness of the conjunctiva which can be approximately 100 µm. The distance 206 corresponding substantially to the thickness of the penetrable barrier may correspond substantially to the thickness of the penetrable barrier and the epithelium of the patient.

A sheath 280 can be configured to extend over at least a portion of needle 270. The sheath 280 may extend along the intermediate portion 220 and the proximal portion 230, and the needle 270 can extend through the sheath. The sheath 280 may comprise the plurality of openings 236 and provide one or more channels extending along needle 270 to pass the fluid of the implantable device through the septum.

The sheath 280 may comprise portions corresponding to the intermediate and proximal portions of the elongate structure 201. The extension 222 may comprise a distal portion sheath 280 having an inner surface sized to engage an outer surface of the needle, and the diameter of the portion to engage the needle may comprise an inner cross sectional diameter less than the needle to engage the needle with at least one or of pressure or friction. The tapered portion 224 may comprise an intermediate portion of sheath 280, in which the sheath 280 comprises tapered surface to penetrate the tissue and penetrable barrier 184. The proximal portion 230 may comprise a proximal portion of the sheath 280 comprising the plurality of openings 236 and the extension 238. A channel 239 can extend along an outer surface of the needle to the plurality of openings 236. The channel 239 can extend proximally along extension portion 238 toward a container 250 (see FIG. 8A) to receive the fluid of the implantable device. The channel 239 may couple the plurality of openings to the container to receive the fluid of the implantable device.

Figure 7:
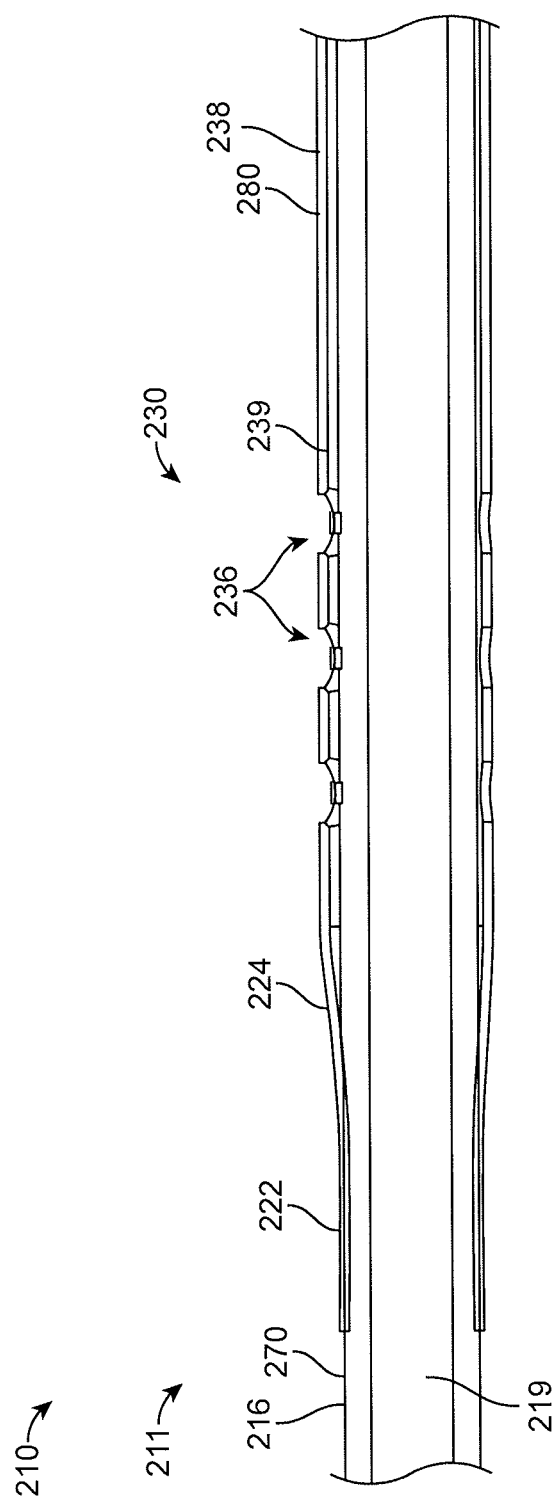
FIG. 7 shows a cross-sectional view of an embodiment of an elongate structure of the apparatus exchange fluid comprising a sheath over a needle.

FIG. 7 shows a cross-sectional view of an elongate structure of the apparatus exchange fluid comprising the sheath 280 over the needle 270. The needle may comprise channel 219, for example a lumen, extending distally to the opening 214 (see FIG. 6) and proximally to a connector to couple the channel 219 to a syringe, for example. A wall 252 of container 250 comprises sufficient strength to resist deformation when the stop 240 engages the tissue, and the stop 240 may comprise a deformable stop to couple to the tissue (see FIG. 8A). An outlet channel 254 extends from container 250 to at least one vent opening 258 to atmospheric pressure (see FIG. 8A).

FIG. 7A shows an exchange apparatus comprising a locking connector to couple to a syringe. The connector 290 may comprise a locking connector having an extension 292 sized to fit in a channel of connector 320 of syringe 300, for example (see FIG. 8B). The exchange apparatus 200 may comprise components of a standard locking needle assembly, for example a standard locking needle such as a Luer-Lok™ fitting. The wall 252 that defines container 250 and sheath 280 can fit over the needle 270 which may comprise a standard needle assembly. The wall 252 can extend a substantial distance from stop 240 to opening 258, for example, so as to define container 250 and channel 254 extending between the locking needle assembly and the wall.

FIG. 7B shows the elongate structure 201 and receiver container 250 of the exchange apparatus 200 of FIG. 7A. The wall 252 can extend around a distal portion of receiver container 250. The needle 270 and sheath 280 may extend through the wall 250. The stop 240 can be located on a distal portion of wall 252 and may comprise a soft material, for example a soft elastomeric material such as silicone elastomer. The stop 240 may fit within a recess formed on the surface of wall 252, and the needle 270 and the sheath 280 may extend through the soft elastomer stop 240, for example. The sheath 280 may comprise the tapered portion 224 proximal to the plurality of openings 236. The needle 270 can extend from tip 212 through chamber 250 to the connector 290 (see FIG. 7A), for example. The sheath 280 can extend from a first end 281 distal of the tapered portion 224 to a second end 283. The second end 283 may comprise an opening 285 into chamber 250. The outflow path of the displaced fluid from the implantable device may extend through the plurality of openings 236 to channel 239, along channel 239 to opening 285, and through opening 285 and into receiver container 250.

FIG. 7C shows sheaths suitable for combination with the exchange apparatus of FIGS. 7A and 7B. The sheath 280 can be configured in many ways (see 280A through 280K), and may comprise a wall thickness from about 0.0001 inches to about 0.01 inches, for example about 0.001 inches (¹⁄₁₀₀₀ inch, 25 µm). The sheath 280 may comprise an inside diameter sized larger than the outside diameter of needle 270 so as to provide an annular channel extending axially between the needle and the sheath from the plurality of openings 236 to the opening 285. The diameter of each of the holes can be within a range from about 0.0001 inches to about 0.1 inches, for example within a range from about 0.001 inches to about 0.01 inches.

The plurality of openings 236 may comprise one or more of many shapes and can be arranged in many ways. Each row may comprise from about 2 to about 20 holes, for example, and may comprise circular, oval, elliptical or other shapes, for example. The sheath 280 may comprise a sheath 280A having four rows of circular holes. Each of the holes may have a diameter of no more than about one half of the thickness of the outside diameter of the sheath 280, for example, and may be located circumferentially at 90 degrees to each other, for example. Each of the four rows may extend axially along the sheath 280. The rows can be spaced angularly at 90 degrees to each other, for example.

The sheath 280 may comprise sheath 280B having about two rows, each row comprising about four holes, each hole having a diameter of no more than about one eighth of the diameter of the outside diameter of the sheath 280. The two rows may be spaced apart circumferentially at 180 degrees, and the holes may comprise holes cross-cdrilled through both sides of the sheath, such that each hole has a corresponding hole on the other row on an opposite side of the sheath.

The sheath 280 may comprise sheath 280C comprising about four cross drilled holes, each hole having a diameter of no more than about three quarters of the diameter of the outside diameter of the sheath 280, for example. The holes may comprise pairs of holes, in which the holes of each pair have corresponding axial locations. The holes can be arranged in two rows spaced circumferentially at 180 degrees.

The sheath 280 may comprise sheath 280D comprising at least about three rows of at least about 3 holes, each hole having a diameter of no more than about one quarter of the diameter of the outside diameter of the sheath 280. The rows can be spaced apart circumferentially at about 120 degrees, for example.

The sheath 280 may comprise sheath 280E comprising at least about 40 holes, each hole having a diameter of no more than about one tenth of the diameter of the outside diameter of the sheath 280.

The sheath 280 may comprise sheath 280F comprising slots. Each of the slots may comprise a narrow dimension across and a long dimension across. The long dimension can extend axially along the sheath 280 and may extend a distance greater than the narrow dimension across. The long dimension can extend a distance greater than the outside diameter of the sheath 280 where the slots are located, for example. The narrow dimension across each slot may comprise no more than about half of the outside diameter of the sheath, for example.

The sheath 280 may comprise sheath 280G comprising staggered rows of holes. The plurality of openings 236 may comprise a first row and a second row of cross drilled holes 236A, in which the holes of the first row are paired with the holes of the second row at a common axial location for each pair. A third row of holes and a fourth row of holes may comprise cross drilled holes 236B located at 180 degrees to each other and 90 degrees to the first row and the second row. The axial locations of the third and fourth rows of holes can be staggered from the first and second rows of holes, such that the axial locations of the holes 236A of the first row and second row correspond to axial locations away from the holes 236B of the first row and the second row, for example.

The sheath 280 may comprise sheath 280H comprising oval holes having a long dimension and a short dimension, with the long dimension extending transverse to the axis of the sheath 280 and the short dimension extending along the axis of the sheath 280. The oval holes can be spaced apart and located in rows extending along the axis of the sheath as described herein, for example.

The sheath 280 may comprise sheath 280I comprising elongate oval holes having the long axis of the oval extending along the axis of the sheath and the narrow dimension of the oval extending transverse to the long axis of the sheath, for example.

The sheath 280 may comprise sheath 280J comprising at least about three rows of at least about 3 oval holes, each oval hole having a maximum dimension across of no more than about one quarter of the diameter of the outside diameter of the sheath 280. The rows can be spaced apart circumferentially at about 120 degrees as described herein, for example.

The sheath 280 may comprise sheath 280K comprising at least about 40 holes, each hole having a diameter of no more than about one tenth of the diameter of the outside diameter of the sheath 280. The holes can be located on opposite sides of the sheath 280, and may comprise cross drilled holes, for example.

FIG. 7D shows one of the sheath openings 236 having a beveled channel surface 284 to inhibit degradation of the penetrable barrier. The thickness 286 of the sheath wall may be within a range from about 0.0001 to about 0.01 inches, for example. The corner of 282 of the beveled channel surface of the opening may comprise an angle to inhibit degradation of the penetrable barrier, such as tearing with repeated injections.

Figure 7F:
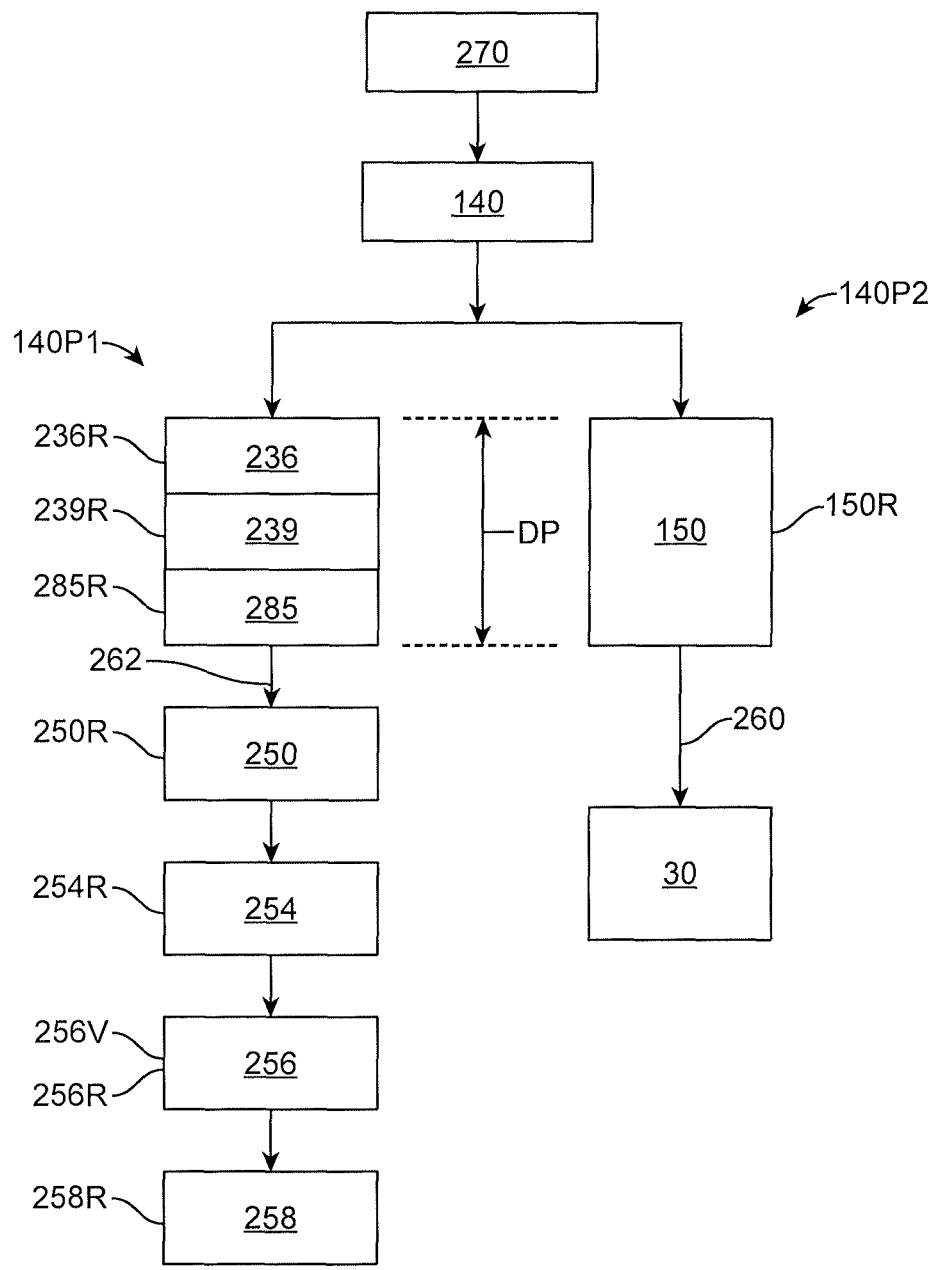
FIG. 7F shows an embodiment of schematic illustration of the pressure drops across the porous structure and the one or more channels extending from the plurality of openings to the receiver container.

FIG. 7E shows one of the sheath openings 236 having a rounded channel surface of the opening and edge to inhibit degradation such as tearing of the penetrable barrier with repeated injections, in accordance with embodiments of the present disclosure;

FIG. 7F shows a schematic illustration of the parallel outflow paths from the reservoir chamber 140. The first outflow path 140P1 extends from the reservoir chamber 140 to the receiver container 250, and the second outflow path 140P2 extends from the reservoir chamber 140 across the porous structure 150 to the vitreous humor 30 of the eye. As the intraocular pressure of the eye may be substantially less than the pressure of the implantable device during exchange, the intraocular pressure of the eye approximates atmospheric pressure. The second outflow path 140P2 extends comprises a pressure drop DP across the porous structure 150. The first outflow path 140P1 comprises the pressure drop DP across the plurality of openings 236, along the one or more channels 239 extending from the plurality of openings to the opening 285, and through the one or more openings 285 into the receiver container 250. In many embodiments, the channel 254 and the opening 258 each comprise air, such that the resistance to flow 254R of the channel 254 and the resistance to flow 258R of the opening such that the pressure drop across channel 254 and the opening 258 can be substantially less than the pressure drop DP, for example negligible.

In many embodiments, a valve 256V can be provided, so as to vary the resistance to flow of the outflow path to provide a bolus. The valve 256V may comprise a porous structure 256, for example, or a stop, plunger or other mechanism so as to increase pressure and provide the bolus when the exchange apparatus 200 has received a predetermined amount of displaced liquid from the reservoir container 140. The porous structure 256 may comprise a gas such as air initially, and be configured to contact the liquid from the reservoir chamber when the predetermined amount of fluid has been received and provide a substantial increase in the resistance to flow 156R, such that the bolus is passed through porous structure 150. Examples of valves and mechanisms to provide the bolus injection are described in U.S. PCT Pat. App. No. PCT/US2011/046812, filed Aug. 5, 2011, entitled "Injector Apparatus and Method for Drug Delivery", the entire disclosure of which has been previously incorporated herein by reference.

The pressure drops can be configured in many ways so as to inhibit a bolus release into the eye when the therapeutic fluid is exchanged with the implantable device fluid, or so as to release a bolus of therapeutic fluid through the porous structure of the implantable device, for example. The therapeutic fluid 260 comprising therapeutic agent 110 is injected through needle 270 into the reservoir chamber 140 of the implantable device, so as to pressurize the implantable device chamber with a force sufficient to pass a substantial portion of the implantable device fluid 262 into the receiver container 250. A pressure drop DP extends from the reservoir chamber of the implantable device through the plurality of openings 236, along channel 239 extending to opening 285, and through opening 285, such that the implantable device fluid 262 is received in receiver container 250. The outflow path from the reservoir chamber of the implantable device to the receiver container 250 comprises a resistance to flow corresponding to a resistance to flow 236R of the plurality of openings 236, the resistance to flow 239R of the channel 239, and the resistance to flow 285R of opening 285, for example. The resistance 150R to flow of the porous structure corresponds to an amount of therapeutic fluid 260 passed from the reservoir chamber of the implantable device to the chamber of the eye containing vitreous humor, for example. The amount of fluid into the receiver container such as the chamber 250 relative to the amount of fluid through the porous structure is related to the resistances based on parallel flow. The amounts of flow to the receiver container 250 and through the porous structure 150 correspond substantially to the following equations:

(Amount through porous structure)/(Amount through receiver)=(Resistance 236R+Resistance 239R)/(Resistance 150R)

(Amount through porous structure)=(Amount through receiver)*(Resistance 236R+Resistance 239R)/(Resistance 150R)

(Amount to receiver container)=(Amount through porous structure)*(Resistance 150R)/(Resistance 236R+Resistance 239R)

The resistance 150R corresponding to extended release of the therapeutic agent can be substantially greater than the resistance of the outflow path to the receiver container 250 comprising resistance 236R and resistance 239R, such that the amount of bolus of therapeutic fluid 260 and implantable device fluid 262 through the porous structure 150 can be less than about 1 µL combined, for example. Alternatively, the resistance to flow of the outflow path can be sufficient such that a substantial amount of therapeutic agent 110 is released through porous structure 150 with a bolus during exchange. The resistance to flow along the outflow path may comprise one or more of the resistance to flow 236R of the plurality of openings 236, the resistance to flow 239R of the channel 239 extending from the plurality of openings to the opening 285, or the resistance to flow 285R of the opening 285, for example, or combinations thereof. The size and number of the plurality of openings 236 and the thickness 286 of the sheath can determine substantially the resistance 236R of the plurality of openings. The length of the channel 239 extending from the plurality of openings 236 to the opening 285, and the transverse dimensions of the channel can determine substantially the resistance to flow 239R. For example the channel 239 may comprise a plurality of channels extending from the plurality of openings opening 236 to the reservoir container 250.

The resistance to flow 150R can vary with the RRI of the porous structure 150. In many embodiments, the resistance to flow 150R of porous structure 150 is inversely related to the RRI of the porous structure. For example, experimental testing with syringes and test therapeutic devices has shown that a bolus can be achieved through a porous structure 150 having an RRI of about 0.06 when the resistance to flow of outflow path is sufficiently large and device 100 is constructed such that chamber 140 can be pressurized to at least about one atmosphere, for example. However, porous structures having lower RRIs can provide a substantial resistance to flow so as to inhibit release of a substantial bolus. For example a porous structure 150 having an RRI of about 0.02 has a resistance to flow 150R such that an attempt to pass a substantial bolus amount through the porous structure 150 with a clinically acceptable injection time of 30 seconds or less may result in substantial pressure, for example greater than about four atmospheres.

The resistance to flow 150R of the porous structure 150 comprising the plurality of straight channels 150SC varies with one or more of the combined cross-sectional surface area of the channels 150SC, the number of openings, the size of each of the openings, or the thickness 150T, and combinations thereof. The combined cross-sectional surface area of the channels 150SC may be no more than about 100,000 µm², so as to provide a resistance to flow 150R of the porous structure 150 sufficient decrease flow through the porous structure and provide exchange as described herein. The combined cross-sectional surface area can be within a range from about 1000 µm² to about 100,000 µm², for example, so as to provide a resistance to flow 150R greater than the resistance to flow of the outflow path 140P1. For example, the combined cross-sectional area within a range from about 1,000 µm² to about 30,000 µm² may provide a substantial resistance to flow 150R, which may be substantially greater than the resistance to flow of the outflow path. In many embodiments, the combined surface area is within a range from about 1,000 µm² to about 10,000 µm², and the resistance to flow 150R is substantially greater than the resistance to flow of the outflow path so as to inhibit bolus release through the porous structure (see also FIGS. 3A and 3B).

The resistance to flow of the outflow path comprising resistance 236R and 239R may comprise about 5 percent of the resistance 150R to flow of the porous structure 150, such that about 5 µL of fluid flows through the porous structure and about 95 µL flows through the plurality of openings 236 and channel 239. The size and number of the plurality of openings and dimensions of channel 239 can be determined by a person of ordinary skill in the art based on the teachings described herein so as to provide a target amount of bolus for a target amount of injected therapeutic fluid.

As the therapeutic fluid 260 can be denser than the implantable device fluid 262, a substantial portion of the fluid through the porous structure 150 may comprise the therapeutic fluid 260, for example.

Figure 8A:
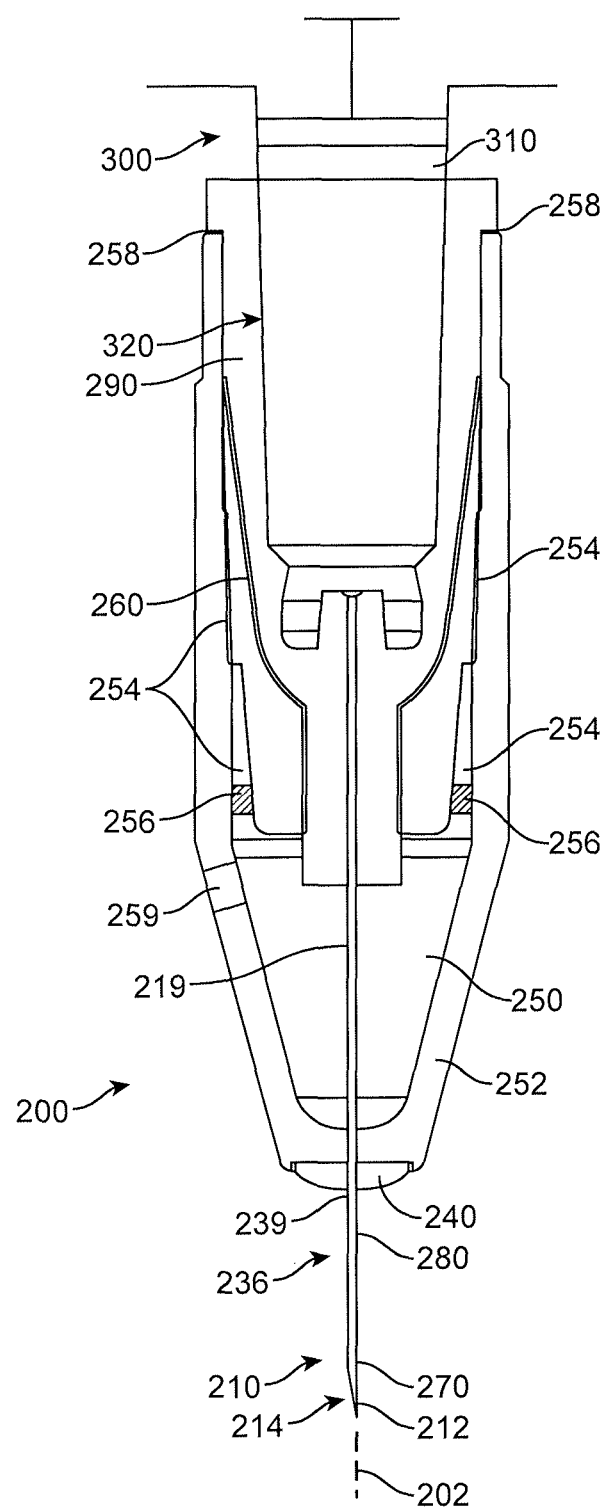
FIG. 8A shows a cross-sectional view of an embodiment of the apparatus to exchange fluid as in FIGS. 5 and 6 coupled to a syringe.

FIG. 8A shows a cross-sectional view of the apparatus to exchange fluid as in FIGS. 5 and 6 coupled to a syringe. The channel 239 extends from the plurality of openings 236 to a container 250 to receive the fluid of the implantable device. The distal portion 210 comprising tip 212 and opening 214 comprise a distal portion of needle 270. The channel 219 extends along an axis 202 from the opening 214 to a connector 290. The connector 290 is configured to couple to a connector 320 of an injector. The injector may comprise a syringe 300 (not to scale). The injector may comprise a container 310 comprising a therapeutic fluid for injection, and the container 310 can be fluidically coupled to the opening 214 on distal tip 212 when the connector 320 engages the connector 290.

The sheath may comprise an annular configuration shaped for placement over the substantially annular needle, such that the sheath and needle comprise a substantially concentric configuration extending along axis 202.

The connector 290 of the exchange apparatus and the connector 320 of the injector can be configured in many ways. For example, the connector 290 and the connector 320 may comprise a standard connector such as a Luer connector or a pressure fit connector. Alternatively, the connector 290 may comprise a non-standard connector to limit access to the exchange apparatus 200. For example the connector 290 may comprise a star connector or other connector, and connector 290 may comprise a lock and key mechanism. The lock and key mechanism may comprise a lock on the exchange apparatus configured to receive a key of the injector, such that the lock of connector 290 can receive the key of connector 320 to couple the injector to the exchange apparatus and permit injection from chamber 310 through opening 214. Alternatively, the syringe 300 may be affixed to exchange apparatus 200, and syringe 300 provided with a single dose of therapeutic agent.

The container 250 of the exchange apparatus may have a volume to limit and amount of fluid received from the implantable device and to limit use of the apparatus to a single use. For example, the volume of the container may comprise no more than about 100 µL, for example no more than about 50 µL, so as to limit and amount of fluid exchanged with the implantable device and inhibit reuse of the exchange apparatus from patient to patient. The implantable device can be provided to a health care provider with an amount of gas, such as air within the receiver container 250, and the receiver container may comprise a structure along a vent path to limit the amount of fluid that can be received by the container 250.

The exchange apparatus 200 may comprise a porous structure 256 to inhibit passage of the fluid of the implantable device and limit the amount of fluid exchanged. The porous structure 256 may comprise a material to pass a gas, such as air and inhibit flow of a liquid, such as the fluid of the implantable device. The material may comprise one or more of a fabric, a porous fabric, a semipermeable membrane, an air permeable material, a moisture vapor transfer waterproof fabric, a hydrophilic porous material, or a porous sintered material, for example. The channels extending through the porous structure 256 may comprise a gas, such as air and a lower resistance to flow of the gas and a substantially greater resistance to flow of a liquid, such as the therapeutic fluid, such that the exchange is substantially inhibited when receiver container 250 is substantially filled with fluid of implanted device and the fluid exchanged with the implanted device contacts the porous structure 256. The porous structure 256 may comprise one or more of a fabric, a porous fabric, a semipermeable membrane, an air permeable material, a moisture vapor transfer waterproof fabric, a hydrophilic porous material, or a porous material or a porous sintered material, for example.

The exchange apparatus may comprise a structure 259 composed of a material penetrable with a needle to draw a sample from the receiver container. The structure 259 may comprise one or more materials suitable for penetration with a needle such as one or more of rubber or silicone elastomer, for example. The structure 259 may comprise the porous structure 256, for example, and the material penetrable with the needle may comprise one or more of a fabric, a porous fabric, a semipermeable membrane, an air permeable material, a moisture vapor transfer waterproof fabric, a hydrophilic porous material, or a porous material or a porous sintered material, for example.

Figure 8B:
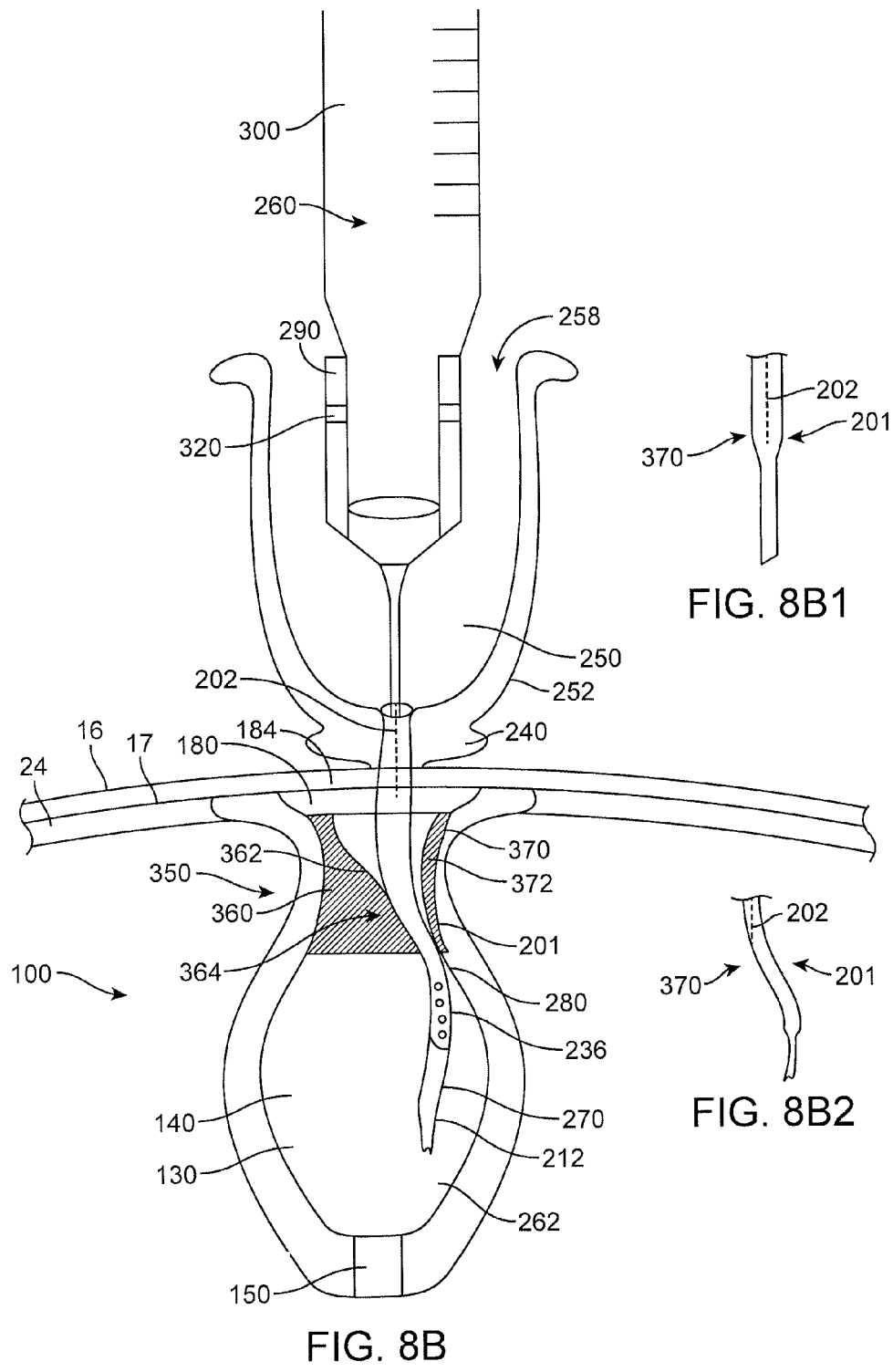
FIG. 8B shows an embodiment of an implantable therapeutic device comprising a lock and an exchange apparatus comprising a key to the lock.

FIG. 8B shows an embodiment of an implantable therapeutic device 100 comprising a lock and key mechanism 850 to place a therapeutic agent in the implantable device. The lock and key mechanism 350 comprises a lock 360 and a key 370. The lock 360 can be located on the implantable device to inhibit access to the reservoir chamber of the implantable device. The exchange apparatus 200 comprises the key 370 to access the reservoir chamber to place the therapeutic agent 110 as described herein. The lock can be configured in many ways and may comprise one or more of a deflected channel, a curved channel, a helical channel, a serpentine channel, engagement structures, a magnet, a door, a movable door, a tumbler, a cylinder, pins or a shear line, for example. The key can be configured in many ways so as to correspond to the lock and may comprise one or more of a deflectable elongate structure, a curved elongate structure, a helical elongate structure, a serpentine elongate structure, engagement structures sized to engage engagement structures of the lock, for example.

In many embodiments, the lock 360 inhibits access with a straight rigid needle, so as to inhibit placement of the therapeutic agent which may be ineffective or inappropriate when placed in the therapeutic device. For example, the exchange apparatus 200 can be delivered to the physician with a predetermined therapeutic agent formulation and key, and the implantable device has the lock configured to receive the key to place the therapeutic agent, such that access to the implantable device can be limited substantially.

In many embodiments, the lock 360 comprises the deflected channel 364, which may comprise one or more of a bent channel, a curved channel, a helical channel, or a serpentine channel, for example. The lock 360 may comprise a stiff substantially non-penetrable biocompatible material, for example one or more of rigid plastic, polymethylmethacrylate (hereinafter "PMMA"), polycarbonate, metal, or titanium, for example. The key 370 may comprise one or more of many components and structures of elongate structure 201 as described herein. The key 370 may comprise one or more of a deflectable key or a deflected key configured to extend along the deflected channel 364 to deliver the therapeutic fluid 260 and receive the implantable device fluid 262. The lock comprises an engagement structure 362 to engage an engagement structure 372 of the key. The engagement structure 362 may comprise an inner surface of the channel 364, and the outer surface of the deflectable key engages the inner surface of the channel so as to deflect the elongate structure 201 to advance along channel 364.

FIG. 8B1 shows an embodiment of a deflectable elongate structure 201 in an unloaded configuration prior to insertion in the lock 360 of FIG. 8B. The elongate structure comprises an axis 202, and the elongate structure may extend substantially along the axis 202 so as to provide column strength to the elongate structure 201 to penetrate the penetrable barrier 184 of access port 180. The elongate structure 201 may comprise a resistance to deflection sufficiently low so as to advance along channel 364 and a column strength sufficient to penetrate tissue and the penetrable barrier. The deflectable elongate structure 201 can be deflected substantially away from axis 202 when advanced into the lock 360.

The lock 360 may comprise a rigidity sufficient to inhibit penetration with a straight needle, and the channel 364 can be extend internally with lock 360.

The key 370 comprising the elongate structure 201 can extend through tissue such as the conjunctiva and epithelium to reach the lock 360, and the key can be configured to penetrate the tissue. The penetration of the tissue and penetrable barrier 184 inhibits contamination of the reservoir chamber as the barrier function of the conjunctiva 16 and Tenon's capsule 17 can be substantially maintained. The deflectable elongate structure 201 can be made of one or more of many components and may comprise sheath 280 and needle 270. The needle and sheath can be configured to deflect together when advanced along channel 364. The deflectable needle may comprise a metal, for example Nitinol, and the sheath may comprise a polymer such as polyimide, for example.

FIG. 8B2 shows an embodiment of a deflected elongate structure 201 in an unloaded configuration prior to insertion in the lock of FIG. 8B. The key 370 comprising deflected elongate structure may comprise one or more of many materials providing a stiffness sufficient to retain the deflected shape in the unloaded configuration. In the unloaded configuration, the deflected elongate structure 201 of key 370 extends away from axis 202. The deflected elongate structure 201 may comprise a preformed deflection profile corresponding to the path of channel 364 extending through the lock 360 from a first side of the lock toward the conjunctiva to a second side of the lock toward the reservoir chamber 140.

FIG. 8C1 shows an embodiment of an implantable therapeutic device 100 comprising a lock 360 and an exchange apparatus 200 comprising a rotatable key 370 to the lock 360. The exchange apparatus 200 can be advanced toward the implantable device 100 and rotated as shown with arrows 374. The engagement structures 372 of the key couple to the engagement structures 362 of the lock, such that the lock 360 opens to allow access of the elongate structure 201. The engagement structures may comprise one or more of many structures, for example magnets, teeth, or notches, and the engagement structures can be spaced apart at appropriate distances such that the engagement structures of the lock are keyed to the engagement structures of the key to allow access. For example the engagement structures 372 of the key may comprise magnets, and the engagement structure of the lock may comprise a magnetic material such that the key can be opened with the lock and the magnetic field extending through the conjunctiva 16 and the Tenon's capsule 17, for example. Alternatively, the conjunctiva and/or Tenon's capsule can be displaced and the engagement structures 372 of the key can contact the engagement structures 362 of the lock to allow access to the reservoir chamber.

FIG. 8C2 shows an embodiment of the implantable therapeutic device 100 of FIG. 8C1 in a unlocked configuration in which the elongate structure 201 extends through the open lock and penetrable barrier 184 to access the reservoir chamber 140 of the implantable device 100. The exchange apparatus can place the therapeutic fluid 260 in the implantable device 100 and receive the implantable device fluid 262 in the receiver container 250 as described herein.

FIG. 8D1 shows an embodiment of an implantable therapeutic device comprising 100 a slide lock 360 and exchange apparatus 200 comprising a slidable key to engage the slide lock. The exchange apparatus 200 can be advanced toward the implantable device 100 and slid as shown with arrows 374. The engagement structures 372 of the key couple to the engagement structures 362 of the lock, such that the lock 360 opens to allow access of the elongate structure 201. The engagement structures of the slide lock 360 and slide key 370 may comprise structures similar to the rotatable key and lock described with reference to FIG. 8C1.

FIG. 8D2 shows an embodiment of an implantable therapeutic device 100 in an unlocked configuration in which the elongate structure 201 extends through the open lock 360 and penetrable barrier 184 to access the reservoir chamber 140 of the implantable device. The exchange apparatus can place the therapeutic fluid 260 in the implantable device 100 and receive the implantable device fluid 262 in the receiver container 250 as described herein.

Figure 8E:
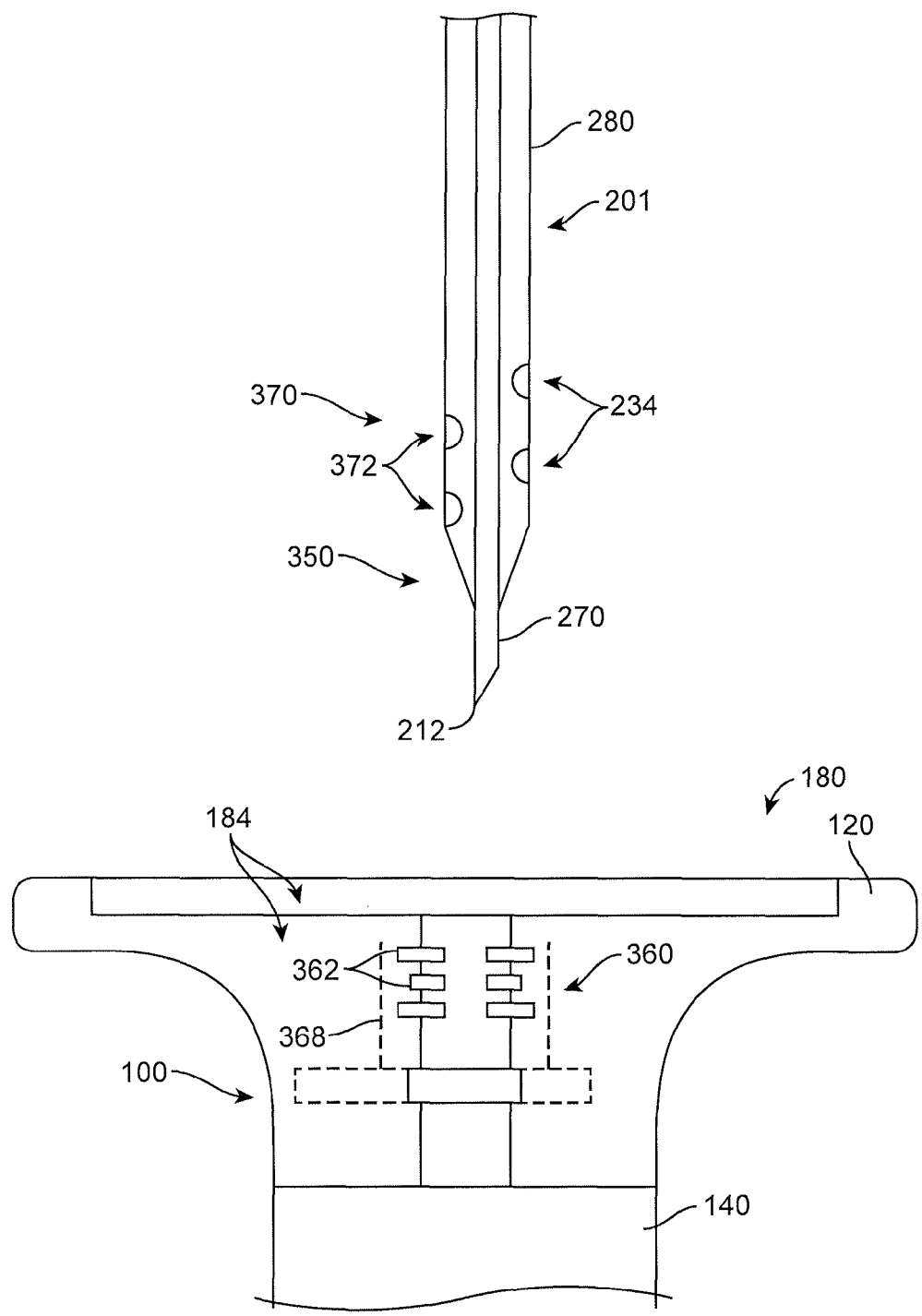
FIG. 8E shows an embodiment of an implantable therapeutic device comprising a lock and an exchange apparatus comprising an elongate structure having engagement structures to open the lock.

FIG. 8E shows an embodiment of an implantable therapeutic device 100 comprising a lock 360 and the elongate structure 201 of the exchange apparatus 200 comprising the key 370. The elongate structure 201 can be configured in many ways so as to comprise the key 370. The engagement structures 372 of the key 370 can be located near a distal end 212 of the elongate structure 201, for example. The engagement structures 272 can be affixed to the needle 270 and may comprise annular structures extending around the needle. Alternatively or in combination, the sheath 280 of the elongate structure may comprise the engagement structures. For example, the one or more openings 289 of the sheath 280 can be sized and located so as to comprise the engagement structures 372 of the key 370.

The lock can be configured in many ways to receive the key, and the engagement structures 362 of the lock may comprise pins aligned to a shear plane 368 when the key is inserted, for example.

Figure 9:
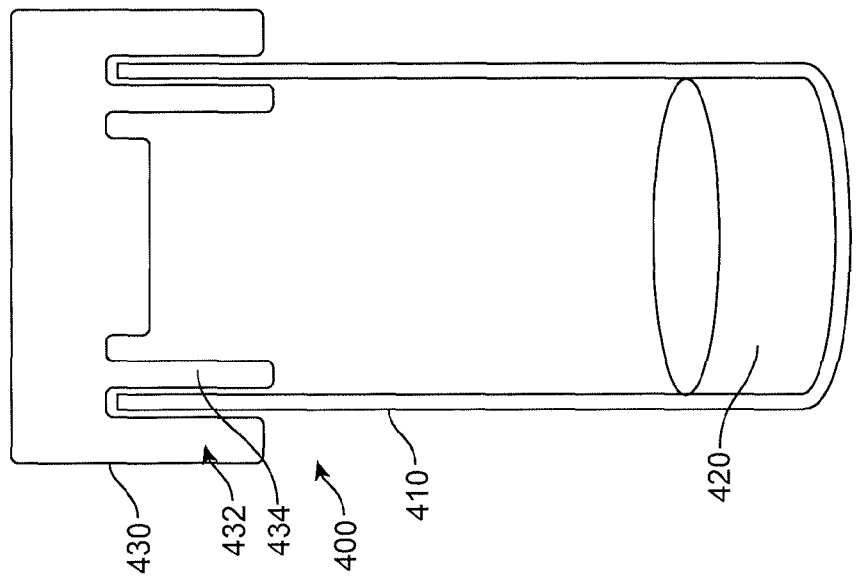
FIG. 9 shows an embodiment of a container to receive and store the exchange apparatus.

FIG. 9 shows a container 400 to receive and store the exchange apparatus 200. The container 400 may comprise a barrier material 410 to inhibit evaporation from within the container to the outside environment, a cap 430 and a base supporting a soft penetrable material 420. The cap 430 may comprise a protrusion such as an annular protrusion 432 to seal around an outer portion of the wall of the container. The cap 430 may comprise a retention structure to hold the injector apparatus, for example a second protrusion, such as an annular protrusion 434 to receive and hold the exchange apparatus 200. The cap 430 may comprise a soft barrier material, such as an elastomer, for example.

Figure 10:
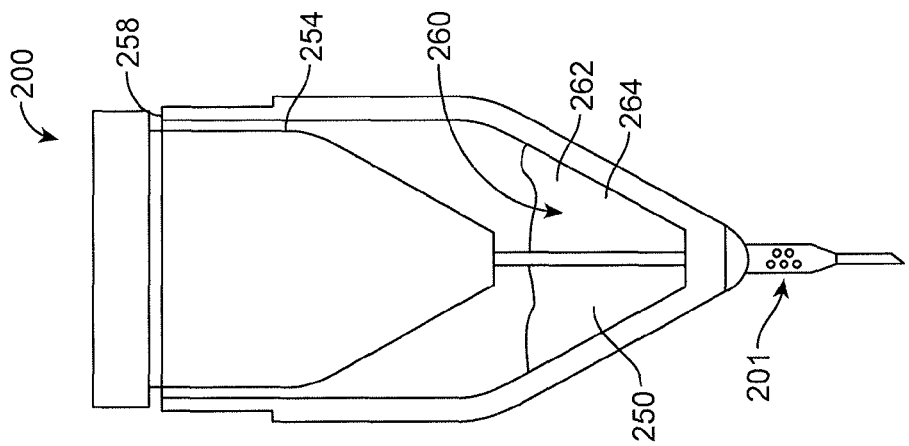
FIG. 10 shows an embodiment of an exchange apparatus having a fluid sample within the receiver container.

FIG. 10 shows an exchange apparatus 200 having the implantable device fluid 262 comprising a fluid sample 264 within the receiver container 250. The receiver container 250 can be coupled to the elongate structure 201. The channel 254 can extend from the container to 250 to opening 258. The receiver container 250 may comprise a combination of one or more of the therapeutic fluid 260, the implantable device fluid 262 comprising sample fluid 264. Depending on the exchange apparatus and orientation, the implantable device fluid 262 comprising sample fluid 264 may comprise a substantial majority of the fluid of the receiver container 250.

Figure 11:
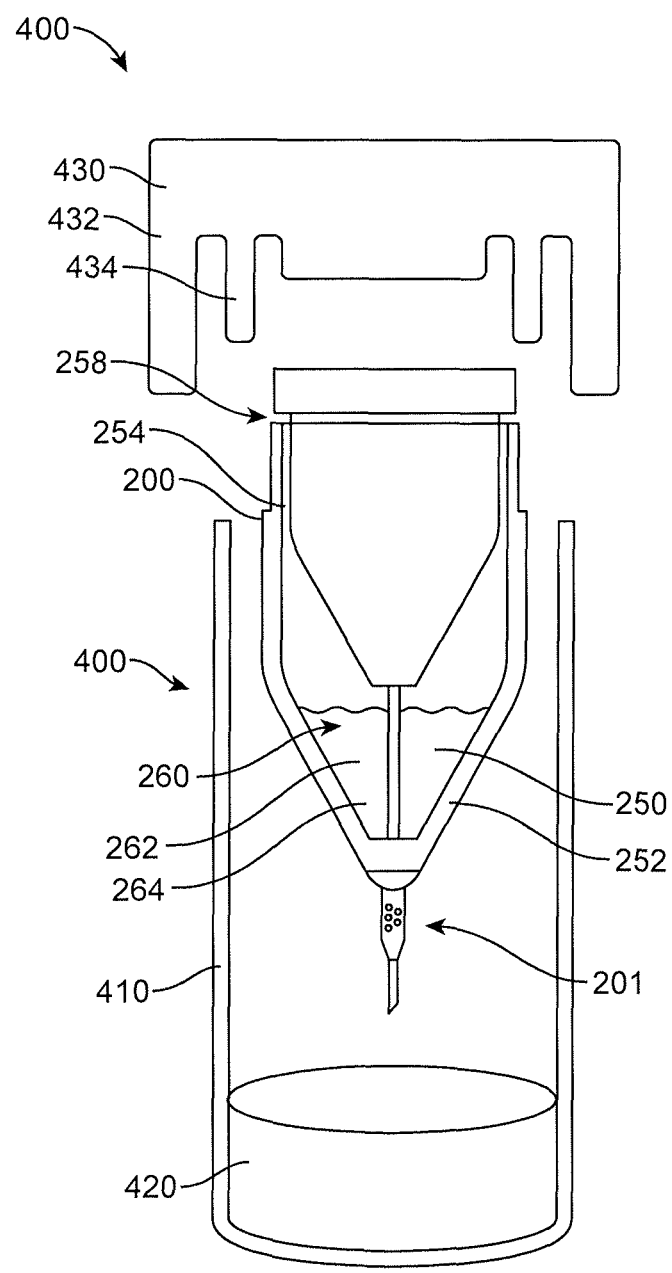
FIG. 11 shows an embodiment of the exchange apparatus having the fluid sample placed partially within the storage container.

FIG. 11 shows the exchange apparatus 200 having the fluid sample 264 placed partially within the storage container 400. The cap 430 is shown over but not yet covering the vent channel 254 extending from the receiver container 250 to the opening 258.

Figure 12:
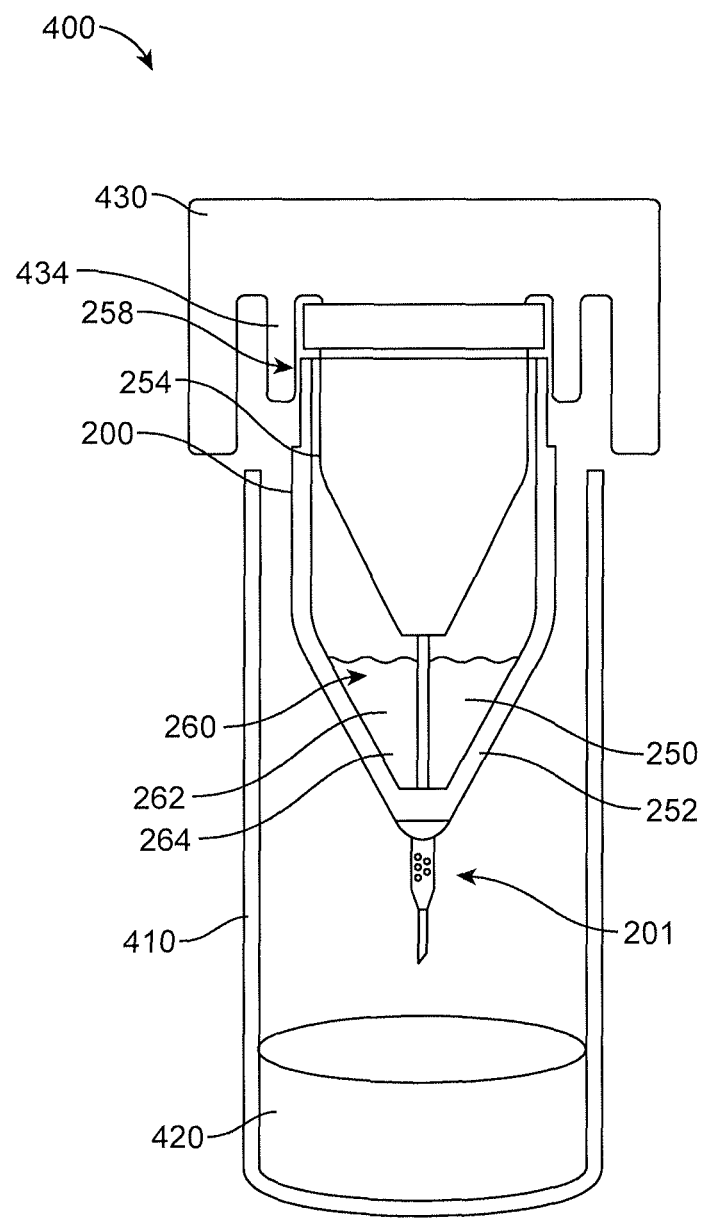
FIG. 12 shows an embodiment of a cap of the storage container placed over an outlet channel of the exchange apparatus to inhibit leakage.

FIG. 12 shows a cap 430 of the storage container placed over the outlet channel opening 258 of channel 254 coupled to the receiver container 250 of the exchange apparatus, so as to inhibit one or more of leakage or evaporation from container 250.

Figure 13:
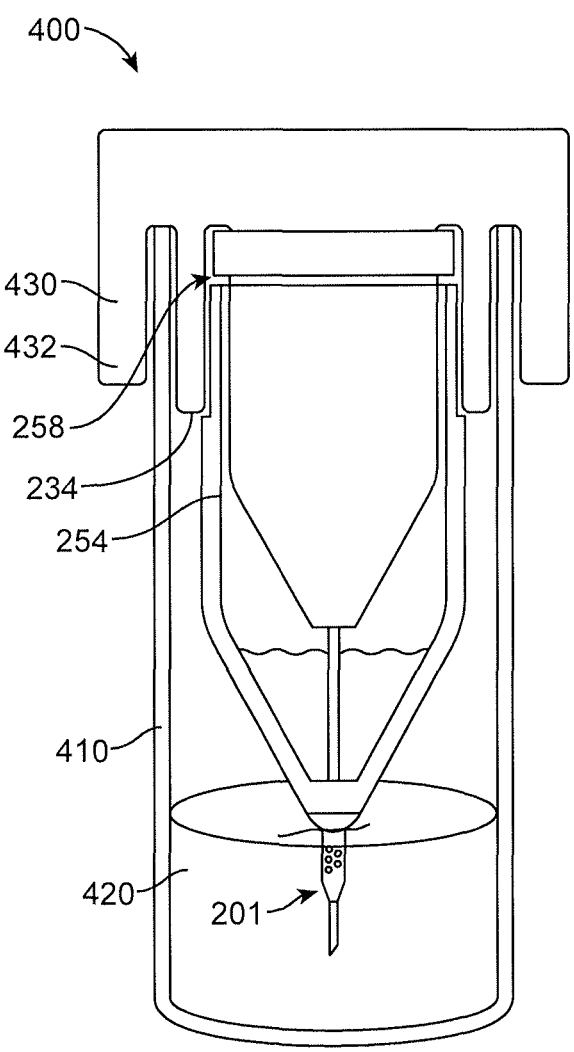
FIG. 13 shows an embodiment of an elongate structure of the exchange apparatus placed within a soft penetrable material near the bottom of the storage container and the cap placed over the container so as to seal the exchange apparatus within the container.

FIG. 13 shows an elongate structure 201 of the exchange apparatus placed within a soft penetrable material 420 near the bottom of the storage container and the cap placed over the container so as to seal the exchange apparatus container. The soft penetrable material 420 may comprise a soft material capable of sealing, for example a soft elastomeric material such as silicone elastomer.

Figure 14:
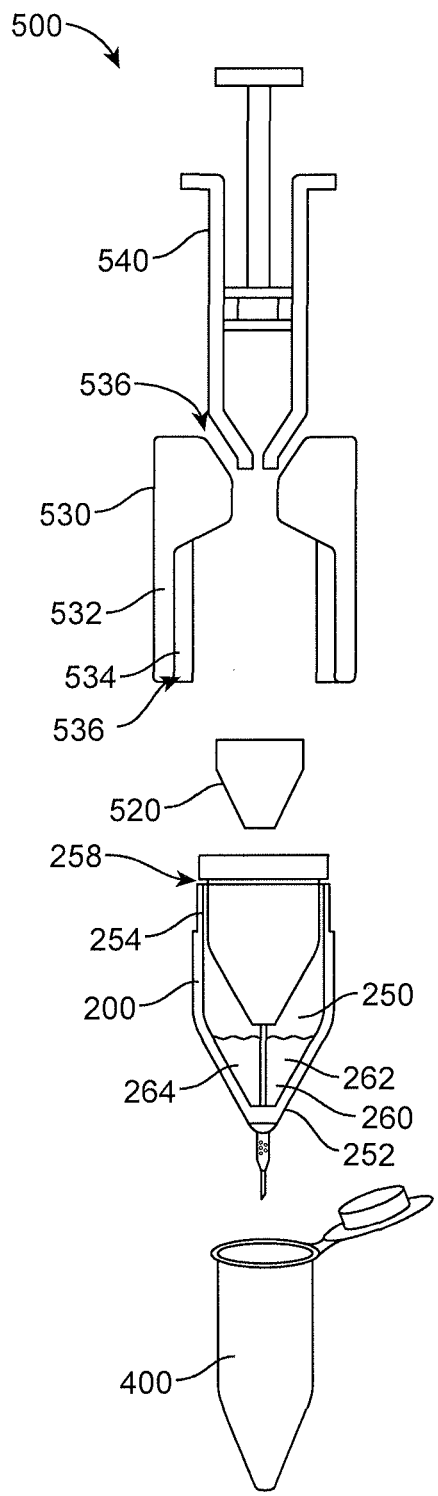
FIG. 14 shows an embodiment of an apparatus to remove the sample fluid from the receiver container.

FIG. 14 shows an apparatus 500 to remove the sample fluid from the receiver container 250 of the exchange apparatus 200. The apparatus 500 comprises a sample container 400, a plug 520, a syringe 540 to pressurize the receiver container 250, and a coupling 530 to couple the syringe to the receiver container of the exchange apparatus 200. The coupling 530 may comprise a receptacle 536 to receive the proximal end portion of the exchange apparatus 200. The receptacle 536 may comprise a structure 532 to couple the syringe to the coupling, for example a Luer connector, a Luer-Lok™ connector, or other known connector, for example. The retention structure 532 to retain the exchange apparatus 200 and a contact structure 534 to contact the outer wall of the exchange apparatus and fluidly couple the syringe to the opening 528 when the exchange apparatus 200 is retained with the coupling 530. The contact structure 534 may inhibit flow of injection fluid from syringe 540, such as air, between the retention structure 532 and wall 252 of the exchange apparatus, for example with a seal between the retention structure 532 and the wall 252 of the exchange apparatus 200.

Figure 15:
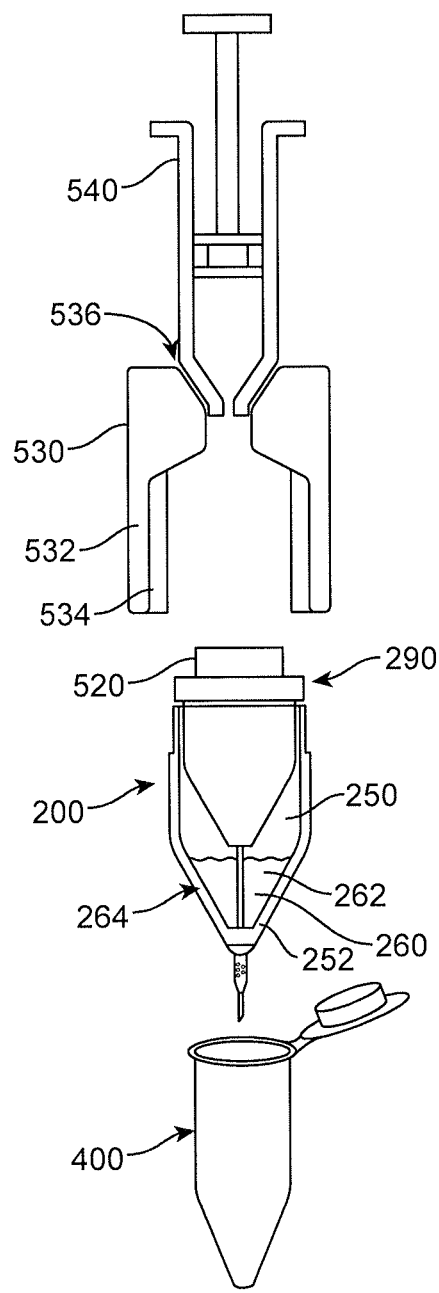
FIG. 15 shows an embodiment of a cap placed on a connector to couple a syringe to the exchange apparatus.

FIG. 15 shows a cap 520 placed on the connector 290 to couple the syringe to the exchange apparatus, so as to inhibit fluidic flow from syringe 540 through the needle of the elongate structure 201.

Figure 16:
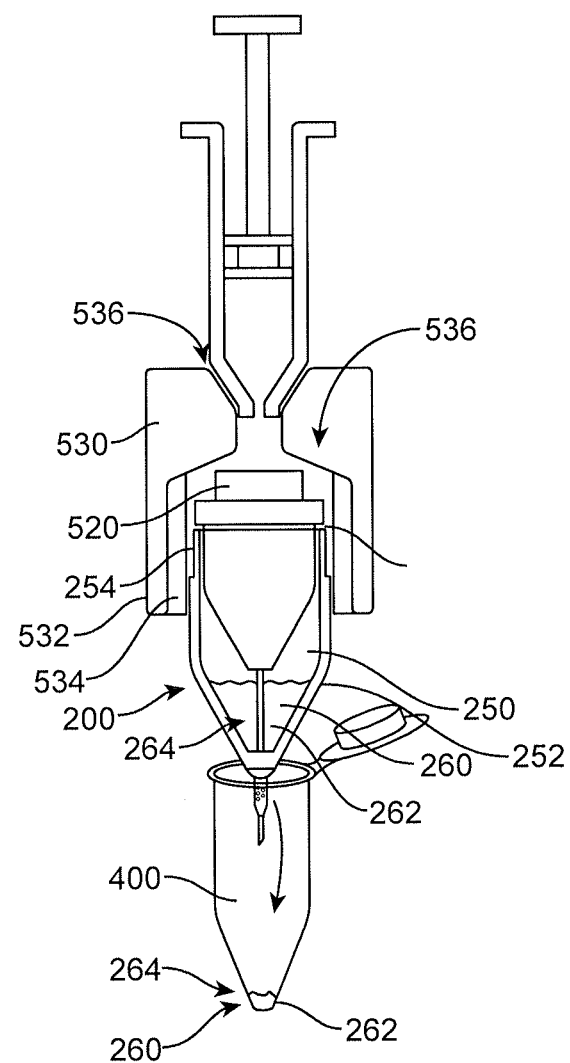
FIG. 16 shows an embodiment of the exchange apparatus placed within a receptacle to couple the receiver container with a syringe to displace the sample fluid from the receiver container into a sample container for analysis.

FIG. 16 shows the exchange apparatus placed within receptacle 536 of the coupling 530 so as to couple the receiver container 250 with the syringe 540. The syringe 540 can pressurize the channel 254 so as to displace the implantable device fluid comprising the sample fluid 264 from the receiver container 250 into a sample container 400 for analysis. The annular protrusion 534 can engage the outer wall 252 of the exchange apparatus 200 form a seal and pressurize chamber 250 when the plunger of syringe 540 is depressed. The pressurization of chamber 250 urges the implantable device fluid 262

FIG. 17 shows an exchange apparatus 200 coupled to a removable receiver container 250. The removable container 250 may comprise a penetrable barrier, for example a septum. The exchange apparatus 200 can be coupled to a syringe 300. The exchange apparatus can be coupled to a device 100 implanted in an eye with the elongate structure 201 configured to extend through the conjunctiva 16 and the penetrable barrier 184. The exchange apparatus may comprise a first channel coupled to the plurality of openings to receive the fluid from the implantable device, and a second channel coupled to a vent. The first channel 239 may extend to a first needle 710 to puncture container 250 and the second channel may extend to a second needle 720 to puncture the container 250. The first needle may have a first opening 712, and the second needle may have a second opening 722. The first opening can be located below the second opening, such that the second opening allows air to pass when liquid passes through the first opening.

Figure 18:
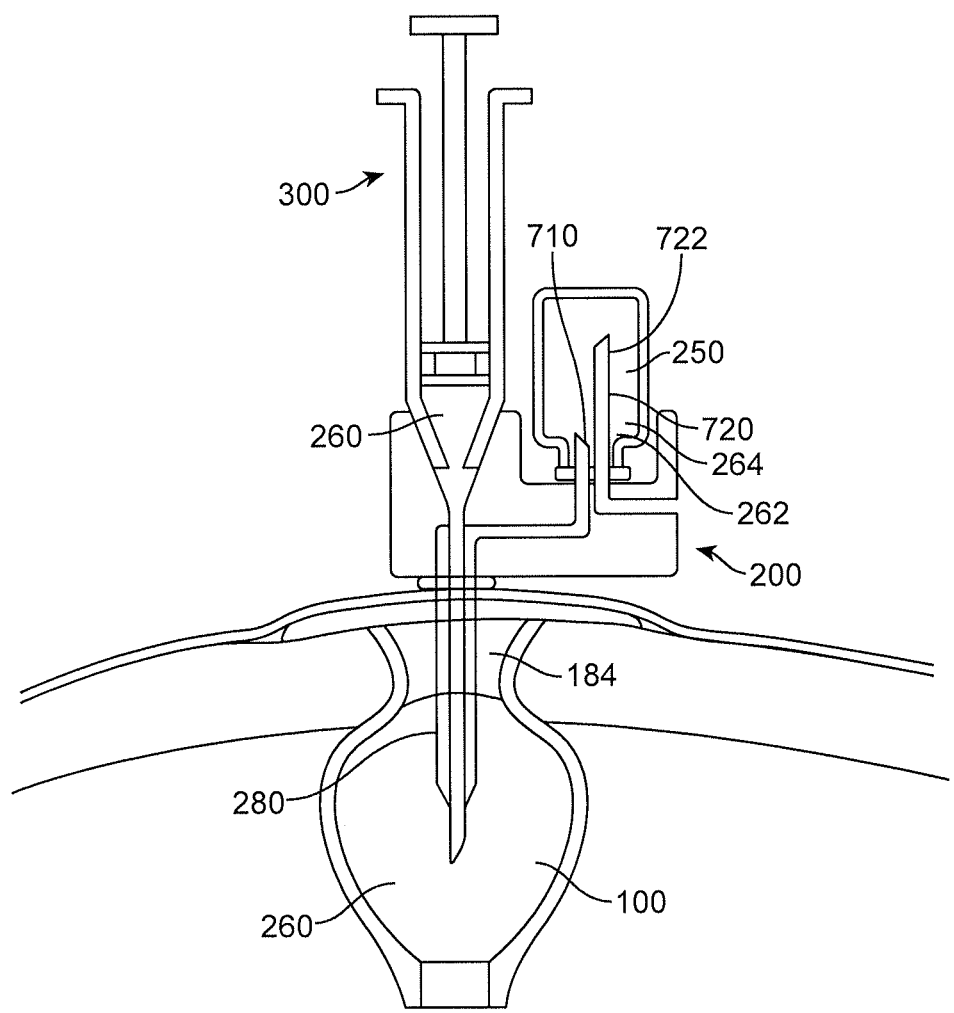
FIG. 18 shows an embodiment of the exchange apparatus coupled to an implanted device to exchange fluid and receive fluid from the implanted device.

FIG. 18 shows the exchange apparatus 200 coupled to the implanted device 100 so as to exchange fluid and receive sample fluid 264 from the implanted device. The container 250 can be coupled to the exchange apparatus during exchange.

Figure 19:
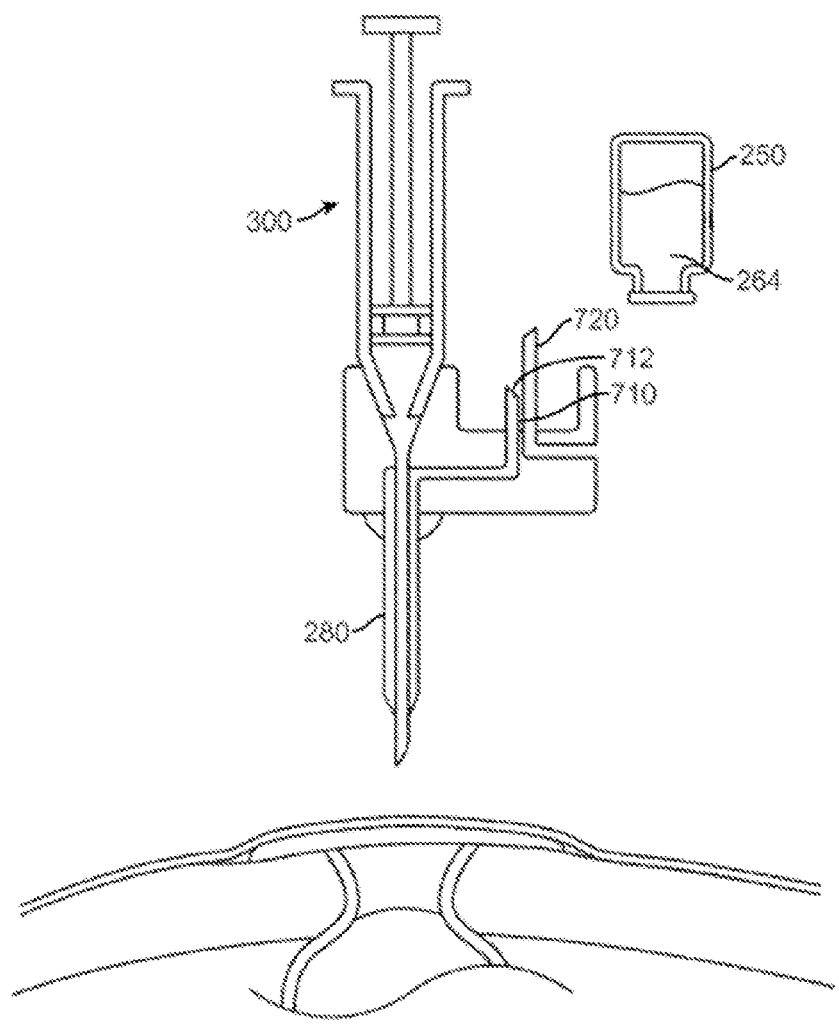
FIG. 19 shows an embodiment of the exchange apparatus removed from the implanted device and the receiver container detached from the exchange apparatus.

FIG. 19 shows the exchange apparatus removed from the implanted device and the receiver container 250 detached from the exchange apparatus. The sample fluid 264 from the implantable device can be contained within the container 250.

Figure 20B:
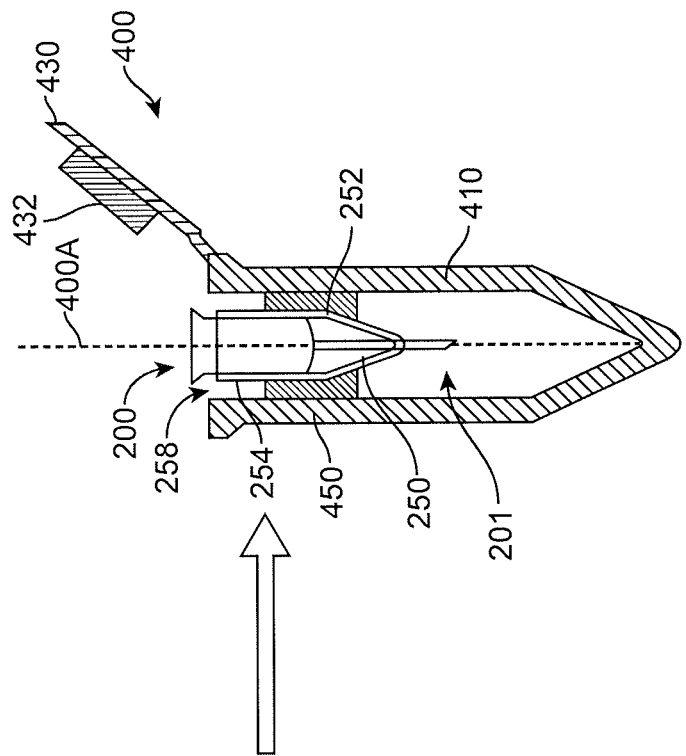
FIG. 20B shows an embodiment of an exchange apparatus placed in the container having components as in FIG. 20A.
Figure 20A:
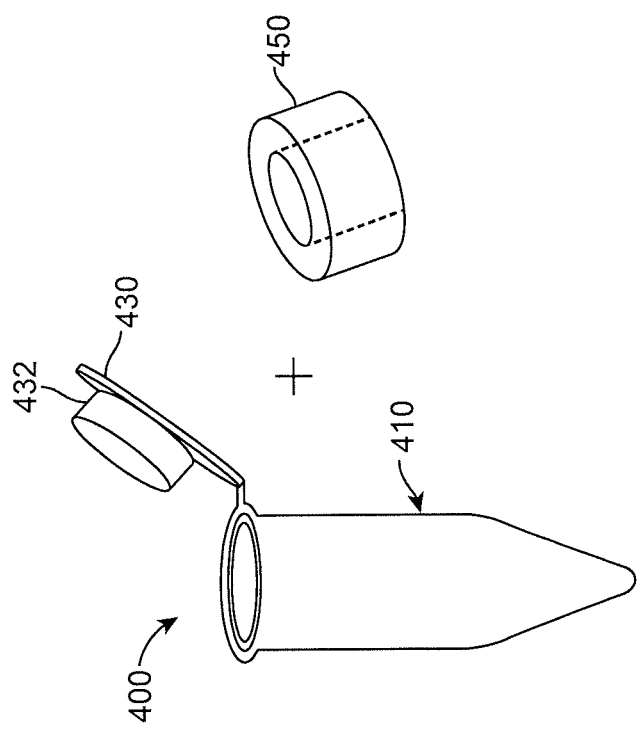
FIG. 20A shows an embodiment of components of a container to remove a sample fluid from an exchange apparatus.

FIG. 20A shows components of a container 400 to remove a sample fluid 264 from exchange apparatus 200. The container 400 may comprise a sealable container having a wall composed of a barrier material 410 to inhibit evaporation, a cap 430 and an annular protrusion 432. A support 450 can be placed within container to receive and hold the exchange apparatus 200 within the container. The support 450 may comprise a piece of soft elastomeric tubing such as silicone tubing, for example.

FIG. 20B shows an exchange apparatus 200 placed in the container 400 having components as in FIG. 20A. The exchange apparatus is placed such that the wall 252 of container 250 rests on the support 450. The elongate structure 201 extends below the support 450. The container 400 comprises an axis 400A, which axis may be aligned with the axis of exchange apparatus 200. The opening 258 coupled to container 250 with channel 254 is exposed to air.

Figure 20C:
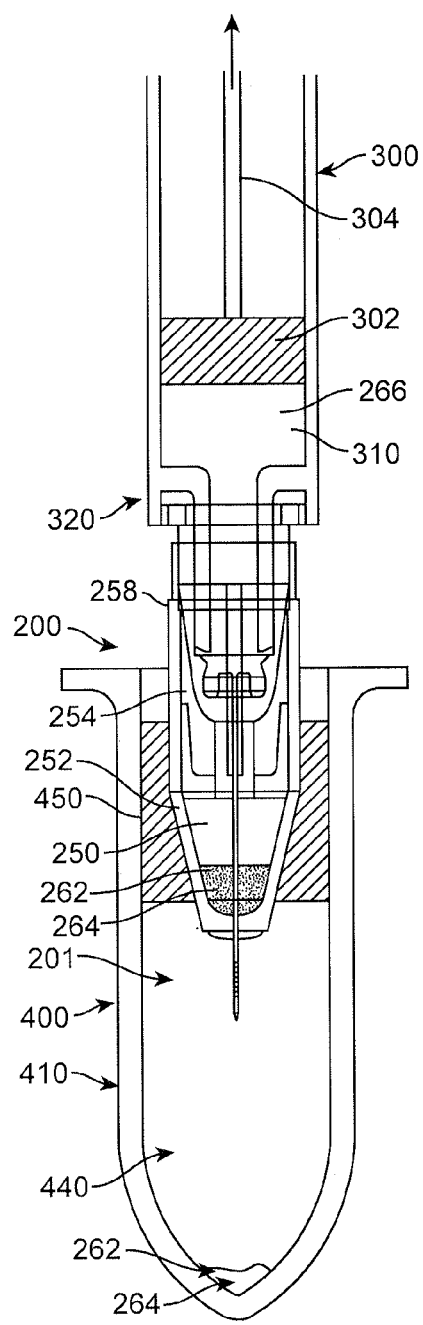
FIGS. 20C and 20D show an embodiment of removal of a sample fluid from an exchange apparatus with the sample fluid drawn into the container as in FIG. 20B.
Figure 20D:
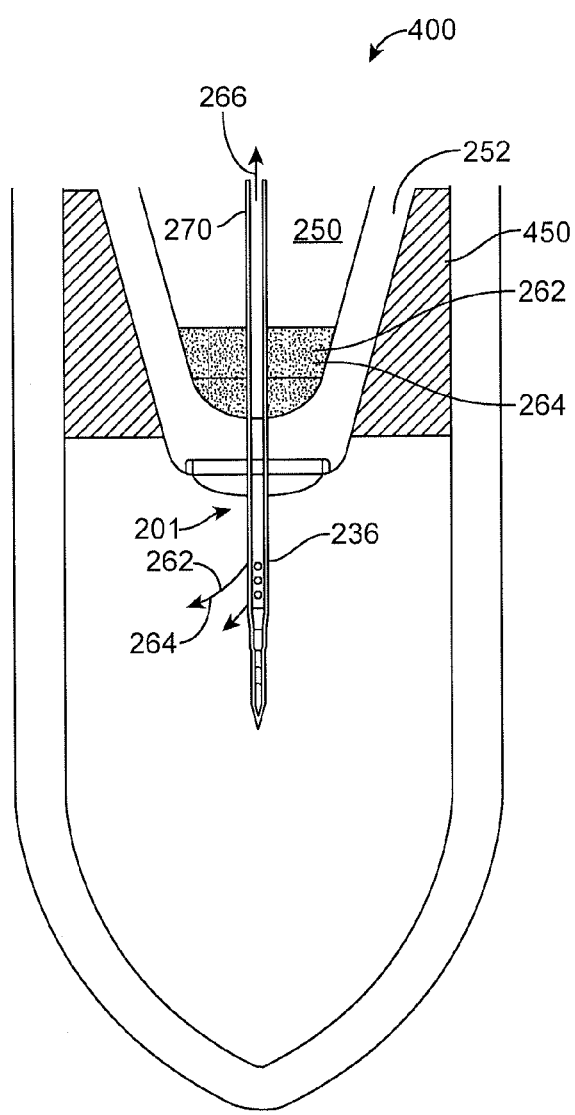

FIGS. 20C and 20D show removal of implantable device fluid 262 comprising sample fluid 264 from exchange apparatus. The sample fluid 264 may be drawn into the container 400 with aspiration. A syringe 300 can be coupled to the exchange apparatus 200 with a connector 320 such as a locking connector, for example. The syringe 300 may comprise a piston 302 connected to a plunger 304 which allows the piston to be advanced and pulled back. The syringe 300 comprises a chamber 310 having a volume defined with the location of piston 302.

The piston of the syringe can be drawn outward to draw air from chamber 440, which chamber draws sample fluid 264 into chamber 440.

Figure 21:
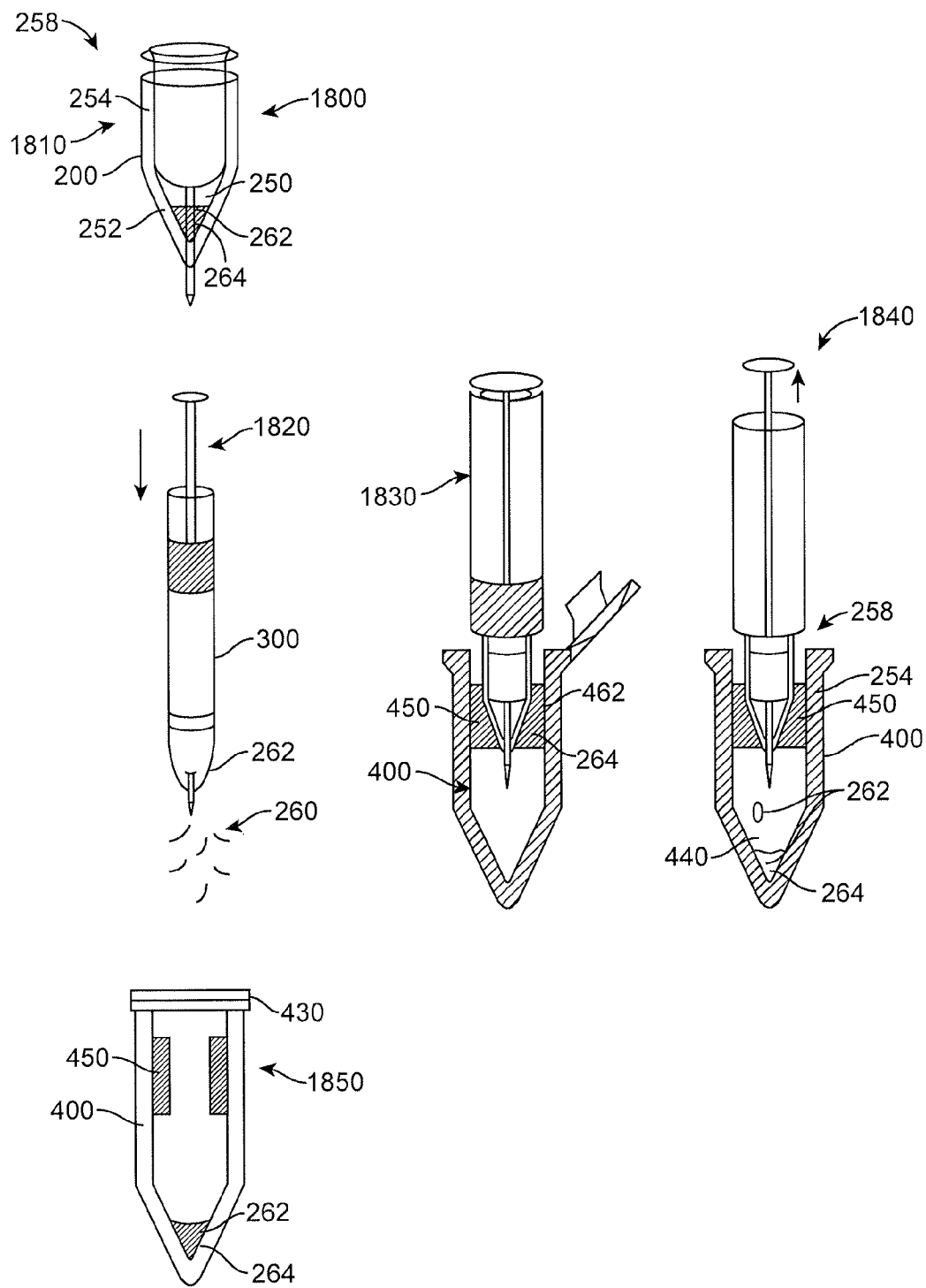
FIG. 21 shows an embodiment of a method of removal from an exchange apparatus with a removal container as in FIGS. 20A to 20D.

FIG. 21 shows a method 1800 of removal from an exchange apparatus with a removal container as in FIGS. 20A to 20D. A step 1810 removes the exchange apparatus 200 from the syringe after injection of the therapeutic fluid. The implantable device fluid comprising the sample fluid is contained in the receiver container 250.

A step 1810 removes therapeutic fluid 260 from the needle of the elongate structure 201 with injection of a gas comprising air from a syringe 300.

A step 1820 depresses the plunger towards the needle.

A step 1830 places the exchange apparatus 200 on the support 450 of container 400 with the exchange apparatus coupled to syringe 300. The support 450 coupled to exchange apparatus 200 may define a chamber 440. The support 450 can be shaped to inhibit air flow between and outer surface of the exchange apparatus and an inner surface of the support 450, for example with a seal formed between the outer surface of the exchange apparatus 200 and the inner surface of the support 450. The support may comprise a soft material, such as a soft elastomeric material, for example.

A step 1840 draws air from chamber 440 with syringe 300 through the injection needle of the elongate structure extending into chamber 440. The implantable device fluid 262 comprising sample fluid 264 is displaced from the receiver container with air drawn into the receiver container 250 through opening 258 of channel 254. The implantable device fluid 262 comprising sample fluid 264 falls to the lower end of chamber 440 and is contained on an inner surface of container 400.

A step 1850 removes the exchange apparatus 200 and syringe 300 from the sample container 400. The cap 430 is placed on the container 400, so as to inhibit evaporation of the implantable device fluid 260 comprising sample fluid 264.

Figure 22:
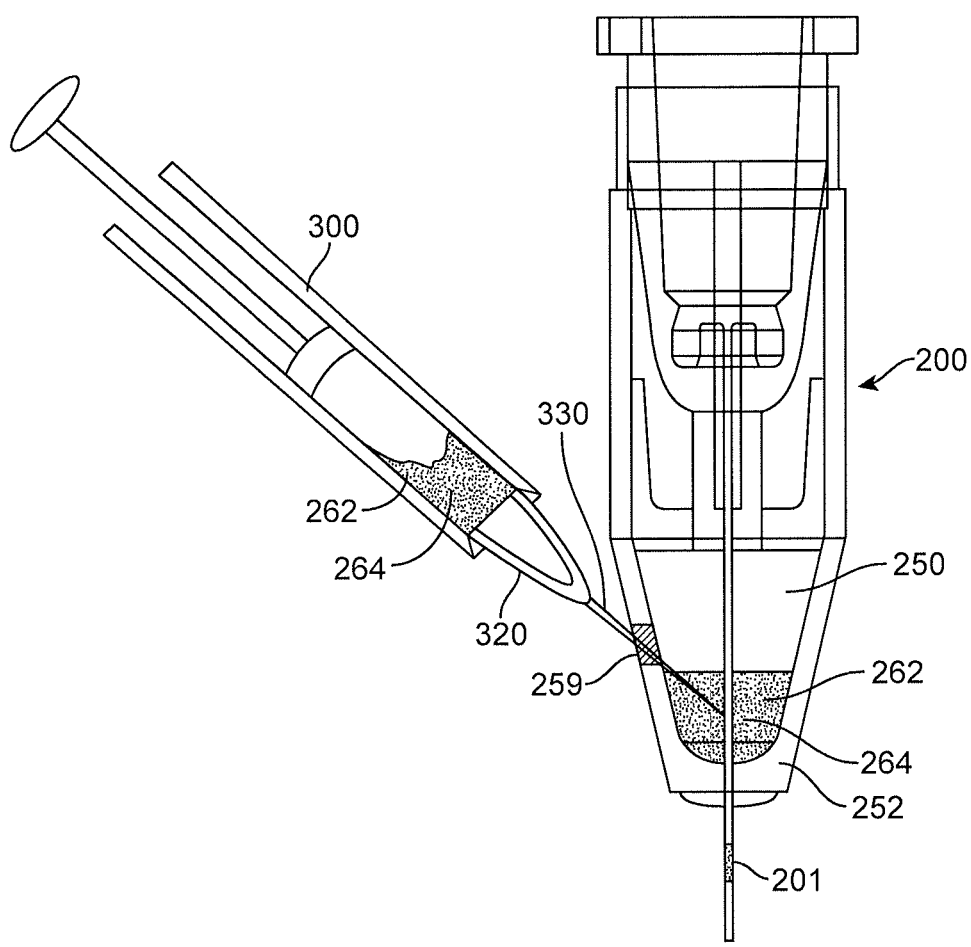
FIG. 22 shows an embodiment of an exchange apparatus having a receiver container comprising a penetrable barrier on a side port to remove a sample from the receiver container with a needle and syringe.

FIG. 22 shows an exchange apparatus 200 having a receiver container 250 comprising a penetrable barrier structure 259 on a side port to remove a sample from the receiver container with a needle and syringe. The syringe can draw implantable device fluid 262 comprising sample fluid 264 from the receiver container 250 through a needle 330 passing through the penetrable barrier structure 259 on the side port.

Figures 23A, 23B:
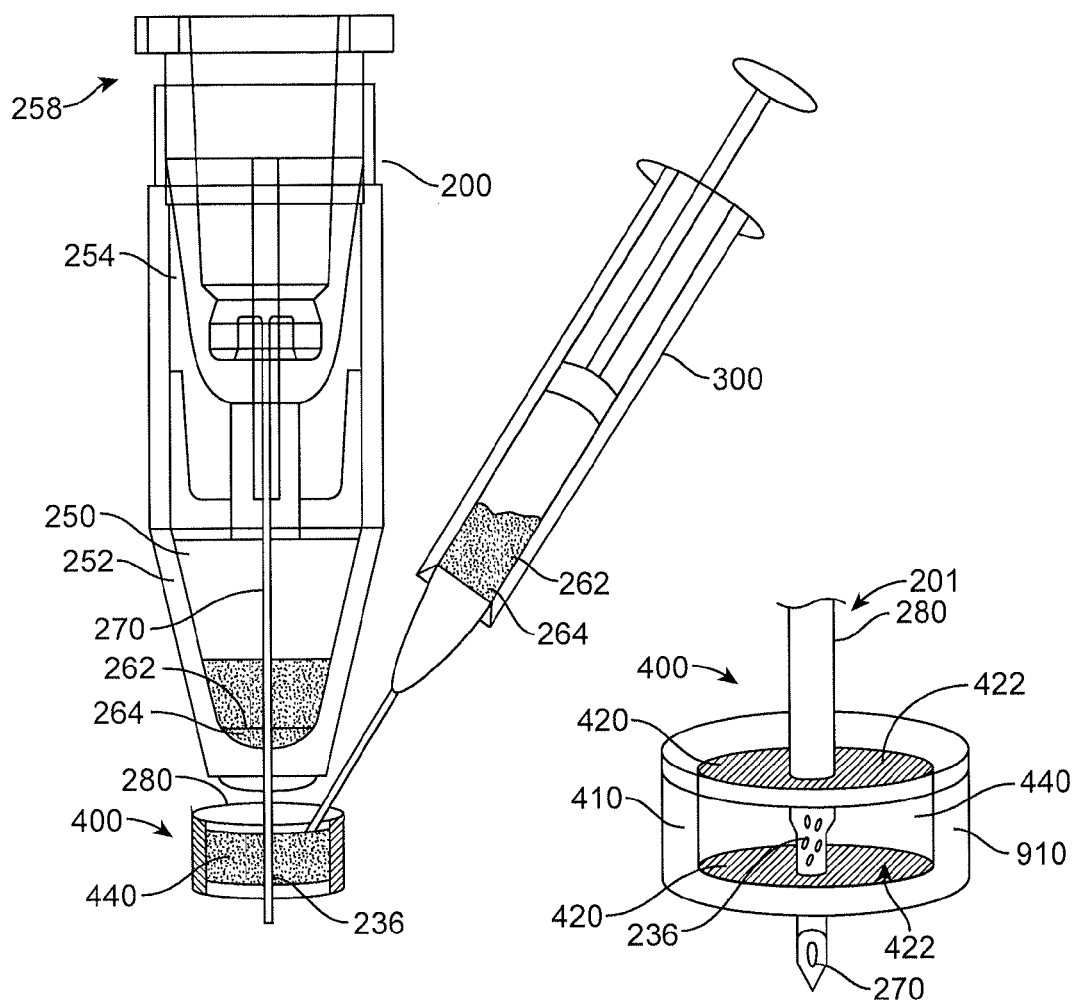
FIG. 23A shows an embodiment of an exchange apparatus having a receiver container coupled to a sample container and a syringe to displace fluid from the receiver container.
FIG. 23B shows the sample container of FIG. 23A placed over the plurality of openings of the exchange apparatus.

FIG. 23A shows an exchange apparatus 200 having a receiver container 250 coupled to a sample container 400 and a syringe 300 to displace fluid from the receiver container 250. The sample container 400 is placed over the plurality of openings 236 and a needle 330 of a syringe 300 extends into a chamber 440 the sample container. The syringe 300 can draw fluid from chamber 440 so as to displace fluid from the receiver container 250. The channel 254 extends from container 250 to opening 258. Fluid drawn through needle 330 into syringe 300 urges the implantable device fluid 262 comprising sample fluid 264 through the one or more openings comprising the plurality of openings 236, and air can move inward through opening 258 and along channel 254 to displace the implantable device fluid 262 comprising sample fluid 264. The needle 270 extends through the sample container 400 such that the distal end of the needle extends beyond sample container 400. The plurality of openings 236 may comprise a plurality of openings of sheath 280.

FIG. 23B shows the sample container 400 of FIG. 23A placed over the plurality of openings 236 of the exchange apparatus. The sample container 400 may comprise a first penetrable barrier comprising penetrable barrier material 420 and a second penetrable barrier comprising penetrable barrier material 420. A first septum 422 can be located opposite a second septum 422, for example. The elongate structure 201 can extend through the first penetrable barrier and the second penetrable barrier so as to position the one or more openings between the first penetrable barrier and the second penetrable barrier. The sample container 400 may comprise a wall composed of a barrier material 410, and the wall may comprise an amount of rigidity sufficient to resist deflection when the sample is drawing with needle 330. The wall may comprise an annular shape, for example a tubular geometry. The needle 270 may extend through the second penetrable barrier so as to inhibit fluidic coupling of the syringe 300 and needle 330 with the opening on the distal end of needle 270. The sample container 400 can be shaped in many ways, for example with a spherical ball or other shape having a walls composed of penetrable barrier material 410 such that the needle tip can extend through both side of the container 400.

Figure 24A:
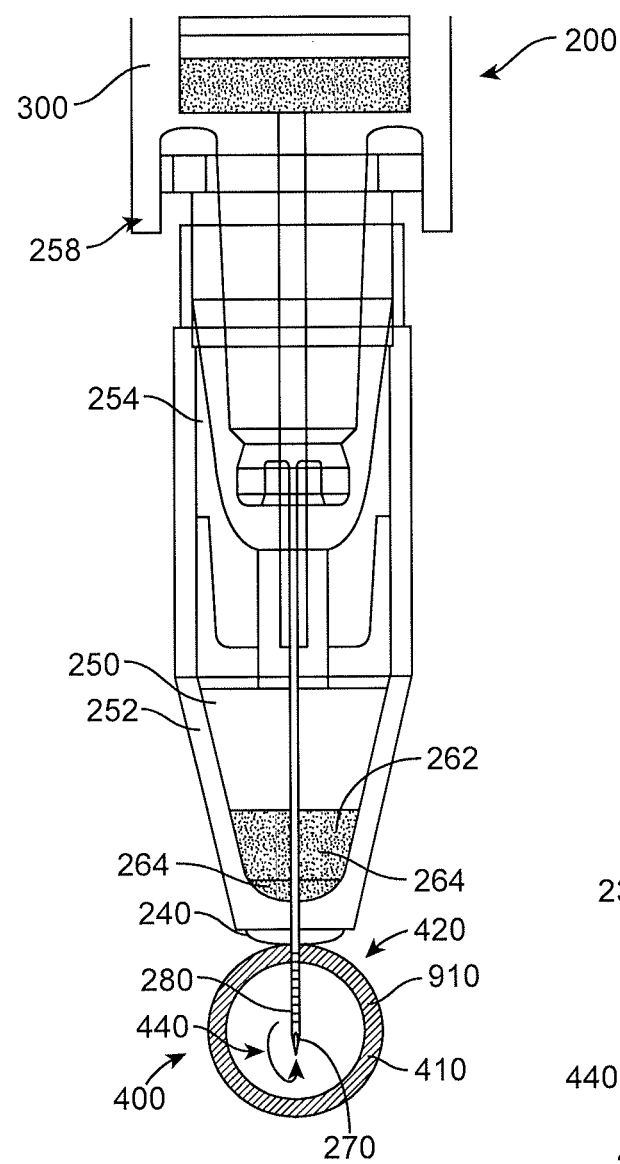
FIG. 24A shows an embodiment of an exchange apparatus having a receiver container coupled to a syringe with a sample container placed over openings of the exchange apparatus so as to remove a sample from the receiver container.
Figure 24B:
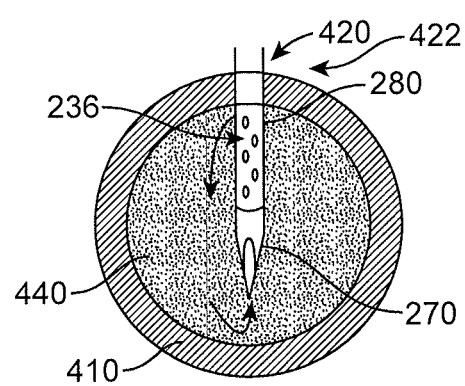
FIG. 24B shows an embodiment of the sample container of FIG. 24A placed over the plurality of openings of the exchange apparatus and the opening to the injection needle.

FIGS. 24A and 24B show an exchange apparatus having a receiver container 250 coupled to a syringe 300 with a sample container 400 placed over openings 236 of the exchange apparatus 200 so as to remove a sample fluid 264 from the receiver container 250. The sample container 400 comprises a chamber 440 enclosed with a wall comprising a barrier material 410 and a penetrable barrier material 420, in which the penetrable barrier material may comprise a septum, for example. The wall of the container 400 may comprise one or more of many shapes such as annular, spherical, cubic, ellipsoidal or oval, for example. The elongate structure 201 comprising needle 270 and sheath 280 can be advanced into the container 400 so as to place at least one opening of the plurality of openings 236 within the chamber 440 and the distal needle tip comprising the opening to place therapeutic fluid within the chamber 440. The needle can be coupled to syringe 300, and fluid drawn from chamber 440 with syringe 300 through an opening in the distal tip of needle 270. The fluid drawn through the needle 270 is replaced with the fluid passed through the plurality of openings 236.

The receiver container 250 comprising the implantable device fluid 262 comprising sample fluid 264 is fluidically coupled to the plurality of openings as described herein such that the implantable device fluid 262 comprising the therapeutic fluid 264 is passed through the plurality of openings. The channel 254 extends from the receiver container 250 to the opening 258 such that air may be drawn into the receiver container 250 to replace the volume of the displaced implantable device fluid 262 comprising sample fluid 264. In many embodiments, the implantable device fluid 262 comprising the sample fluid 264 comprises a liquid comprising water as described herein.

FIG. 25A shows an exchange apparatus 200 comprising a removable receiver container 250 comprising a removable sheath 280 placed over a needle 270. The receiver container 250 may comprise the sample container 400. The wall 252 of container 250 and needle 270 can be configured for removal and separation from the needle 270 so as to provide the sample container 400. The sheath 280 may be supported on a distal end of the wall 252 of container 250, such that the sheath 280 can be supported with the wall 252 of container 400 when removed. A plug 960 comprising penetrable barrier material 420 can be placed over the sheath 280 needle 270 prior to removal of the needle to inhibit leakage of the implantable device fluid 262 comprising sample fluid 264.

FIG. 25B shows the removable container 400 of FIG. 25A with a plug 960 comprising penetrable barrier material 420 placed over the sheath 280 and the needle 270 removed, such that the sheath 280 is supported with the container 400. The implantable device fluid 262 comprising sample fluid 264 remain in the receiver container 250 comprising sample container 400 subsequent to removal of the needle 200.

FIG. 25C shows the removable container of FIGS. 25A and 25B with plug 960 placed over the sheath 280 and a cap 430 over the removable receiver container. The cap 430 can inhibit one or more of evaporation or leakage of the implantable device fluid 262 comprising sample fluid 264.

FIGS. 26A to 26E show a centrifuge used to remove the fluid sample from the receiver container of the exchange apparatus.

Figure 26A:
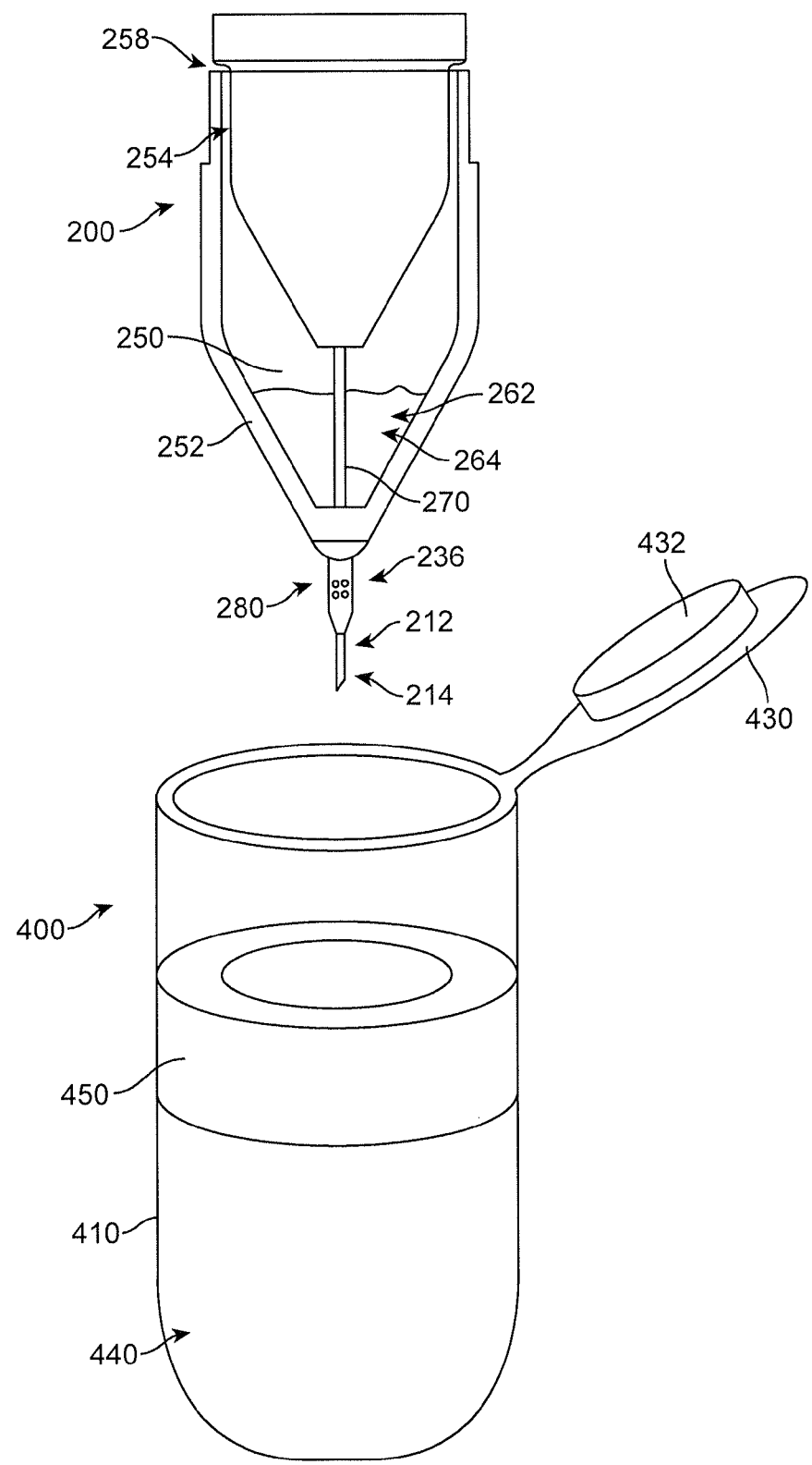

FIG. 26A shows the exchange apparatus 200 comprising the receiver container 250 having the implantable device fluid 262 comprising the sample fluid 264 contained therein, in which the exchange apparatus is configured for placement within the sample container 400. The sample container 400 may comprise a centrifuge tube having a support 450 as described herein. The exchange apparatus 200 may comprise a channel 254 extending from receiver container 450 to opening 258, so as to couple the opening 258 to the plurality of openings 236. As the implantable device fluid 262 comprising sample fluid 264 contained within receiver container 250 comprises a density greater than air, the fluid within the receiver container can be displaced through the plurality of openings 236 of the exchange apparatus 200. Air can pass through opening 258 and channel 254 into the receiver container 250 to replace the volume of implantable device fluid 262 comprising sample fluid 264 displaced from receiver container 250 and through the plurality of openings 236.

Figure 26B:
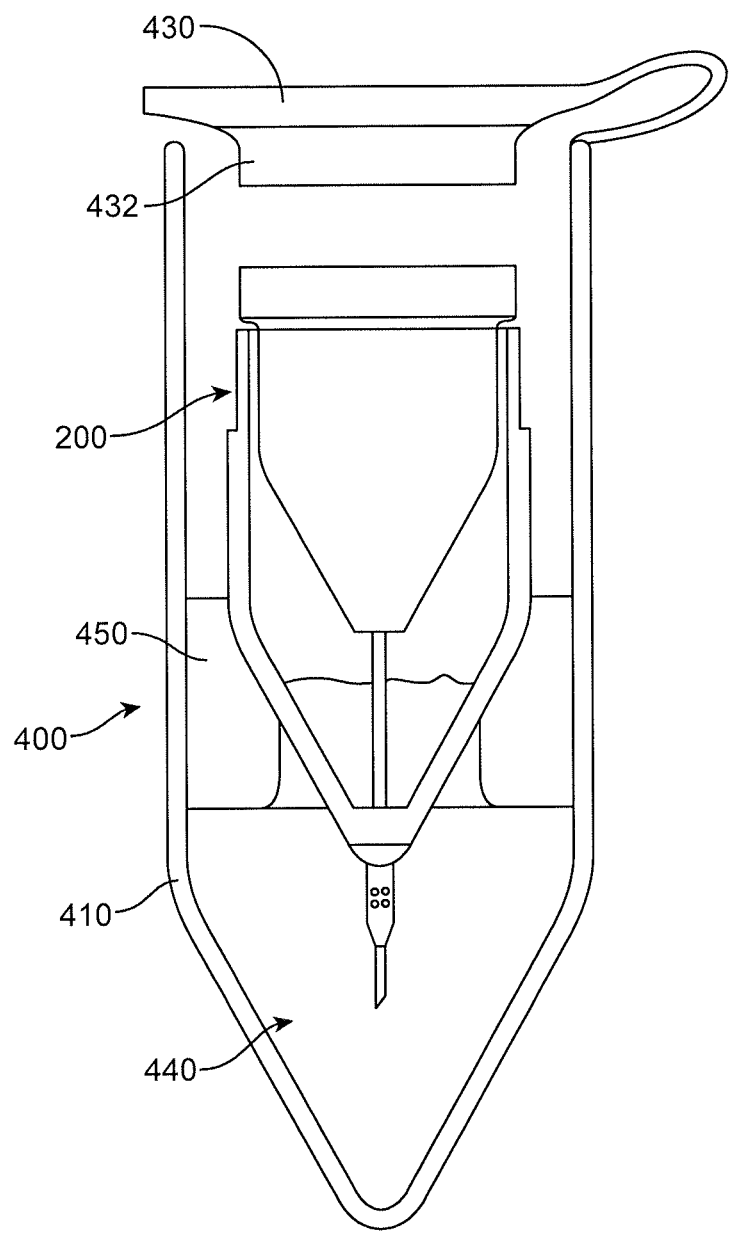

FIG. 26B shows the exchange apparatus 200 placed in the sample container 400.

Figure 26C:
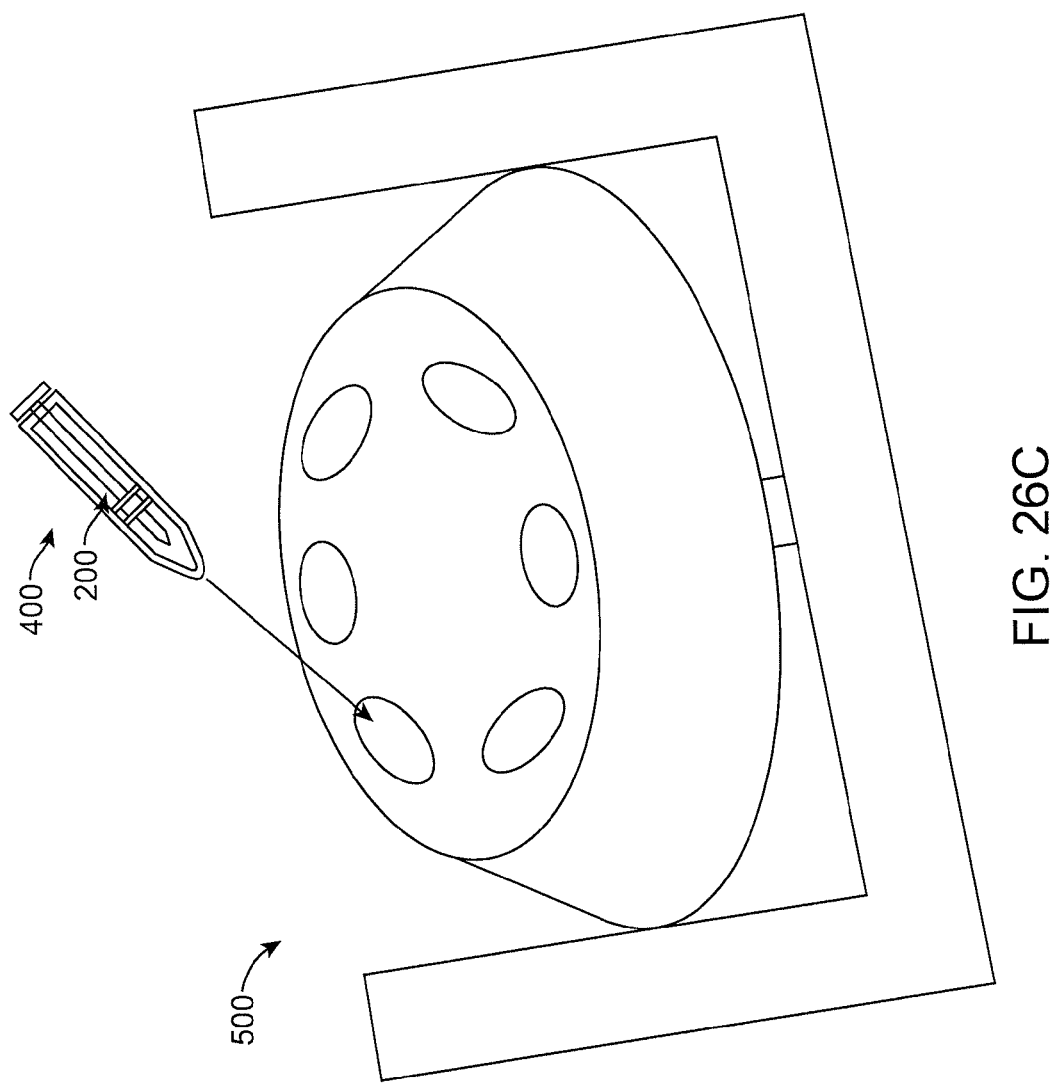

FIG. 26C shows the exchange apparatus 200 in the sample container 400 configured for placement in a centrifuge 500.

FIG. 26D shows the exchange apparatus 200 in the sample container 400 placed in a centrifuge 500.

Figure 26E:
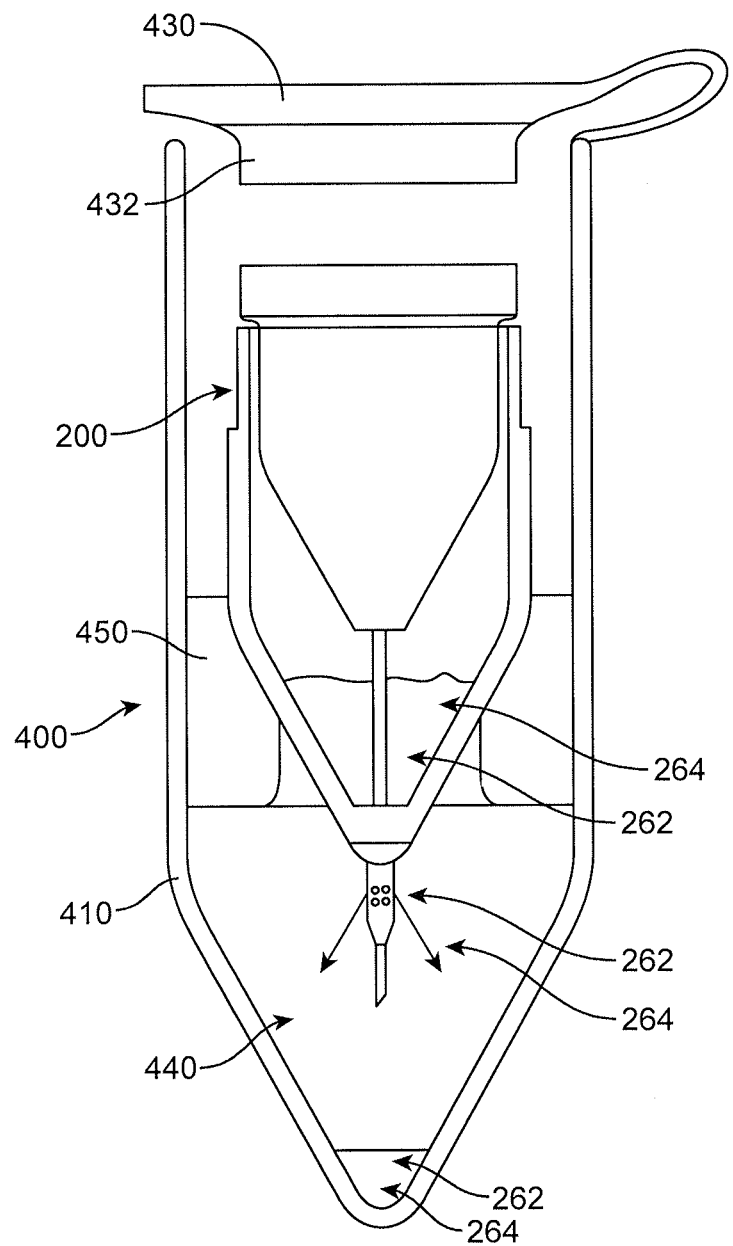

FIG. 26E shows the exchange apparatus 200 within the sample container 400 subjected to force within the centrifuge 500, such that the force of the centrifuge 500 is sufficient to displace the implantable device fluid 262 comprising sample fluid 264 from the receiver container 400 through the plurality of openings 236 as described herein. The implantable device fluid 262 comprising sample fluid 264 is deposited on the lower end portion of an inner surface the sample container 400.

FIG. 26F shows an embodiment comprising exchange apparatus 200 placed in a sample container 400 comprising a centrifuge tube. The container 400 may comprise a barrier material 410 to inhibit evaporation from within the container to the outside environment, a cap 430 and a base supporting a soft penetrable material as described herein. The cap 430 may comprise a protrusion such as an annular protrusion 432 to seal around an outer portion of the wall of the container, for example. When the cap 430 is placed on the top of the tube, the chamber 440 can be sealed so as to inhibit evaporation, for example. The barrier 410 may comprise sufficient strength so as to inhibit penetration with the needle of the elongate structure 201 when placed in a centrifuge, for example.

FIG. 26G shows an embodiment comprising an exchange apparatus 200 placed in a sample container 400 comprising a centrifuge tube, in which the centrifuge tube comprises a support 450 comprising an annular shoulder 450S of the tube to engage and hold the exchange apparatus. The support 450 can engage the exchange apparatus 200 to support the exchange apparatus in a centrifuge, for example, with a gap extending between the lower surface of the tube and the distal tip of the needle of the exchange apparatus so as to inhibit penetration of the sample container with the needle. The container 400 may comprise additional structures as described herein.

Figure 27A:
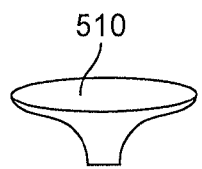
FIG. 27A shows an embodiment of a collapsible fluid separator for use with a therapeutic device.

FIG. 26H shows an embodiment of an exchange apparatus 200 placed in a sample container 400 comprising a centrifuge tube, in which the centrifuge tube comprises a support 450 comprising restricted portion to hold the exchange apparatus. The support 450 may comprise a rib to engage the exchange apparatus 400, for example. The rib 450R can be formed with a recess in the outer surface of the container 400. The support comprising the rib can engage and support the exchange apparatus such that a gap extends between the distal end of elongate structure 201 and the lower surface of the tube FIG. 27A shows an embodiment of a collapsible fluid separator 510 for use with a therapeutic device. The collapsible fluid separator 510 may comprise a plunger and can be penetrable with a needle and configured to form a seal around the outer perimeter. The fluid separator 510 may comprise a distal shape profile corresponding to the distal portion of the reservoir chamber so as to displace fluid from the distal portion near the porous structure 150 as described herein. The fluid separator 510 may be penetrated with a needle and may comprise a septum, for example. The penetrable fluid separator can be penetrated with a needle for fluid removal and refill. In many embodiments, the fluid separator 510 is configured to expand and contract so as to contact the inner wall of the reservoir chamber 140 and form a seal with wall of the reservoir chamber. The fluid separator 510 can be configured to expand and contract to maintain contact with a wall having a varying cross-sectional dimension such as a varying diameter. In many embodiments, the fluid separator 510 is configured to contract so as to decrease the volume of the fluid separator such that the volume of the reservoir chamber available to receiver therapeutic fluid 260 can be substantially maintained.

Figure 27B:
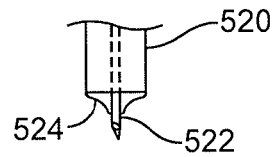
FIG. 27B shows an embodiment of a plunger comprising an exchange needle and a shoulder suitable for use with the collapsible fluid separator as in FIG. 27A and a therapeutic device.

FIG. 27B shows an embodiment of plunging structure 520 comprising an exchange needle 522 and an engagement structure comprising shoulder 524 suitable for use with the collapsible fluid separator as in FIG. 27A and a therapeutic device. The needle 522 comprises an internal channel to receiver fluid to remove the implantable device fluid and place the therapeutic fluid in the reservoir chamber. The plunging structure may comprise an engagement structure, for example shoulder 524, so as to engage the collapsible separator and advance the fluid separator 510 distally toward the porous structure with a thrusting movement.

Figure 27C:
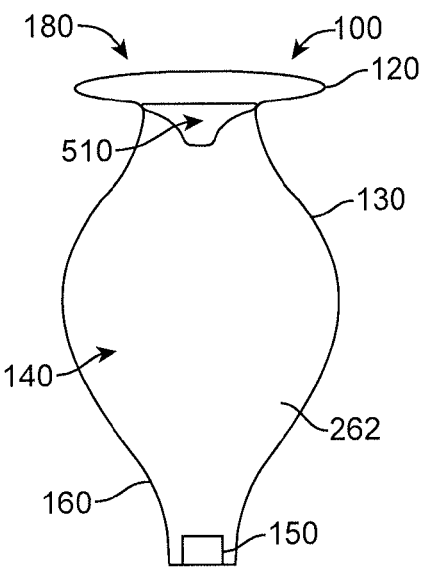
FIG. 27C shows an embodiment of the collapsible fluid separator as in FIG. 27B placed within a reservoir chamber of a therapeutic device.

FIG. 27C shows an embodiment of the collapsible fluid separator as in FIG. 27B placed within a reservoir chamber 140 of a therapeutic device 100. The collapsible separator 510 is shown near the proximal end of the implantable therapeutic device 100, which comprises the access port 180 and retention structure 120. The access port 180 may comprise a penetrable barrier 184 capable of penetration with the needle of the plunging structure, or a removable structure such as a cap, plug or the like which can be removed to introduce the plunging structure.

Figure 27D:
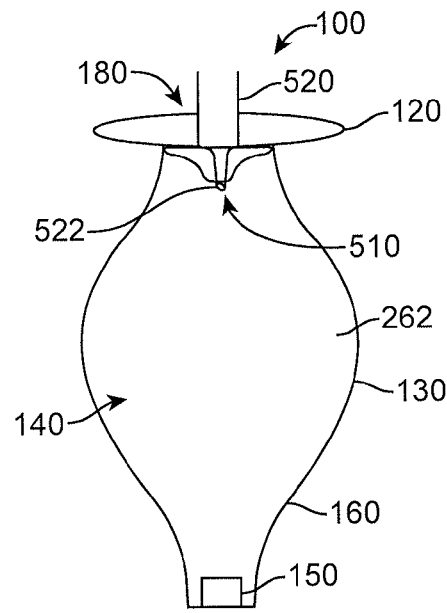
FIG. 27D shows an embodiment of the plunger comprising the exchange needle and the shoulder as in FIG. 27B advanced into the access port of the therapeutic device having the collapsible fluid separator placed within the reservoir chamber of the therapeutic device as in FIG. 27C.

FIG. 27D shows an embodiment of the plunger 520 comprising the exchange needle and shoulder as in FIG. 27B advanced into the access port 180 of the therapeutic device having the collapsible fluid separator 510 placed within the reservoir chamber 140 of the therapeutic device as in FIG. 27C.

Figure 27E:
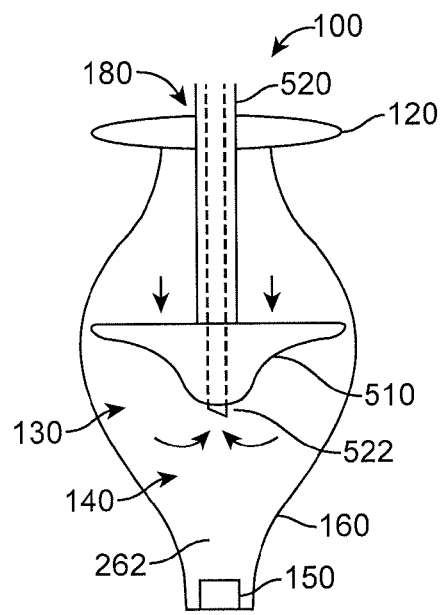
FIG. 27E shows an embodiment of the collapsible fluid separator advanced within the reservoir chamber of the therapeutic device as in FIG. 27D so as to displace the implantable device fluid from the reservoir chamber through the needle.

FIG. 27E shows an embodiment of the plunging structure 520 and collapsible fluid separator 510 advanced within the reservoir chamber 140 of the therapeutic device as in FIG. 27D so as to displace the implantable device fluid 562 from the reservoir chamber through the needle. The collapsible fluid separator 510 has expanded from a first cross-sectional dimension across, for example a first diameter, to a second cross-sectional dimension across, for example a second cross-sectional diameter larger than the first. The expandable and collapsible fluid separator 510 can expand or collapse so as to contact the side wall of the reservoir chamber 140 and inhibit flow between a lower side and an upper side of the expandable and collapsible fluid separator 510. The inhibited flow around the outer perimeter of the fluid separator can provide pressurization of the implantable device fluid near the tip of exchange needle 522 so as to drive implantable device fluid into the exchange needle. Alternatively or in combination, suction can be applied to the exchange needle so as to draw implantable fluid from the exchange needle 522 and advance the separator 510 toward the porous structure 150. In many embodiments, the porous structure 150 comprises a resistance to flow sufficient to inhibit flow of one or more of the implantable device fluid or the therapeutic fluid through the porous structure during the exchange as described herein.

Figure 27F:
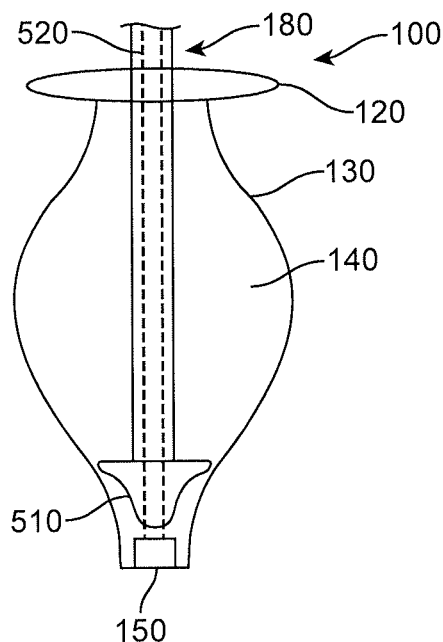
FIG. 27F shows an embodiment of the collapsible fluid separator advanced within the reservoir chamber to a location near the distal end of the reservoir chamber so as to displace most of the implantable device fluid from the reservoir chamber through the needle.

FIG. 27F shows an embodiment of the collapsible fluid separator 510 advanced within the reservoir chamber to a location near the distal end of the reservoir chamber so as to displace most of the implantable device fluid from the reservoir chamber through the needle 522. The needle 522 may contact porous structure 150, which may comprise a rigid porous structure as described herein.

Figure 27G:
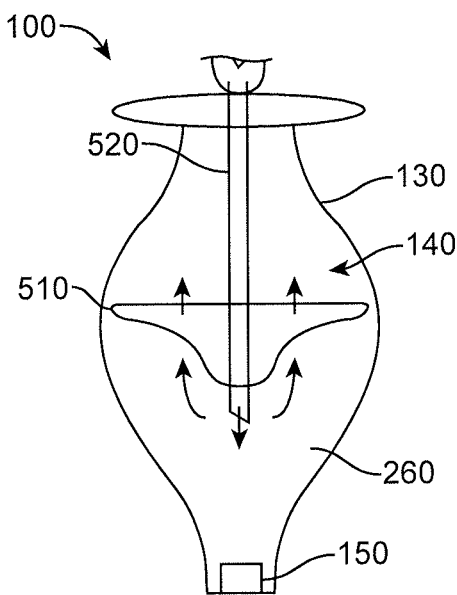
FIG. 27G shows an embodiment of the collapsible fluid separator moved from the distal end of the reservoir chamber so as to place therapeutic device fluid in the reservoir chamber.

FIG. 27G shows an embodiment of the collapsible fluid separator 510 moved from the distal end of the reservoir chamber comprising porous structure 150. The collapsible fluid separator 510 can be moved in one or more of many ways to place the therapeutic fluid in the distal portion of the reservoir container. The therapeutic fluid can be injected through the needle 522, or another needle for example, so as to place the therapeutic fluid 260 in the distal portion of the container. Alternatively or in combination, the expandable and collapsible fluid separator can be pulled toward the proximal end of the reservoir chamber so as to draw therapeutic device fluid through the needle and into the reservoir chamber from an external container of the exchange apparatus as described herein.

Figure 27H:
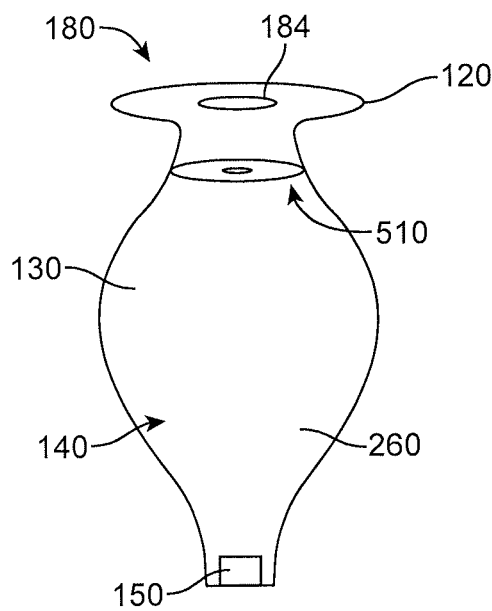
FIG. 27H shows an embodiment of the collapsible fluid separator moved from the distal end of the reservoir chamber to the proximal end of the reservoir chamber so as to fill substantially the reservoir chamber.

FIG. 27H shows an embodiment of the collapsible fluid separator 510 moved from the distal end of the reservoir chamber to the proximal end of the reservoir chamber so as to fill substantially the reservoir chamber with therapeutic fluid 260. The collapsible fluid separator 510 comprises a substantially decreased size and volume so as to fit substantially within the neck of the reservoir chamber such that a substantial amount of the volume of the reservoir is filled with therapeutic fluid 260.

Figure 27I:
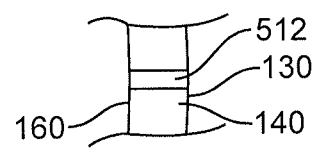
FIG. 27I shows an embodiment of a substantially non-collapsible fluid separator placed within a rigid walled container of a therapeutic device having a substantially fixed cross sectional size.

FIG. 27I shows an embodiment of a substantially non-collapsible fluid separator 510 placed within the reservoir chamber 140 of therapeutic device 100 having a substantially fixed cross sectional size. The container 130 comprising reservoir chamber 140 may comprise a substantially cylindrical tubular barrier 160. The fluid separator may comprise a piston slidable within the tubular barrier 160, for example.

FIG. 28A shows an embodiment of an exchange apparatus 550 comprising a balloon 560 supported on a elongate tubular member 580 capable of introduction into an implantable therapeutic device 100 as to exchange the implantable device fluid 262 with a therapeutic fluid 260.

The exchange apparatus 550 may comprise an elongate tubular structure 570 shaped to penetrate tissue, for example a needle. The elongate tubular structure 570 shaped to penetrate tissue can be advanced into access port 180 through penetrable barrier 184, followed by balloon 560 and the distal end of elongate tubular member 580, such that balloon 560 is placed in the reservoir chamber.

The balloon 560 may comprise a highly compliant balloon. As the balloon 560 is inflated, implantable device fluid is displaced out of the reservoir chamber. The balloon 560 may comprise Pebax™ or another highly elastic material such as silicone, for example, or a non-elastic material capable of being one or more of folded, rolled or compressed, for example. The balloon 560 may comprise a tubular structure and supported on the outside diameter of the needle or a sheath over the needle prior to inflation. The balloon may be designed to inflate proximally to distally, e.g. top down, to contact the inner wall of the reservoir chamber and displace fluid toward the vent needle opening. The balloon may be inflated with therapeutic fluid 260. The balloon may be retractable within a sheath, for example. A sheath may be provided to deliver the balloon through the penetrable barrier, for example with the sheath penetrating the penetrable barrier to protect and place the balloon in the reservoir chamber without substantial contact of the balloon to the penetrable barrier when the balloon is placed.

The exchange apparatus 550 comprises components and structure to inflate balloon 560 and remove implantable device fluid 262 from the reservoir chamber 140. The elongate tubular structure 570 shaped to penetrate tissue may comprise a channel 572 to fluidically couple the reservoir chamber 140 with an external container, for example. The elongate tubular member 580 may comprise a first lumen 582 and a second lumen 584, for example. The elongate tubular member 580 can be connected to one or more containers, syringes, or pumps, for example. The elongate tubular member 580 may comprise a first connector 588 fluidcially coupled to first lumen 582, and a second connector 586 fluidcially coupled to the second lumen 584, for example. The first lumen 582 of the elongate tubular member 580 can fluidically couple to channel 572 and external connector 588, for example, such that the implantable device fluid 262 can be received in a receiver container as described herein. The second lumen 584 can fluidically couple the connector 586 to balloon 560, so as to allow inflation of the balloon, for example with a syringe. The connector 586 and the connector 588 may each comprise standard known connectors as described herein, for example. The exchange apparatus 550 may comprise one or more catheter components known to a person of ordinary skill in the art in the field of catheter design and suitable for commination in accordance with the teachings described herein, for example.

FIG. 28B shows an embodiment of the balloon 260 as in FIG. 28A inflated within the therapeutic device to displace the implantable device fluid 262. The balloon 560 may be inflated with the therapeutic fluid 260 as described herein, for example. The therapeutic fluid 260, or another fluid, can be injected into the balloon with a syringe coupled to connector 586 such that the injected fluid travels along lumen 584 to inflate the balloon 560. The implantable device fluid 262 can be displaced with the balloon so as to urge the implantable device fluid 262 into channel 572 of the elongate structure 260 shaped to penetrate tissue. The porous structure 150 may comprise a substantial resistance to flow to inhibit flow of implantable device fluid 262 through the porous structure.

FIG. 28C shows an embodiment of the balloon 560 deflated within the therapeutic device 100 to provide space for the therapeutic fluid 260. In many embodiments, the receiver container as described herein, for example a bag, can be disconnected from connector 588, and a syringe comprising therapeutic fluid 560 coupled to connector 580. The syringe or other fluid source used to fill balloon 560 can be decoupled from lumen 582, and the therapeutic fluid 560 can be injected into elongate structure 570 to place therapeutic fluid 260 in reservoir chamber 140 such that the fluid within balloon 560 is displaced and the size of balloon 560 decreased. When the size of balloon 560 has decreased sufficiently, the balloon 560 and elongate structure 570 can be removed from the implantable device 100 by passing through the penetrable barrier 184. The balloon 560 and elongate structure 570 can be removed in many ways, for example by one or more of pulling on elongate tubular member 580 or injecting therapeutic fluid 560 into reservoir chamber 140, so as to displace balloon 560 and elongate structure 570 from the reservoir chamber 140. In many embodiments, reservoir chamber 140 can be pressurized with injection of therapeutic fluid 260 so as to displace the balloon 560 and elongate structure 570 through the penetrable barrier 184 with pressure.

FIG. 28D shows an embodiment of the balloon 560 punctured within the therapeutic device 100 so as to release the therapeutic fluid 260 from the balloon to the reservoir chamber 140 of the therapeutic device 100. The therapeutic 100 may comprise internal structures 590 to puncture the balloon and release the therapeutic agent. The internal structure 290 may comprise a sharp tip, for example a needle tip to penetrate the balloon 560 and release the therapeutic agent. The internal structure 590 can be supported on the wall of the reservoir chamber, for example.

FIG. 29A shows an embodiment of a deflectable fluid separator 600 placed within an implantable therapeutic device 100. The deflectable fluid separator 600 inhibits mixing of the implantable device fluid 262 with the therapeutic fluid 260. The deflectable fluid separator 600 can separate portions of the reservoir chamber so as to define a first portion 141 on a first side of the chamber and a second portion 143 on a second side of the reservoir chamber. The first portion 141 of the reservoir chamber 140 may be coupled to a first porous structure 151 to provide sustained release from the first portion and the second portion 143 of the reservoir chamber 140 may be coupled to a second porous structure 153 to provide sustained release from the second portion. The porous structures can be substantially similar to porous structure 150 as described herein. The deflectable fluid separator 600 may comprise a barrier material to inhibit flow of the therapeutic agent, and may comprise one or more of a bladder, diaphragm, a membrane, or a sheet of distensible material, for example. The deflectable fluid separator may comprise an expandable bladder capable of deflection to either side of the reservoir chamber, for example. The deflectable fluid separator may be used with exchange apparatus 200 as described herein. The elongate structure 201 of the exchange apparatus may comprise a bi-needle design as described herein, for example with a first needle to advance fluid into a first side of the bladder and a second needle to receiver fluid from a second side of the bladder, in no particular order, or simultaneously, for example.

FIG. 29B shows an embodiment of the deflectable fluid separator as in FIG. 29A displaced to the second side of the reservoir chamber to remove fluid from the second portion 143 of the reservoir chamber. The removal of fluid from portion 143 can be achieved in many ways. For example, the deflectable fluid separator can be displaced with injection into first portion 141 so as to displace implantable device fluid 262 from second portion 143. A first needle 611 and a second needle 613 can be advanced so as to extend through penetrable barrier 184 into first portion 141 and into second portion 143, respectively. The first needle can inject fluid into first portion 141 to displace fluid from second portion 143. Alternatively or in combination, the second needle 613 can be aspirated to draw fluid from second portion 143 with suction, and a fluid may be drawn into first portion 141 through first needle 611.

FIG. 29C shows an embodiment of the deflectable fluid separator 600 as in FIG. 29B displaced to the first side of the reservoir chamber with a therapeutic fluid 260 placed in the second portion 143 of the reservoir chamber 140. The therapeutic agent 110 contained within second portion 143 can be released through porous structure 153 in a manner similar to porous structure 150 as described herein. When a sufficient amount of therapeutic agent has been released from second chamber 143 for an extended time through porous structure 153, the fluid can be removed from second portion 143 as described herein and a second amount of therapeutic fluid 260 placed in first portion 141 for sustained release for another extended time through porous structure 151. The removal and placement of fluid with the deflectable separator can be repeated as many times as is helpful to treat the patient.

Figure 30A:
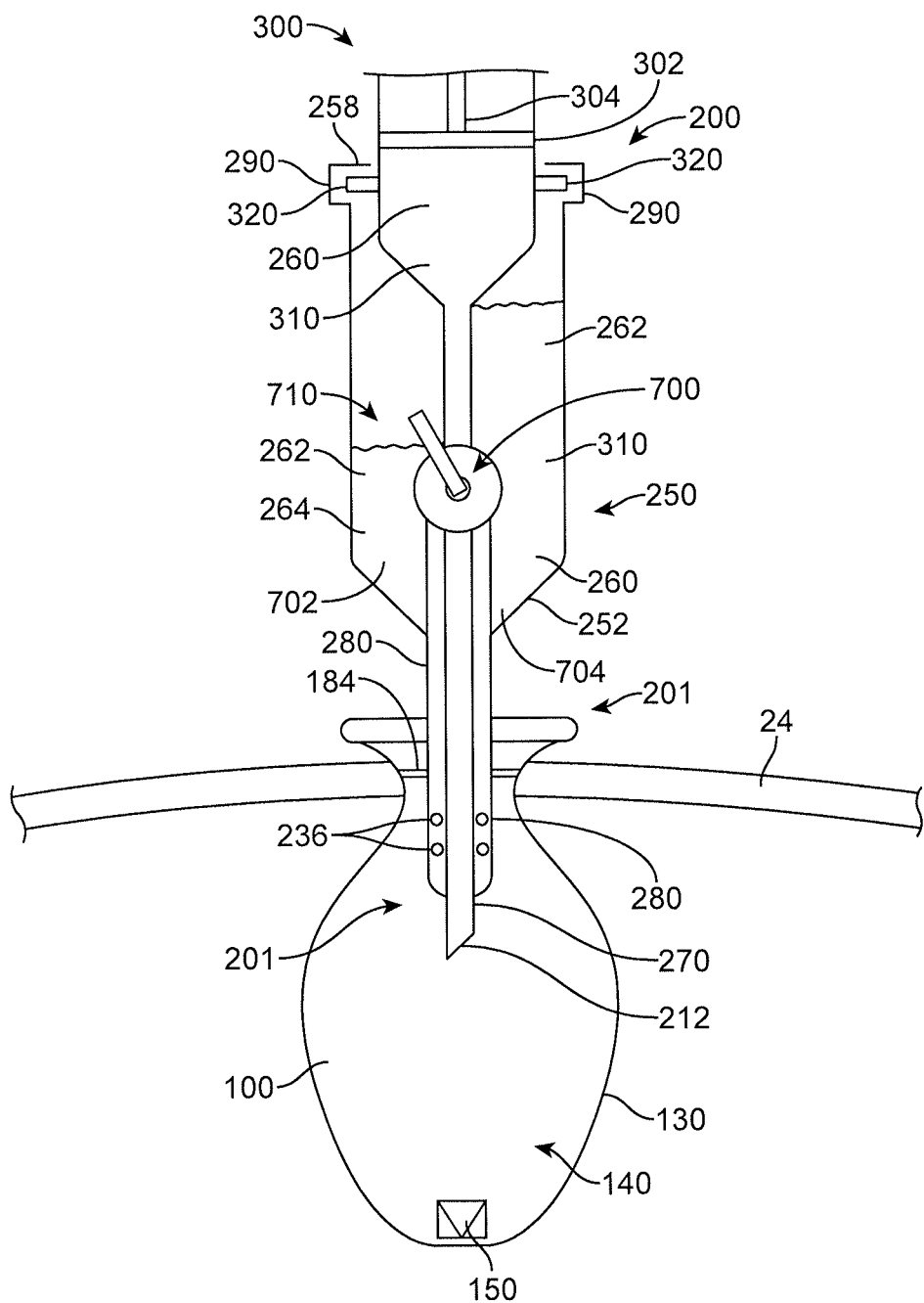
FIG. 30A shows an embodiment of an exchange apparatus comprising a valve to direct flow toward a second receiver container when a sample of the implantable device fluid has been placed in a first receiver container.

FIG. 30A shows an embodiment of an exchange apparatus 200 comprising a valve 700 to direct flow toward a second receiver container 704 when a sample 264 of the implantable device fluid 262 has been placed in a first receiver container 702. The valve 700 can inhibit mixing of the implantable device fluid 262 with the therapeutic fluid 260, such that sample fluid 264 may comprise no substantially amount of therapeutic fluid 260. The sample fluid 264 can be removed used for one or more assays as described herein. The valve 700 may comprise one or more of a porous structure, a float valve, an annular float valve, a ball float valve, a flap valve, a flap valve with a float, a duckbill valve, or a stopcock. The valve 700 may comprise a manual valve, or may comprise one or more structures to automatically close or open when a sufficient amount of fluid has been placed in the first receiver container. The receiver container 250 may comprise the first receiver container 702 and the second receiver container 704. The exchange apparatus 200 may comprise one or more of the elongate structure 201, needle 270, sheath 280, receiver container 250, at least one opening 258, connector 290, syringe 300, piston 302, plunger 304, chamber 310, or connector 320 as described herein, for example.

The valve 700 may be configured in many ways to provide sample 264 of implantable device fluid 262. With elongate structure 301 introduced into therapeutic device 100, an initial amount of implantable device fluid 262 can be placed in first receiver container 702 with valve 700 comprising a first configuration. The first configuration of valve 700 can fluidically couple one or more openings 236 of elongate structure 201 with the first receiver container 702 and inhibit fluidic coupling of the one or more openings of elongate structure 201 with second receiver container 702. When a sufficient amount of implantable device fluid 262 has been placed in the first receiver container 702, the configuration valve 700 can change from the first configuration to the second configuration. The second configuration of valve 700 can fluidically couple the one or more openings 236 with the second receiver container 704 and inhibit flow to the first receiver container 702, such that a majority of the therapeutic fluid 260 mixed with implantable device fluid 262 is placed in second receiver container 704.

The valve 700 may comprise a manual valve 710 operable by a user, and may comprise one or more of many valves known to a person of ordinary skill in the art, for example a stopcock or other manual or automatic valve, for example.

The sample 264 within first container 702 can be removed for analysis with one or more of many methods or structures as described herein.

Figure 30B:
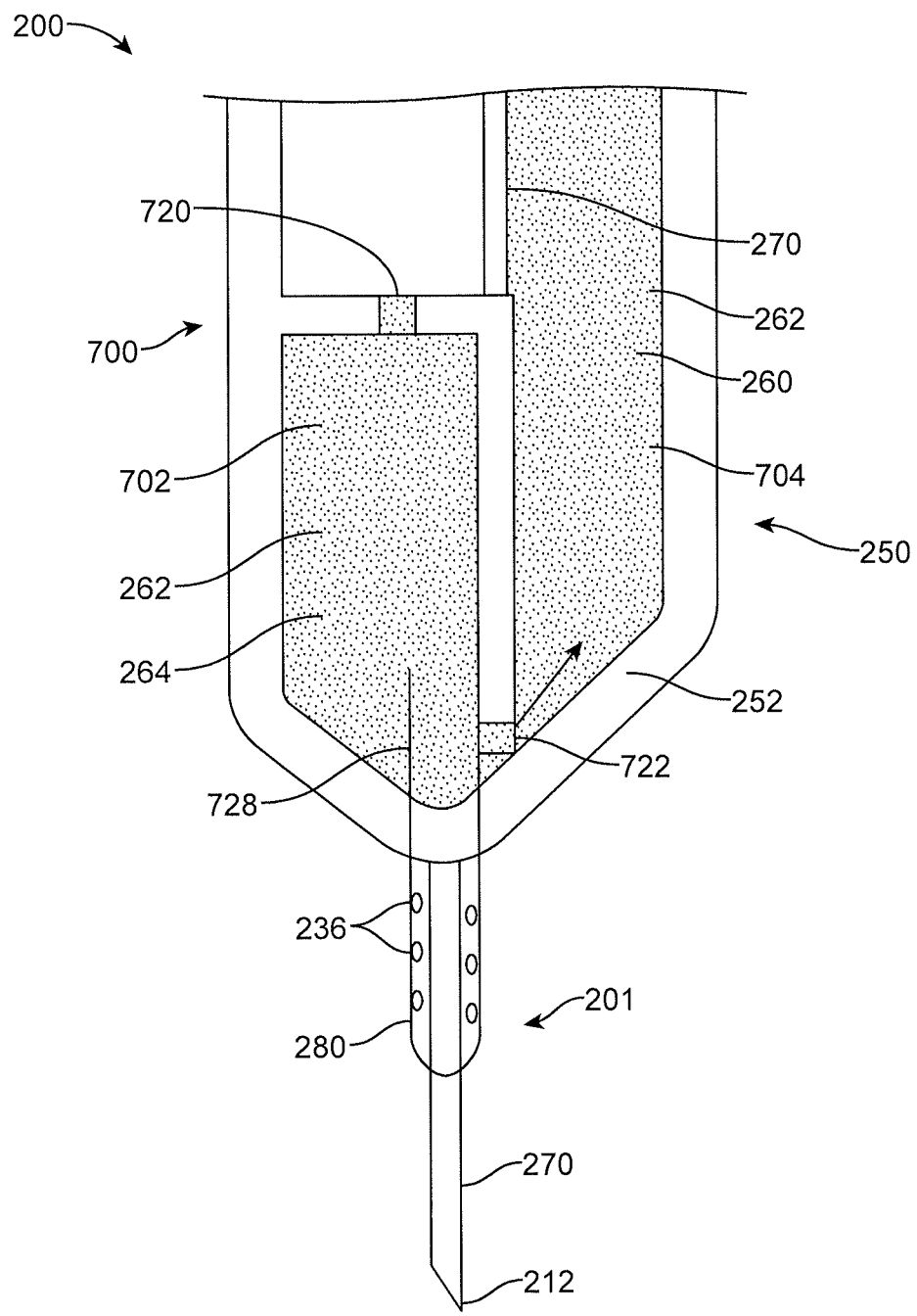
FIG. 30B shows an embodiment of an exchange apparatus having a valve comprising a porous structure to direct flow toward a second receiver container when a sample of the implantable device fluid has been placed in a first receiver container.

FIG. 30B shows an embodiment of an exchange apparatus 200 having a valve 700 comprising a porous structure 720 to direct flow toward a second receiver container 704 when sample 264 of the implantable device fluid 262 has been placed in first receiver container 702. The valve 720 may comprise a substantially dry porous structure in an initial open configuration and a gas such as air can be situated within first receiver container 702. Implantable device fluid 262 accumulates in the first receiver container 702 and rises inside the first container 702 from a distal end near the elongate structure to a proximal end of the first container. When a sufficient amount of implantable device fluid 262 is placed on first container 702, the valve 720 contacts the implantable device fluid 262 comprising liquid and the resistance to flow of the valve 720 increases substantially. The wetted valve 720 comprises a substantially closed configuration such that the implantable device fluid 262 passes through a flow resistance structure 722. The flow resistance structure 722 comprises a resistance to flow when wet that is greater than the resistance to flow of valve 720 in the dry configuration and substantially less than the resistance to flow of valve 720 in the wet configuration, such that the dry valve 720 corresponds to a substantially open configuration and the wet valve 720 corresponds to a substantially closed configuration. The valve 720 and the flow resistance structure 722 may each comprise a porous structure similar to the porous structure for sustained release of the therapeutic agent as described herein, for example.

The valve 720 and flow resistance structure 722 can be configured in many ways to provide sample 264 of implantable device fluid 262 with no substantial portion of therapeutic fluid 260. The relative resistance to flow of the porous structure 720 when we can be substantially greater than the resistance to flow of the resistance structure 722 when wet, for example at least about twice, and in many embodiments at least about five times the resistance to flow of the flow resistance structure. The flow resistance structure 722 may comprise a valve that opens under pressure such as a duckbill valve or flap with a spring, for example. A baffle 728, a channel, or other internal structure can be provided to inhibit mixing of the therapeutic fluid 260 and implantable device fluid 262 with the sample fluid 264 when valve 720 is wet and comprises the closed configuration.

Figure 30C:
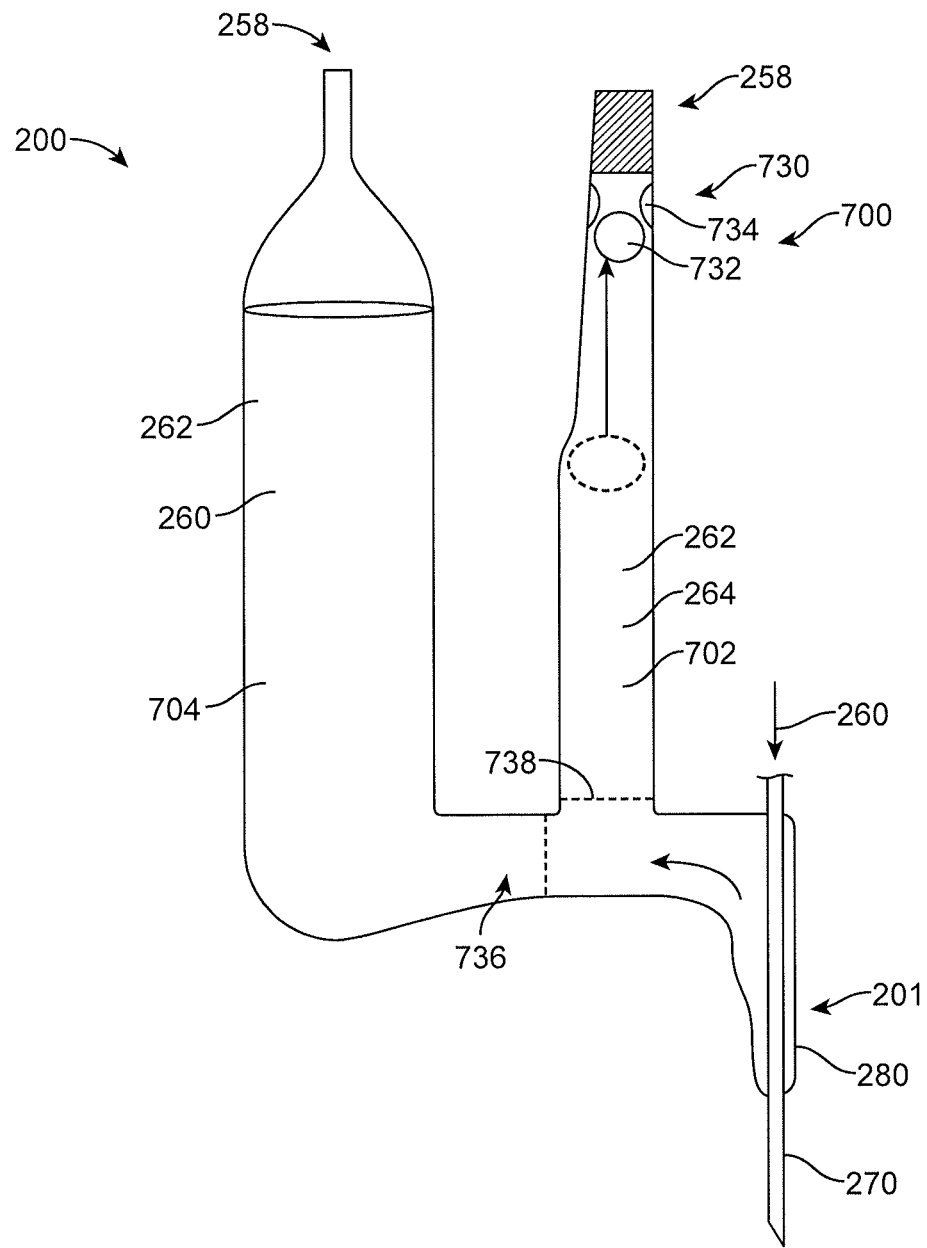
FIG. 30C shows an embodiment of an exchange apparatus having a float valve comprising a ball to direct flow toward a second receiver container when a sample of the implantable device fluid has been placed in a first receiver container.

FIG. 30C shows an embodiment of an exchange apparatus 200 in which valve 700 comprises a float valve 730. The float valve 730 comprises a float ball 732 to direct flow toward a second receiver container 704 when a sample 264 of the implantable device fluid 262 has been placed in a first receiver container 702. The valve 732 can slide along first container 702. A valve 736 such as a flap valve or duckbill valve, for example, can be provided to provide a resistance to flow and drive fluid into the first receiver container 702. When the implantable device fluid 262 advances into container 702, float ball 732 rises in the first container 702 until the float ball contacts a seat 734 and inhibits flow into the first container. When float ball 732 contacts seat 734 additional flow into first container 702 is inhibited and valve 736 opens to allow implantable device fluid 262 into the second receiver container 704. The received implantable device fluid 262 mixed with therapeutic fluid 260 may displace a gas such as air through opening 258. A flow resistance structure 738 such as a second duck bill valve or baffle can be provided near the opening to the first container to inhibit mixing of sample 264 of the first receiver container 702, for example.

Figure 30D:
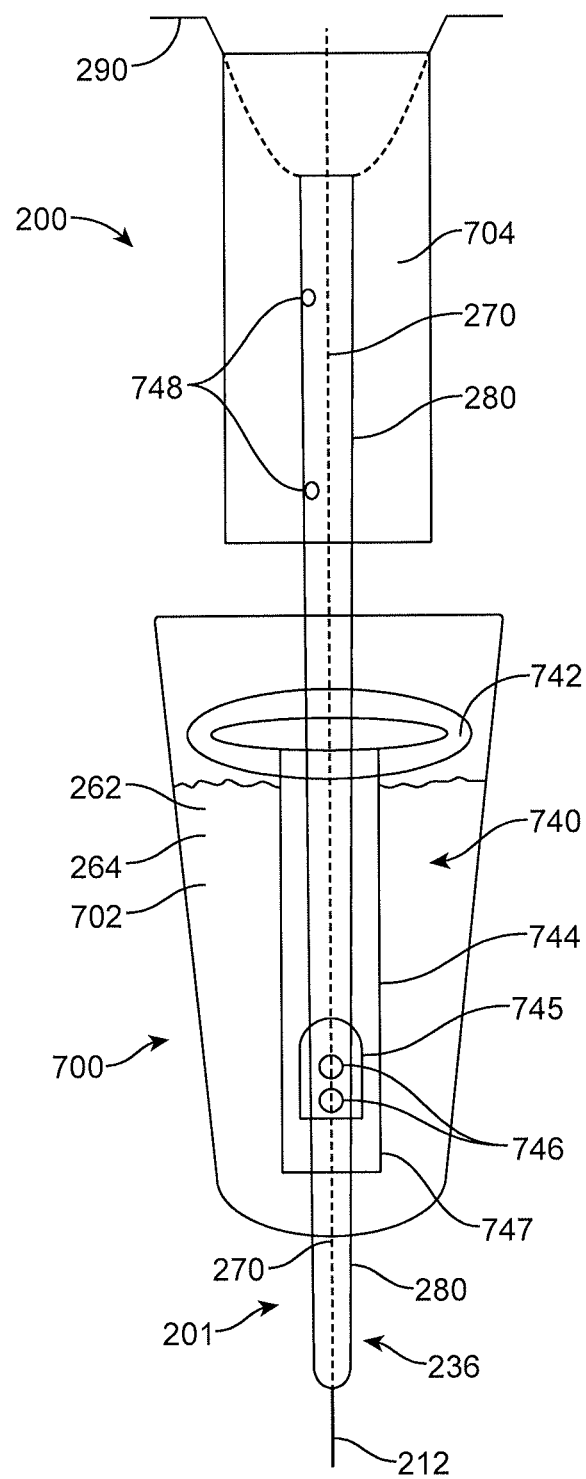
FIG. 30D shows an embodiment of an exchange apparatus having a float valve comprising a sliding annular structure to direct flow toward a second receiver container when a sample of the implantable device fluid has been placed in a first receiver container.

FIG. 30D shows an embodiment of an exchange apparatus 200 having a valve 700 comprising a float valve 740. The float valve 740 comprises a sliding annular structure 744 to direct flow toward a second receiver container 704 when a sample 264 of the implantable device fluid 262 has been placed in first receiver container 702. The sliding annular structure 744 may comprise an annular float ring 742 coupled to a tube having an opening 745 to pass fluid when the valve 740 is open. The sheath 280 can extend over needle 270 upward from the first receiver container 702 to the second receiver container 704. The sheath 280 may comprise one or more openings 236 to pass the implantable device fluid 262 into the first receiver container 702 through opening 745. As the first receiver container 702 receives implantable device fluid 262, valve 740 rises and slides axially along sheath 280 such that a portion 747 of annular structure 744 slides over one or more openings 236 to inhibit flow to the first receiver container 702.

In the closed configuration, valve 740 directs flow of the implantable device fluid 262 and therapeutic fluid 260 into second receiver container 704 through holes 748 in sheath 280. The exchange apparatus may comprise connector 290 to couple to a syringe as described herein.

Figure 30E:
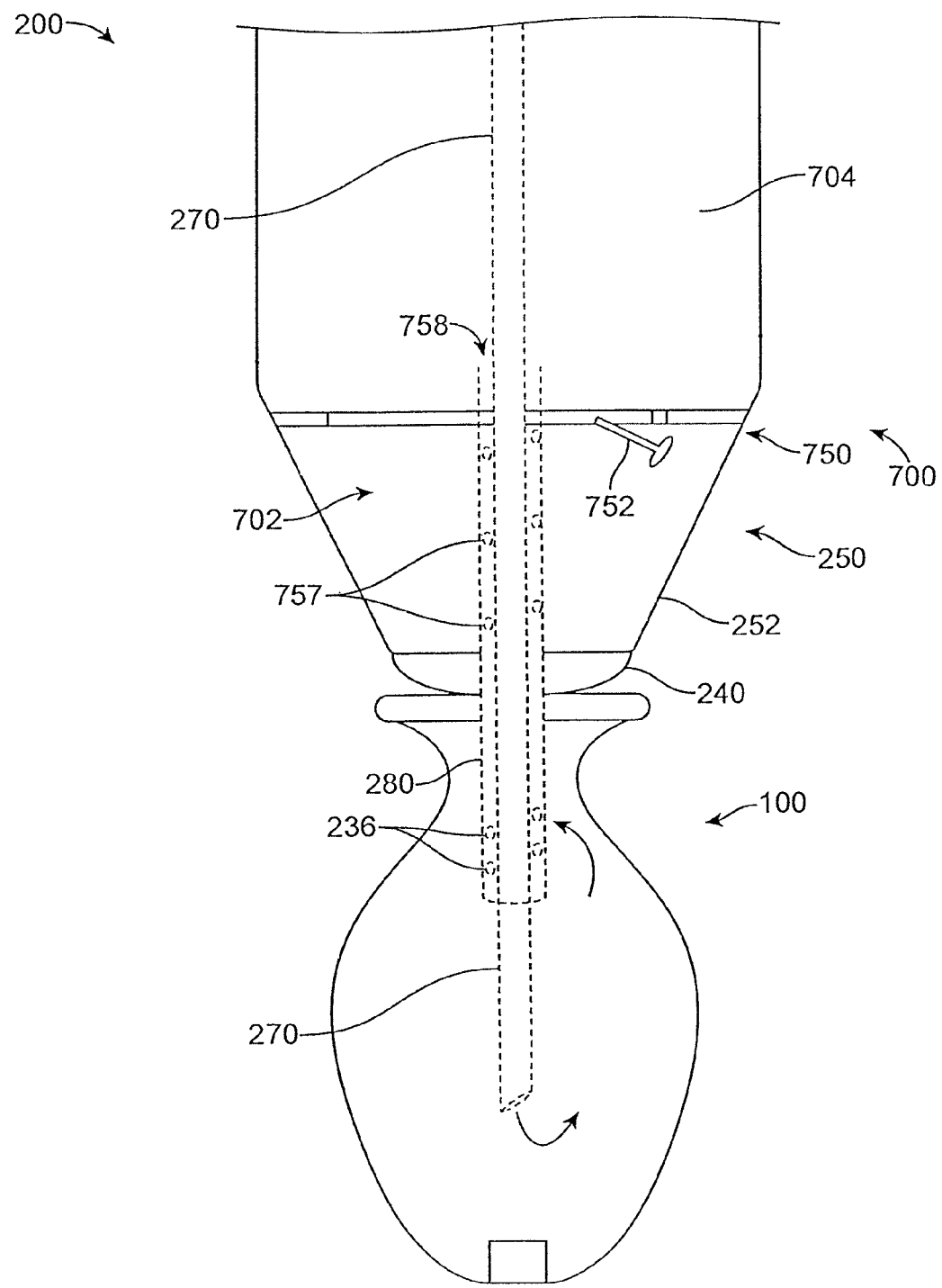
FIG. 30E shows an embodiment of an exchange apparatus having a float valve comprising a flap to direct flow toward a second receiver container when a sample of the implantable device fluid has been placed in a first receiver container.

FIG. 30E shows an embodiment of an exchange apparatus 200 in which valve 700 comprises a float valve 750 to direct flow toward a second receiver container when a sample of the implantable device fluid has been placed in a first receiver container. Float valve 750 comprises a flap 752. The flap 750 allows sample fluid to enter the first receiver container 702 through openings 757 of sheath 280, and when a sufficient amount of sample fluid has been received with sample container 702, float valve 750 closes to inhibit flow through openings 757. The implantable device fluid 262 is passed through opening 758 into second receiver container 704 when the float valve 750 is closed.

FIG. 31A1 shows an embodiment of an exchange apparatus 200 having a receiver container 250 comprising a fluid separator 800 comprising an internal channel 822 sized to support the implantable device fluid 262 with a pocket of air. The fluid separator 800 may comprise a tubular structure 820, for example a column, having an internal dimension such as a diameter sized to support the implantable device fluid with an immiscible separator fluid. The immiscible separator fluid may comprise one or more of an oil, a hydrophobic liquid, a gas, or air, for example. The exchange apparatus may comprise one or more of many structures as described herein such as connectors to couple to a syringe and an elongate structure comprising a sheath and needle. The internal channel 822 of fluid separator 800 can be fluidly coupled to openings 236 to receive implantable device fluid 262 as described herein. The fluid received from the implantable device can be received in receiver container so as to separate the implantable device fluid 262 from the therapeutic fluid 260. The internal channel 822 may initially comprise a gas such as air which can be displaced through opening 258 of receiver container 250.

While the exchange apparatus can be used in many ways with an immiscible separator fluid such as a gas comprising air, in many embodiments the therapeutic fluid 260 is first drawn into a syringe 300, and then the immiscible separator fluid such as air drawn into syringe 300. The syringe 300 can be coupled to the exchange apparatus 200 with the therapeutic fluid supported with the immiscible separator fluid such as air within the container, for example. In many embodiments, the barrel of the syringe comprises an inner diameter sized such that the therapeutic fluid 260 can remain free standing within the barrel of the syringe and may be supported with air, such that the air can be injected into the implantable device before the air is injected. The implantable device may comprise a maximum cross-sectional dimension, for example a maximum diameter, such the implantable device fluid can be supported and displaced with the immiscible separator fluid 810 placed in the lower portion of the reservoir chamber near porous structure 150. Injection of the immiscible separator fluid 810 displaces implantable device fluid 262 through one or more openings 236 of sheath 280 and upward into channel 822. When a substantial portion of the implantable device fluid has been displaced from the reservoir chamber, for example with air, the therapeutic fluid 260 can enter the reservoir chamber such that the implantable device fluid 262 remains substantially separated from the therapeutic fluid 260 introduced into the reservoir chamber.

The separator fluid 810 may comprise a miscible separator fluid, for example saline or other liquid capable of mixing with the therapeutic fluid 260 and the implantable device fluid 262, and the separator fluid 810 may comprise a sufficient volume so as to inhibit mixing of the therapeutic fluid 260 with the implantable device fluid 262. In many embodiments, the separator fluid 810 comprises a fluid not miscible with the therapeutic fluid 260 and implantable device fluid 262, each of which may comprise substantial amounts of water. The immiscible separator fluid 810 can inhibit mixing of the implantable device fluid 262 and the therapeutic fluid 260 with the separator fluid 810, such that the separator fluid 810 may comprise a barrier and inhibit mixing of the components of the implantable device fluid 262 with components of the therapeutic fluid 260.

FIG. 31A2 shows an embodiment of the exchange apparatus 200 of FIG. 31A1 having the implantable device fluid 262 supported with a pocket of immiscible separator fluid 810 such as air 812, so as to separate the implantable device fluid 262 from the therapeutic fluid 260. An interface 818 extends between the immiscible separator fluid 810 and the implantable device fluid 262. An interface 814 extends between the immiscible separator fluid 810 and the therapeutic fluid 260. In many embodiments, immiscible separator fluid 810 comprises a gas, and implantable device fluid 262 and therapeutic fluid 260 each comprise liquid such that interface 814 comprises a meniscus and interface 818 comprise a meniscus.

FIG. 31B1 shows an embodiment of an exchange apparatus 200 having a fluid separator 800 comprising an internal channel having a first portion 852 sized to support the implantable device fluid with a pocket of an immiscible separator fluid air and a second portion 854 sized to pass an immiscible separator fluid such as air through the implantable device fluid. The first portion may comprise a volume approximating the volume of the reservoir chamber, for example. The exchange apparatus may comprise one or more of the structures of the exchange apparatus 200 as described herein, for example receiver container 200 and container wall 252 may have dimensions so as to define the first portion 852 and the second portion 854.

FIG. 31B2 shows an embodiment of the exchange apparatus of FIG. 31B1 having the first portion 852 supporting the implantable device fluid 262 with the immiscible separator fluid 810 such as air 812. The tip 212 of needle 270 may extend to the distal end of the reservoir chamber 140 such that the bubble forms at the distal end of the reservoir to increase exchange efficiency, for example. The reservoir chamber 140 and the first portion 852 may comprise immiscible separator fluid 810 such as air 812.

FIG. 31B3 shows an embodiment of the exchange apparatus of FIGS. 31B1 and 31B2 having the first portion 852 supporting the implantable device fluid 262 with the pocket of immiscible separator fluid 810 and therapeutic fluid 260, and the second portion containing the implantable device fluid. As additional gas such as air moves upward from the first portion 852 to the second portion 854, the immiscible separator fluid comprising a gas such as air forms bubbles in second portion 854 having the increased inner dimensions and the bubble can travel upward to escape through opening 258. The first portion 852 and the second portion 854 may each comprise an annular channel having an inner dimension determined by the outside diameter of needle 270, for example. The increased outer dimension of the annular channel of the second portion 854 allows bubbles to form in the implantable device fluid 262 contained in the second portion such that the bubbles can rise and escape through valve 258.

Figure 31C:
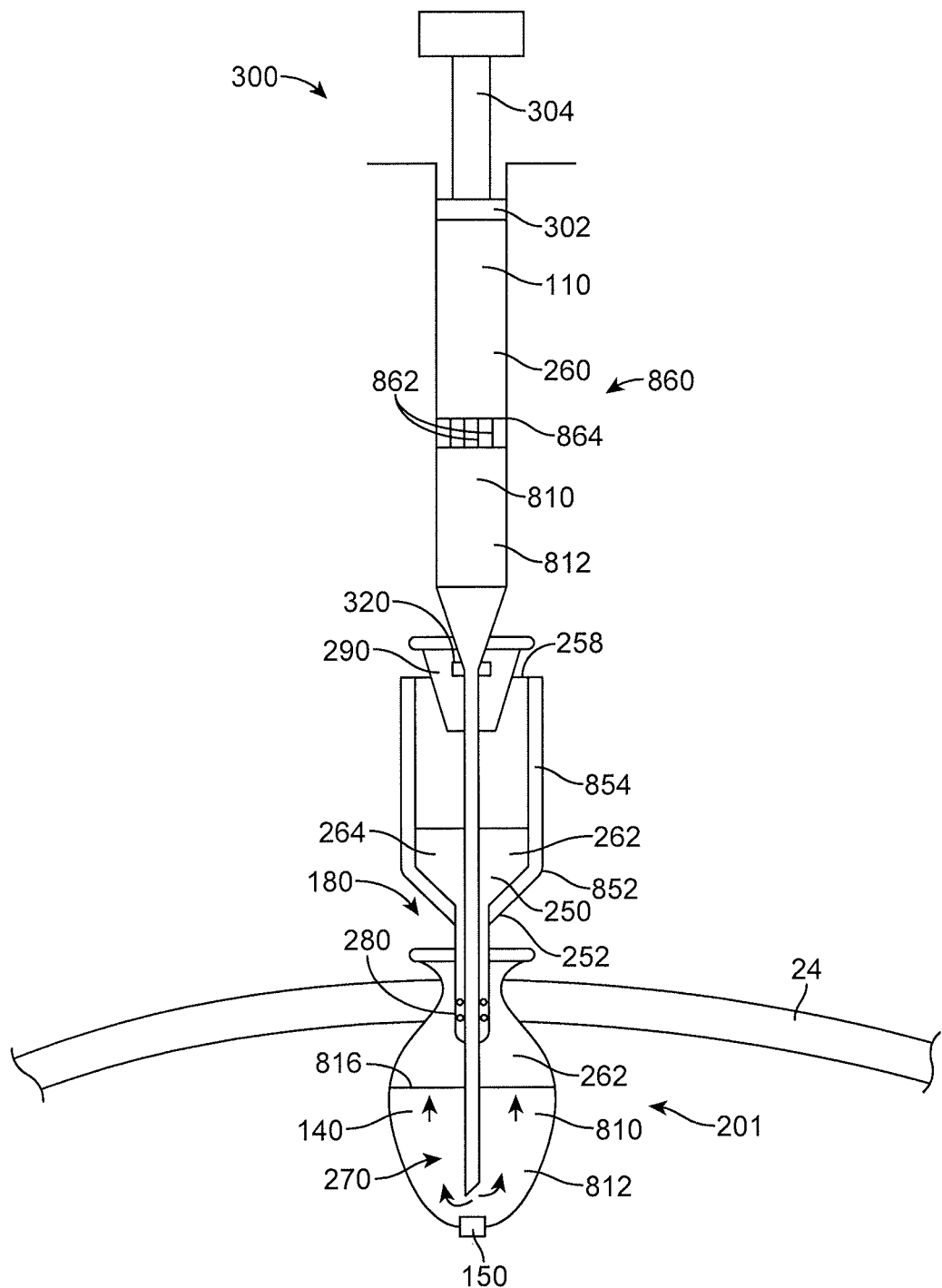
FIG. 31C shows an embodiment of an exchange apparatus coupled to a syringe to inject a displacement fluid comprising air into a therapeutic device to collect a sample of implantable device fluid.

FIG. 31C shows an embodiment of exchange apparatus 200 coupled to a syringe 300 comprising a separator structure 860 to inject a separation fluid 810 and a therapeutic fluid into therapeutic device to collect a sample 264 of implantable device fluid 262. The separator structure 860 may comprise one or more of a piston 864, a plunger, a disk or a plug having one or more holes 862. The holes 862 may comprise a sufficient resistance to flow such that the piston 864 moves downward toward the elongate structure 201 when the piston 302 is advanced.

The piston 864 can displace the immiscible separator fluid 810 comprising air, such that the immiscible separator fluid 810 is displaced into reservoir chamber 140 and forms an interfacial boundary 816. The interfacial boundary 816 moves toward sheath 280 as the implantable device fluid is displaced with the immiscible separator fluid 810. When the piston 864 has advanced a sufficient distance, movement of piston 864 along the cylinder barrel is inhibited, and the therapeutic fluid 260 is displaced through the one or more holes 862 with piston 302. The displaced therapeutic fluid 260 is placed in reservoir chamber 140, for example with injection through the needle. The immiscible separator fluid 810 is displaced with therapeutic fluid 260 such that the immiscible separator fluid 810 enters receiver container 250.

In many embodiments the receiver container 250 comprises a volume that is at least the volume of the injected material comprising therapeutic fluid 260 and immiscible separator fluid 810, such that the volume of the receiver container 250 is sufficient to retain the implantable device fluid 262 and the immiscible separator fluid 810. The volume of immiscible separator fluid 810 injected with the therapeutic fluid can be less than, approximately the same as, or greater than the volume of the therapeutic agent injected. In many embodiments, the immiscible separator fluid 810 comprises a volume sufficient to separate the therapeutic fluid from the implantable device fluid and which is substantially less than the volume of the reservoir chamber. For example, the amount of immiscible separator fluid 810 may comprise a volume that is sufficient to form a bubble within the reservoir chamber 140 and that is substantially less than the volume of the volume of reservoir chamber 140.

The receiver container 250 can be configured in many ways to receive the implantable device fluid 262 and the immiscible separator fluid 810. For example, the receiver container 250 may comprise the inside dimension sufficient to support the implantable device fluid with the immiscible separator fluid along a majority of the length of the receiver container 250. Alternatively, the first portion 852 of the receiver container may comprise the inside dimension sufficient to support the implantable device fluid 262 and the second portion 854 of the receiver container may comprise the inside dimension sufficiently large so as to pass the immiscible separator fluid 810 through the implantable device fluid. A person or ordinary skill in the art can determine the internal dimensions of the first portion and the second portion based on the teachings of the present disclosure.

Figure 32:
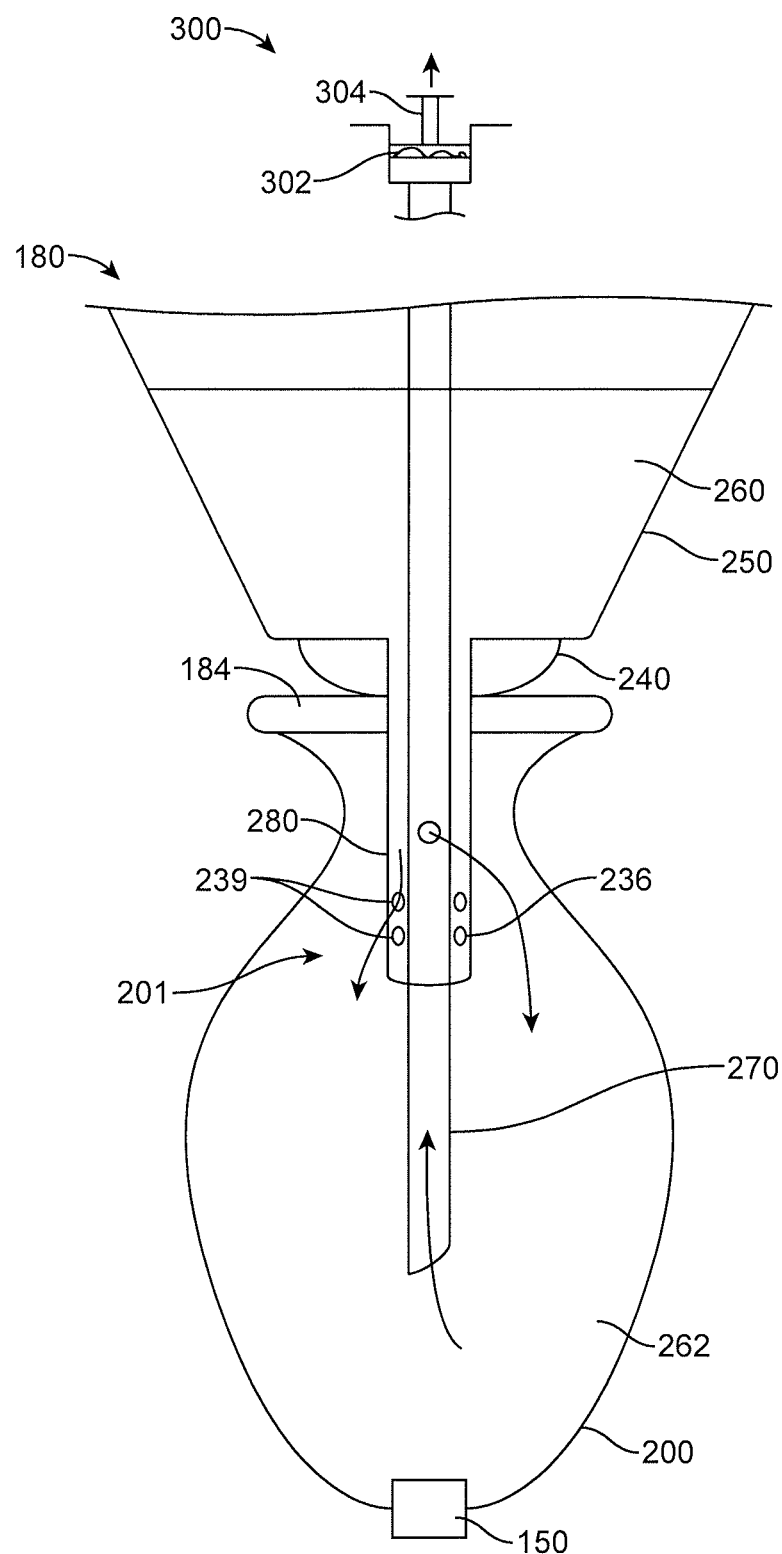
FIG. 32 shows an embodiment of an exchange apparatus coupled to a syringe to draw therapeutic fluid into the implantable device with aspiration of the implantable device fluid into the syringe.

FIG. 32 shows an embodiment of an exchange apparatus coupled to syringe 300 to draw therapeutic fluid into the implantable device from the container 250. The implantable device fluid 262 can be drawn from the reservoir chamber in one or more of many ways, for example with syringe so to provide aspirating suction of the implantable device fluid from the implantable device into the syringe. As the needle 272 extends through penetrable barrier 184 so as to provide a seal and the porous structure 150 comprises a resistance to flow of components of the eye, the movement of the implantable device fluid 262 into the chamber of syringe 300 results in therapeutic fluid 260 moving from chamber 250 through the one or more openings 289 in sheath 280. Air at approximately atmospheric pressure can move into container 250 to urge and displace the therapeutic fluid 260 into the reservoir chamber when the implantable device fluid 262 is drawn with the syringe.

Figure 33:
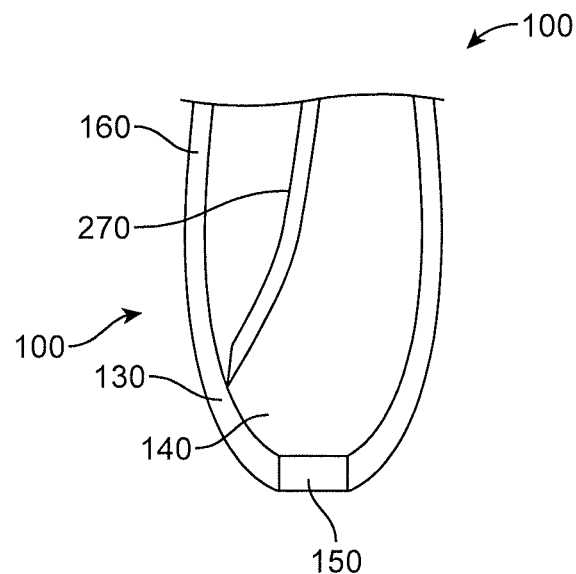
FIG. 33 shows an embodiment of a curved needle of an exchange apparatus to direct therapeutic fluid toward a wall of a container.

FIG. 33 shows an embodiment of a curved needle 270 of an exchange apparatus to direct therapeutic fluid 260 toward a wall 260 of a container 230 of the reservoir chamber 240. The curved needle can be placed near the porous structure 150 and may result in a reproducible flow pattern of the therapeutic fluid 260 placed in the container. The reproducible flow pattern provided by the curved needle 270 can provide a consistent flow pattern over porous structure 150 and may provide a more uniform amount of bolus through porous structure 150.

Figure 34:
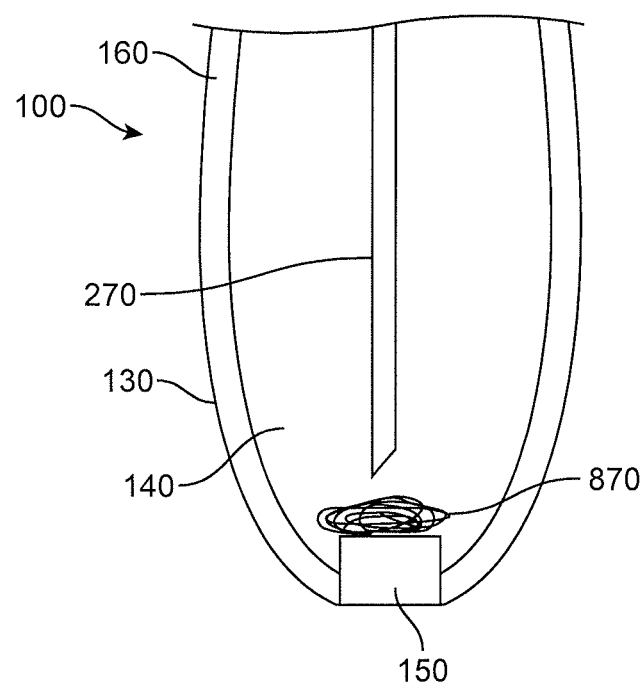
FIG. 34 shows an embodiment of a covering on a porous structure of a therapeutic device to inhibit bolus release when the therapeutic fluid is introduced and a needle of an exchange apparatus oriented toward the covering.

FIG. 34 shows an embodiment of a covering 870 on a porous structure of a therapeutic device to inhibit bolus release when the therapeutic fluid is introduced. The covering 870 can inhibit bolus release when the needle is oriented toward the porous structure 150 and the covering 870, for example.

Figure 35:
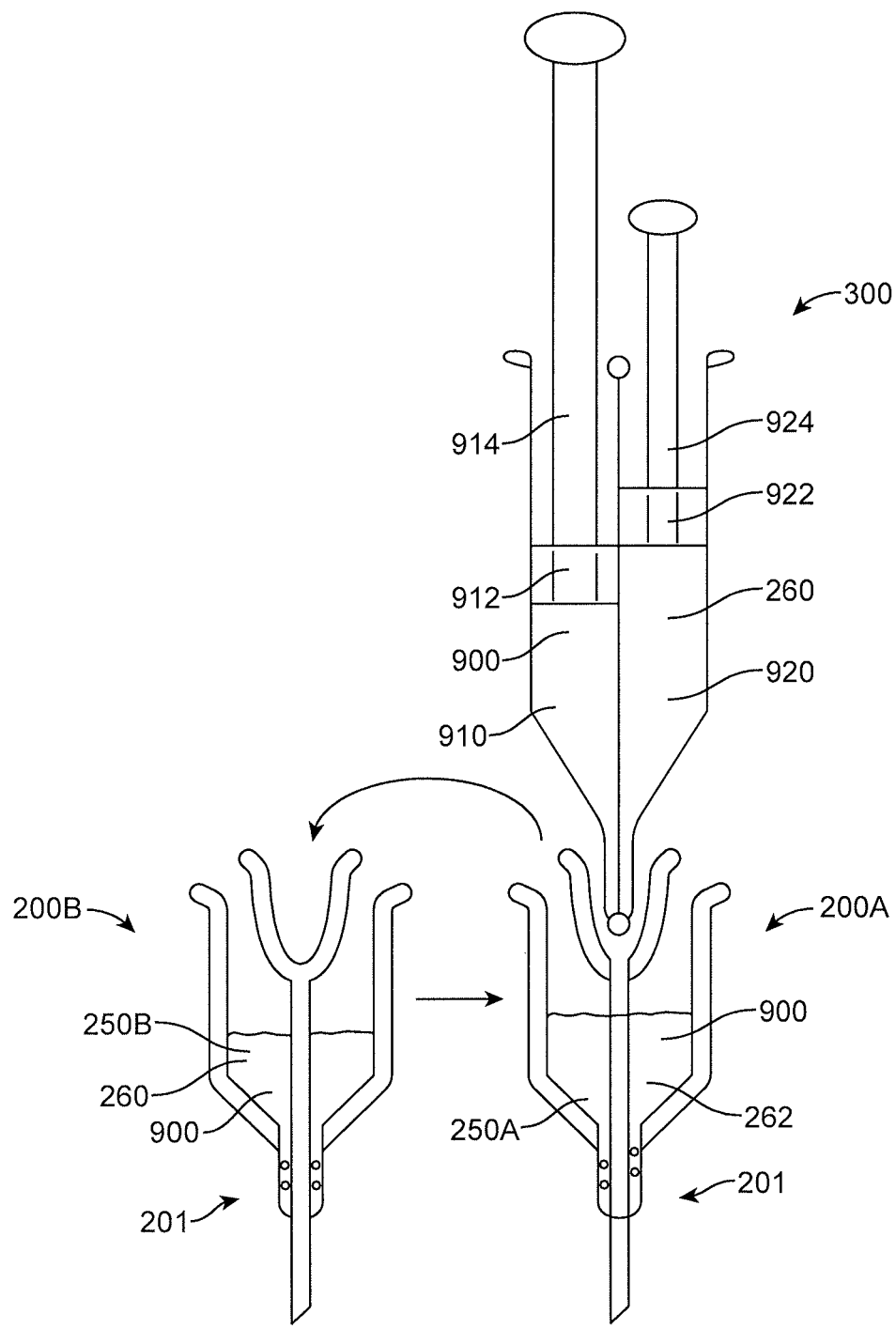
FIG. 35 shows an embodiment of a first exchange apparatus coupled to a double barrel syringe to exchange a first exchange fluid with the implantable device fluid, and a second exchange apparatus to exchange the first exchange fluid placed in the therapeutic device with a therapeutic fluid.

FIG. 35 shows an embodiment of a first exchange apparatus 200A coupled to a double barrel syringe 300 to exchange a first exchange fluid 900 with the implantable device fluid 262, and a second exchange apparatus 200B to exchange the first exchange fluid placed in the therapeutic device with therapeutic fluid 260. The first exchange fluid 900 may comprise the separator fluid 810 as described herein. The first exchange fluid 900 may comprise water, for example phosphate buffered saline (hereinafter "PBS"). Alternatively, the first exchange fluid may comprise an immiscible separator fluid as described herein.

The first exchange apparatus 200A and the second exchange apparatus 200B may each comprise many of the structures of exchange apparatus 200 as described herein. For example, the first exchange apparatus 200A and the second exchange apparatus 200B may each comprise the elongate structure 201 and receiver container 250 as described herein. The double barrel syringe 300 may comprise the therapeutic fluid and the first exchange fluid 900. The double barrel syringe 300 may comprise a first chamber 910 containing the first exchange fluid 900 and a second chamber 920 containing the therapeutic fluid 260. The first chamber 910 may be coupled to a first piston 912 and plunger 914 having a first length. The second chamber 920 may be coupled to a second piston 922 and plunger 924 having a second length. The first length can be longer than the second length to that the contents of the first chamber are injected before the second chamber. The first exchange apparatus 200A can be connected to the syringe 300 and the elongate structure 201 inserted into the implantable device as described herein, and the first plunger advanced so as to displaced the implantable device fluid 262 from the reservoir chamber 140 with the first exchange fluid 900. The first exchange apparatus 200A can be removed from therapeutic device implanted in the eye. The first exchange apparatus 200A can be disconnected from the syringe 300, and the second exchange apparatus 200B connected to the syringe 300 and advanced into the therapeutic device 100. The second plunger 924 can be advanced to displace the first exchange fluid 900 from the reservoir chamber 140 of the implantable device with the therapeutic fluid 260 as described herein.

In many embodiments, one or more of the components of the first exchange apparatus 200A and the second exchange apparatus 200B can be combined for use with the double barrel syringe so that the first exchange fluid and the therapeutic fluid can each be exchanged sequentially when the exchange apparatus 200 is placed in the implantable device and without removing the exchange apparatus from the implanted device. For example, the exchange apparatus 200 may comprise the first receiver 702 container to receive the implantable device fluid and the second receiver container 704 as described herein to receive the first exchange fluid, and the first receiver container and the second receiver container can be coupled to one or more valves as described herein such that the implantable device fluid 262 is directed to the first receiver container when the valve comprises a first configuration and the first exchange fluid is directed to the second receiver container when the valve comprises a second configuration as described herein.

Experimental

Figure 36:
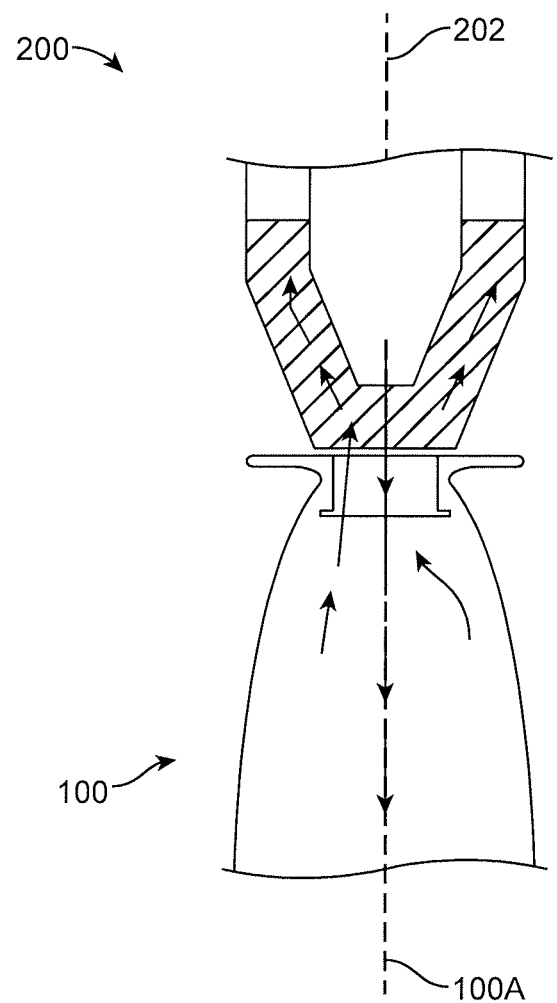
FIG. 36 shows an embodiment of an experimental test apparatus.

FIG. 36 shows an experimental test apparatus. The test apparatus comprised an injector coupled to a bi-needle exchange apparatus 200 to inject a therapeutic fluid comprising a therapeutic agent into a test implantable device 100. The therapeutic fluid comprised a 100 mg/mL formulation of ranibizumab prepared in accordance with U.S. Pat. Pub. No. 2010/0015157, entitled "Antibody Formulations", the full disclosure of which is incorporated by reference. The injected formulation comprised a density at least about 1% greater than the fluid of the implantable device, which comprised saline.

The therapeutic fluid was injected through the penetrable barrier comprising a septum of silicone elastomer. The injector needle was approximately 33 gauge and coupled to a syringe and positioned below the receiver needle. The receiver needle received liquid from the implantable device and extended upward to a receiver container. Axis of the injector needle 202 and the axis of the implantable device 100A were oriented to obtain samples. The reservoir chamber of the implantable device comprised about 25 μL, and about 50 μL were injected. The orientation of the axes varied from 0 degrees (horizontal) 45 degrees away from horizontal. At the −45 degree orientation the penetrable barrier was located above the reservoir chamber and the opening to the receiver needle located above the opening to the injector needle.

Figure 37:
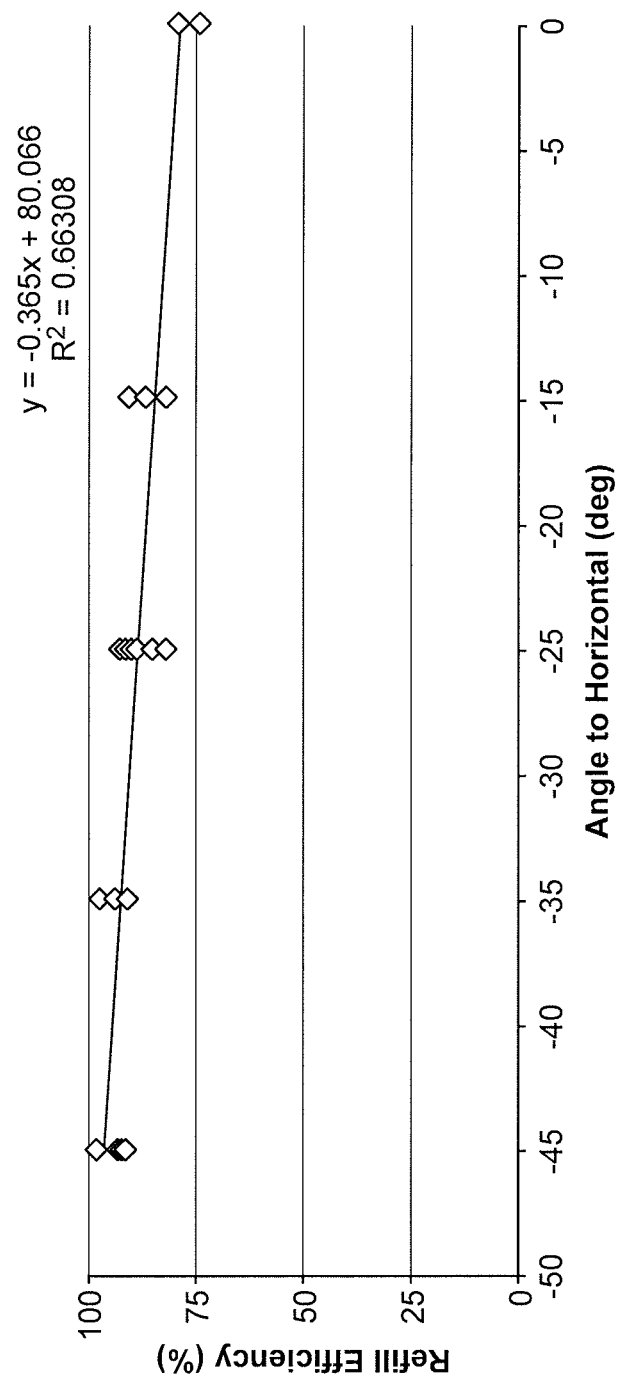
FIG. 37 shows experimental results obtained with the test apparatus of FIG. 36.

FIG. 37 shows experimental results obtained with the test apparatus of FIG. 36. The refill efficiency corresponded to the amount of therapeutic fluid placed in the reservoir chamber of the implantable device when the 50 uL had been injected. For 0 degrees, the efficiency was about 80%. The efficiency increased with the angle to about 95% at −45 degrees.

Table 2 shows device angles and fill efficiencies corresponding to the values in the graph of FIG. 37.

| Device Angle (+/− sign arbitrary) | Refill Efficiency |
|---|---|
| 0 | 77.5 |
| 15 | 88.3 |
| 25 | 88.9 |
| 35 | 94 |
| 45 | 94 |

A concentric needle device was also tested and provided similar results.

Pressure studies have been conducted with the injector apparatus having the plurality of openings. The sheath comprised polyimide placed over a 33 Gauge needle. A first pressure gauge was coupled to a syringe on the input side of the needle, and a second pressure gauge was coupled to the implantable device reservoir chamber where the porous structure is shown above. The input pressure to the syringe of 12 N produced a pressure of 85 pounds per square inch (hereinafter "psi") into the needle and implantable device chamber had a pressure of about 45 psi. This amount of input pressure corresponds to a clinically acceptable exchange time of about 5 seconds, for example.

Additional experiments can be conducted by a person of ordinary skill in the art based on the teachings described herein, for example experiments with an exchange apparatus comprising a polyimide sheath comprising a plurality of openings over a needle as described herein.

Additional experiments can be conducted with one or more of many release control mechanisms to determine the resistance to flow of the release control mechanism suitable for use in accordance with embodiments described herein. For example, studies can be conducted with porous structures of varying dimensions, release rates, and manufacturing processes, in order to measure the flow through the frits with pressure so as to determine the resistance to flow.

While the exemplary embodiments have been described in some detail, by way of example and for clarity of understanding, those of skill in the art will recognize that a variety of modifications, adaptations, and changes may be employed.

TABLE 1A

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous 81oronary intervention, unstable angina | 42632 |
| ABT-578 | (Abbott Laboratories) | Limus Immunophilin Binding Compounds | | |
| Acetonide Adalimumab | Humira ™ (Abbott Laboratories) | Antirheumatic Agents; Immunomodulatory Agents | Uveitis, AMD | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |

TABLE 1A-continued

Therapeutic Agent List

| Generic Name | Brands (Companies) | Category | Indication | Molecular Weight |
|---|---|---|---|---|
| Alteplase | Activase ™ (Genentech Inc) | Thrombolytic Agents | For management of acute myocardial infarction, acute ischemic strok and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate: C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet devired growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusio | 90569 |
| Arcitumomab | CEA-Scan ™ | Diagnostic Agents; Imaging Agents | For imaging colorectal tumors | 57561 |
| Asparaginase | Elspar ™ (Merck & co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |

TABLE 1A-continued

Therapeutic Agent List

| Generic Name | Brands (Companies) | Category | Indication | Molecular Weight |
| --- | --- | --- | --- | --- |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Antidystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™; Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |

TABLE 1A-continued

Therapeutic Agent List

| Generic Name | Brands (Companies) | Category | Indication | Molecular Weight |
|---|---|---|---|---|
| Daclizumab | Zenapax ™ (Hoffmann-La Roche Inc) | Immunomodulatory Agents; Immunosuppressive Agents | For prevention of renal transplant rejection; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); NeoRecormon ™ (Roche); Procrit ™ (Ortho Biotech); Recormon ™ (Roche) | Antianemic Agents | For treatment of anemia (from renal transplants or certain HIV treatment) | 55066 |
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Binding Compounds, mTOR | AMD | |
| Exenatide | Byetta ™; Byetta ™ (Amylin/Eli Lilly) | | Indicated as adjunctive therapy to improve glycemic control in patients with Type 2 diabetes mellitus who are taking metformin, a | 53060 |

TABLE 1A-continued

Therapeutic Agent List

| Generic Name | Brands (Companies) | Category | Indication | Molecular Weight |
|---|---|---|---|---|
| | | | sulfonylurea, or a combination of both, but have not achieved adequate glycemic control. | |
| FCFD4514S | Genentech/Roche | Complement Cascade Inhibitor (Factor D) | AMD, Geographic Atrophy | |
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 91 ocalizing agent, provided that local ischaemia is not essential. | 46800 |
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |

TABLE 1A-continued

Therapeutic Agent List

| Generic Name | Brands (Companies) | Category | Indication | Molecular Weight |
| --- | --- | --- | --- | --- |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 95cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |

TABLE 1A-continued

Therapeutic Agent List

| Generic Name | Brands (Companies) | Category | Indication | Molecular Weight |
|---|---|---|---|---|
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |

TABLE 1A-continued

Therapeutic Agent List

| Generic Name | Brands (Companies) | Category | Indication | Molecular Weight |
|---|---|---|---|---|
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteoporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | PI3k/mTOR Inhibition | AMD, DME | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); | Anabolic Agents; Hormone Replacement Agents | For treatment of dwarfism, acromegaly and prevention of HIV-induced weight loss | 71500 |

TABLE 1A-continued

Therapeutic Agent List

| Generic Name | Brands (Companies) | Category | Indication | Molecular Weight |
|---|---|---|---|---|
| Squalamine | Protropin ™ (Genentech Inc.); Saizen ™ (Serono SA); Serostim ™; Serostim ™ (Serono SA); Tev-Tropin ™ (GATE) | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residueal or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 105ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelixis/Sanofi-Aventis | PI3k/mTOR Inhibition | AMD, DME | |

What is claimed is:

1. A system for injecting a therapeutic agent into an ocular implant, the ocular implant being at least partially implanted in an eye, the system comprising:
   a connector configured to reversibly couple to a syringe;
   a needle fixedly coupled to the connector and having a wall defining an injection lumen configured for injecting a therapeutic agent into the ocular implant through an opening from the injection lumen, the therapeutic agent having a first fluid density;
   a sheath fixedly positioned over the needle, the sheath having a wall defining an outlet lumen between an inner diameter of the wall of the sheath and an outer diameter of the wall of the needle, the wall of the sheath having a wall thickness and at least one opening extending through the wall thickness into the outlet lumen, the outlet lumen providing a pathway through which pre-existing liquid in the ocular implant exits the ocular implant as therapeutic agent is injected into the ocular implant through the needle, the pre-existing liquid having a second fluid density; and
   a receiver chamber fixedly coupled to the sheath and fluidly coupled to the outlet lumen of the sheath, the receiver chamber configured to receive the pre-existing liquid that exits the ocular implant via the at least one opening extending through the wall thickness of the sheath,
   wherein the injection lumen is in a fixed position relative to the outlet lumen such that the opening from the injection lumen is positioned distal to a distal end of the sheath, and
   wherein injection of the therapeutic agent into the ocular implant upon application of positive pressure by the syringe via the injection lumen displaces, with at least partial separation from the injected therapeutic agent, the pre-existing liquid in the ocular implant into the receiver chamber via the at least one opening of the sheath.

2. A system as in claim 1, wherein a distal tip of the sheath tapers such that at least a portion of the distal tip of the sheath contacts an outer surface of the needle.

3. A system as in claim 2, wherein the distal tip of the sheath tapers at an angle of no more than about 20 degrees to a longitudinal axis of the sheath.

4. A system as in claim 1, wherein at least a portion of a distal tip of the sheath is spaced from an outer surface of the needle.

5. A system as in claim 1, wherein the receiver chamber is removable from the injection system.

6. A system as in claim 1, wherein the receiver chamber is removable from the injection system and contains a sample of the displaced pre-existing liquid from the ocular implant, and further comprising a sample container sized and shaped to receive the receiver chamber, the sample container being sized and shaped for placement into a centrifuge.

7. A system as in claim 1, wherein the wall includes a plurality of openings extending through the wall thickness, the plurality of openings positioned circumferentially about the sheath.

8. A system as in claim 1, further comprising a stop coupled to a distal end region of the receiver chamber such that the needle and the sheath extend through the stop, the stop having a surface configured to engage a tissue of the patient.

9. A system as in claim 8, wherein the at least one opening of the sheath is positioned distal to the receiver chamber and is separated distally from the stop by a distance from about 0.25 to about 2 mm.

10. A system as in claim 9, wherein the at least one opening of the sheath is a plurality of openings extending through the wall thickness that are located at a plurality of circumferential locations around a longitudinal axis of the sheath.

11. A system as in claim 9, wherein the at least one opening of the sheath is a plurality of openings extending through the wall thickness that are located at a plurality of axial locations along a longitudinal axis of the sheath.

12. A system as in claim 1, wherein the receiver chamber comprises a penetrable barrier configured to be penetrated by a needle in order to draw a sample from the receiver chamber.

13. A system as in claim 1, wherein the second fluid density is less than the first fluid density.

14. A system as in claim 1, wherein the therapeutic agent has a first fluid viscosity and the pre-existing liquid in the ocular implant has a second fluid viscosity that is less than the first fluid viscosity.

15. A system as in claim 1, wherein the connector comprises a Luer connector, a pressure fit connector, a non-standard connector, or a lock and key mechanism.

16. A system as in claim 1, wherein the connector comprises a lock and the syringe comprises a key configured to unlock the lock of the connector forming a lock and key mechanism to limit access to the system.

17. A system as in claim 16, wherein therapeutic agent flows from the syringe through the at least one opening from the injection lumen when the connector is reversibly coupled to the syringe.

18. A system as in claim 1, wherein a predetermined amount of the therapeutic fluid injected into the ocular implant corresponds to no more than about twice a volume of the ocular implant.

19. A system as in claim 18, wherein the volume of the ocular implant is no more than about 100 uL.

20. A system as in claim 18, wherein the syringe is pre-filled with the predetermined amount of the therapeutic fluid.

* * * * *